US011389152B2

(12) United States Patent
Gilmore et al.

(10) Patent No.: US 11,389,152 B2
(45) Date of Patent: Jul. 19, 2022

(54) OFF-CENTER TISSUE ANCHORS WITH TENSION MEMBERS

(71) Applicant: 4TECH INC., Waltham, MA (US)

(72) Inventors: Michael Gilmore, Ardrahan (IE); Paolo Denti, Opera (IT); Kevin Lynn, Athenry (IE); Idan Tobis, Beth Hashmonai (IL); Evin William Donnelly, Salthill (IE); Charlotte Murphy, Ardrahan (IE); Thomas Campbell, Westport (IE)

(73) Assignee: 4TECH INC., Waltham, MA (US)

( * ) Notice: Subject to any disclaimer, the term of this patent is extended or adjusted under 35 U.S.C. 154(b) by 258 days.

(21) Appl. No.: 15/165,768

(22) Filed: May 26, 2016

(65) Prior Publication Data
US 2016/0262741 A1    Sep. 15, 2016

Related U.S. Application Data

(60) Provisional application No. 62/167,660, filed on May 28, 2015.

(51) Int. Cl.
A61B 17/04          (2006.01)
A61B 17/068         (2006.01)
(Continued)

(52) U.S. Cl.
CPC ...... *A61B 17/0401* (2013.01); *A61B 17/0057* (2013.01); *A61B 17/00234* (2013.01);
(Continued)

(58) Field of Classification Search
CPC ...... A61B 18/1492; A61B 2018/00351; A61B 2018/00357; A61B 2018/00363;
(Continued)

(56) References Cited

U.S. PATENT DOCUMENTS 4,214,349 A    7/1980 Munch
4,405,313 A    9/1983 Sisley et al.
(Continued)

FOREIGN PATENT DOCUMENTS

DE    102007043830    4/2009
EP       1568326       8/2005
(Continued)

OTHER PUBLICATIONS

WIPO Invitation to Pay Additional Fees and, where Applicable, Protest Fee, dated Oct. 13, 2016, which issued during the processing of International Patent Application No. PCT/IL2016/000840.
(Continued)

*Primary Examiner* — Darwin P Erezo
*Assistant Examiner* — Erin L Colello
(74) *Attorney, Agent, or Firm* — UltimatEdge IP Law Group, P.C.; Dean G. Stathakis; Vito A. Canuso, III

(57) ABSTRACT

A tissue anchor includes a shaft, a tissue-coupling element, and a flexible elongate tension member. The tissue-coupling element includes a wire, which is shaped as an open loop having more than one turn when the tissue anchor is unconstrained. The tension member includes a distal portion that is fixed to a site on the open loop, a proximal portion, which has a longitudinal segment that runs alongside at least a portion of the shaft, and a crossing portion, which (i) is disposed between the distal and the proximal portions along the tension member, and (ii) crosses at least a portion of the open loop when the tissue anchor is unconstrained. The tissue anchor is configured to allow relative axial motion between the at least a portion of the shaft and the longitudinal segment of the proximal portion of the tension member when the tissue anchor is unconstrained.

80 Claims, 40 Drawing Sheets

(51) Int. Cl.
  *A61B 17/10* (2006.01)
  *A61F 2/82* (2013.01)
  *A61F 2/24* (2006.01)
  *A61B 17/00* (2006.01)
  *A61F 2/915* (2013.01)
  *A61B 17/064* (2006.01)

(52) U.S. Cl.
  CPC ............ *A61B 17/068* (2013.01); *A61B 17/10* (2013.01); *A61F 2/2442* (2013.01); *A61F 2/2478* (2013.01); *A61F 2/82* (2013.01); *A61F 2/915* (2013.01); *A61B 2017/00243* (2013.01); *A61B 2017/00309* (2013.01); *A61B 2017/00477* (2013.01); *A61B 2017/00575* (2013.01); *A61B 2017/00592* (2013.01); *A61B 2017/00615* (2013.01); *A61B 2017/00632* (2013.01); *A61B 2017/0409* (2013.01); *A61B 2017/0417* (2013.01); *A61B 2017/0419* (2013.01); *A61B 2017/0443* (2013.01); *A61B 2017/0464* (2013.01); *A61B 2017/0496* (2013.01); *A61B 2017/0645* (2013.01); *A61B 2017/0649* (2013.01); *A61F 2230/0091* (2013.01)

(58) Field of Classification Search
  CPC .. A61B 2018/00375; A61B 2018/1407; A61B 2018/00369; A61B 2018/0038; A61B 2018/00386; A61B 2018/00392; A61B 17/0401; A61B 2017/0496; A61B 2017/00575; A61B 2017/00867; A61B 2017/00243; A61B 17/0057; A61B 17/00234; A61B 17/10; A61B 2017/00615; A61B 2017/00592; A61B 2017/0417; A61B 2017/0419; A61B 2017/0409; A61B 2017/00632; A61B 2017/0464; A61B 2017/0443; A61B 2017/0645; A61B 2017/0649; A61F 2/2442; A61F 2250/0004; A61F 2250/001; A61F 2/2448; A61F 2/2478; A61F 2230/0091
  See application file for complete search history.

(56) References Cited

U.S. PATENT DOCUMENTS

| | | | |
|---|---|---|---|
| 4,423,525 A | | 1/1984 | Vallana |
| 4,444,207 A | | 4/1984 | Robicsek |
| 4,493,329 A | | 1/1985 | Crawford et al. |
| 4,532,926 A | | 8/1985 | O'Holla |
| 4,548,202 A | | 10/1985 | Duncan |
| 4,625,727 A | | 12/1986 | Leiboff |
| 4,712,549 A | | 12/1987 | Peters et al. |
| 4,741,336 A | | 5/1988 | Failla et al. |
| 4,778,468 A | | 10/1988 | Hunt et al. |
| 4,808,157 A | | 2/1989 | Coombs |
| 4,853,986 A | | 8/1989 | Allen |
| 5,108,420 A | | 4/1992 | Marks |
| 5,330,521 A | | 7/1994 | Cohen |
| 5,336,233 A | | 8/1994 | Chen |
| 5,350,399 A | | 9/1994 | Erlebacher et al. |
| 5,450,860 A | | 9/1995 | O'Connor |
| 5,473,812 A | | 12/1995 | Morris et al. |
| 5,730,127 A | * | 3/1998 | Avitall ............... A61B 5/0422 600/374 |
| 5,755,760 A | * | 5/1998 | Maguire ............. A61B 5/0422 607/122 |
| 5,776,178 A | | 7/1998 | Pohndorf et al. |
| 5,792,400 A | | 8/1998 | Talja et al. |
| 5,823,955 A | * | 10/1998 | Kuck ............... A61B 18/1492 600/374 |
| 5,843,120 A | | 12/1998 | Israel |
| 5,843,164 A | | 12/1998 | Frantzen et al. |
| 5,904,697 A | | 5/1999 | Gifford et al. |
| 5,948,000 A | | 9/1999 | Larsen et al. |
| 5,957,953 A | | 9/1999 | DiPoto et al. |
| 6,010,113 A | | 1/2000 | Rotering |
| 6,027,523 A | | 2/2000 | Schmieding |
| 6,045,497 A | | 4/2000 | Schweich, Jr. et al. |
| 6,193,734 B1 | | 2/2001 | Bolduc et al. |
| 6,206,913 B1 | | 3/2001 | Yencho et al. |
| 6,214,002 B1 | * | 4/2001 | Fleischman ........ A61B 18/1492 600/374 |
| 6,260,552 B1 | | 7/2001 | Mortier et al. |
| 6,298,272 B1 | | 10/2001 | Peterfeso et al. |
| 6,299,635 B1 | | 10/2001 | Frantzen |
| 6,332,893 B1 | | 12/2001 | Mortier et al. |
| 6,402,780 B2 | | 6/2002 | Williamson, IV et al. |
| 6,461,336 B1 | | 10/2002 | Larre |
| 6,533,810 B2 | | 3/2003 | Hankh et al. |
| 6,572,612 B2 | * | 6/2003 | Stewart ............. A61B 18/1492 606/41 |
| 6,575,976 B2 | | 6/2003 | Grafton |
| 6,602,288 B1 | * | 8/2003 | Cosgrove ............. A61F 2/2445 623/2.36 |
| 6,613,078 B1 | | 9/2003 | Barone |
| 6,613,079 B1 | | 9/2003 | Wolinsky |
| 6,616,684 B1 | | 9/2003 | Vidlund et al. |
| 6,626,899 B2 | | 9/2003 | Houser et al. |
| 6,626,930 B1 | | 9/2003 | Allen et al. |
| 6,629,534 B1 | * | 10/2003 | St. Goar .......... A61B 17/00234 128/898 |
| 6,629,921 B1 | | 10/2003 | Schweich, Jr. et al. |
| 6,635,068 B1 | * | 10/2003 | Dubrul ............. A61B 17/12022 606/200 |
| 6,641,597 B2 | | 11/2003 | Burkhart et al. |
| 6,702,846 B2 | | 3/2004 | Mikus |
| 6,723,038 B1 | | 4/2004 | Schroeder et al. |
| 6,730,118 B2 | | 5/2004 | Spenser et al. |
| 6,743,198 B1 | * | 6/2004 | Tihon ...................... A61F 2/04 604/104 |
| 6,746,472 B2 | | 6/2004 | Frazier et al. |
| 6,752,813 B2 | * | 6/2004 | Goldfarb .......... A61B 17/00234 606/139 |
| 6,776,754 B1 | | 8/2004 | Wilk |
| 6,797,001 B2 | | 9/2004 | Mathis |
| 6,884,250 B2 | | 4/2005 | Monassevitch |
| 6,908,478 B2 | | 6/2005 | Alferness et al. |
| 6,926,714 B1 | * | 8/2005 | Sra ..................... A61B 18/1492 606/41 |
| 6,929,660 B1 | | 8/2005 | Ainsworth et al. |
| 7,018,406 B2 | | 3/2006 | Seguin et al. |
| 7,018,408 B2 | | 3/2006 | Bailey et al. |
| 7,037,290 B2 | | 5/2006 | Gardeski et al. |
| 7,041,097 B1 | | 5/2006 | Webler |
| 7,056,333 B2 | | 6/2006 | Walse |
| 7,063,711 B1 | | 6/2006 | Loshakove et al. |
| 7,077,861 B2 | | 7/2006 | Spence |
| 7,101,395 B2 | | 9/2006 | Tremulis et al. |
| 7,101,396 B2 | | 9/2006 | Artof et al. |
| 7,125,421 B2 | | 10/2006 | Tremulis et al. |
| 7,144,363 B2 | | 12/2006 | Pai et al. |
| 7,159,593 B2 | | 1/2007 | McCarthy et al. |
| 7,166,127 B2 | * | 1/2007 | Spence ............... A61B 17/0401 606/139 |
| 7,169,187 B2 | | 1/2007 | Datta |
| 7,175,625 B2 | | 2/2007 | Culbert |
| 7,179,282 B2 | | 2/2007 | Alferness et al. |
| 7,186,262 B2 | | 3/2007 | Saadat |
| 7,189,199 B2 | | 3/2007 | McCarthy et al. |
| 7,198,646 B2 | | 4/2007 | Figulla et al. |
| 7,201,772 B2 | | 4/2007 | Schwammenthal |
| 7,211,107 B2 | | 5/2007 | Bruckheime et al. |
| 7,258,697 B1 | | 8/2007 | Cox et al. |
| 7,311,697 B2 | | 12/2007 | Osborne |
| 7,311,705 B2 | * | 12/2007 | Sra ..................... A61B 18/1492 606/41 |
| 7,311,728 B2 | | 12/2007 | Solem et al. |
| 7,316,706 B2 | | 1/2008 | Bloom et al. |

(56) References Cited

U.S. PATENT DOCUMENTS

| | | |
|---|---|---|
| 7,316,710 B1 | 1/2008 | Cheng et al. |
| 7,329,279 B2 | 2/2008 | Haug et al. |
| 7,335,213 B1 | 2/2008 | Hyde et al. |
| 7,338,506 B2 | 3/2008 | Caro |
| 7,351,256 B2 | 4/2008 | Hojeibane |
| 7,371,244 B2 | 5/2008 | Chatlynne et al. |
| 7,374,573 B2 | 5/2008 | Gabbay |
| 7,390,329 B2 | 6/2008 | Westra et al. |
| 7,435,248 B2 * | 10/2008 | Taimisto ............ A61B 18/1492 |
| | | 600/374 |
| 7,500,989 B2 | 3/2009 | Solem et al. |
| 7,503,931 B2 | 3/2009 | Kowalsky et al. |
| 7,510,575 B2 | 3/2009 | Spenser et al. |
| 7,530,995 B2 | 5/2009 | Quijano et al. |
| 7,547,321 B2 | 6/2009 | Silvestri et al. |
| 7,549,983 B2 | 6/2009 | Roue et al. |
| 7,597,703 B2 | 10/2009 | Sater |
| 7,608,102 B2 | 10/2009 | Adams et al. |
| 7,618,449 B2 * | 11/2009 | Tremulis ............ A61B 17/0401 |
| | | 623/2.11 |
| 7,628,797 B2 | 12/2009 | Tieu et al. |
| 7,632,303 B1 | 12/2009 | Stalker et al. |
| 7,666,204 B2 | 2/2010 | Thornton et al. |
| 7,758,632 B2 | 7/2010 | Hojeibane et al. |
| 7,771,467 B2 | 8/2010 | Svensson |
| 7,780,726 B2 | 8/2010 | Seguin |
| 7,803,187 B2 | 9/2010 | Hauser |
| 7,837,727 B2 | 11/2010 | Goetz et al. |
| 7,850,685 B2 * | 12/2010 | Kunis ................ A61B 18/1815 |
| | | 606/41 |
| 7,857,846 B2 | 12/2010 | Alferness et al. |
| 7,871,433 B2 | 1/2011 | Lattouf |
| 7,942,927 B2 | 5/2011 | Kaye et al. |
| 7,972,378 B2 | 7/2011 | Tabor et al. |
| 7,991,484 B1 | 8/2011 | Sengupta et al. |
| 7,992,567 B2 | 8/2011 | Hirotsuka |
| 7,993,368 B2 | 8/2011 | Gambale et al. |
| 8,010,207 B2 | 8/2011 | Smits et al. |
| 8,025,495 B2 | 9/2011 | Hardert et al. |
| 8,029,518 B2 * | 10/2011 | Goldfarb ................ A61B 17/12 |
| | | 606/139 |
| 8,052,592 B2 | 11/2011 | Goldfarb et al. |
| 8,092,525 B2 | 1/2012 | Eliasen et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 * | 3/2012 | Spence ............ A61B 17/0401 |
| | | 623/2.36 |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,172,898 B2 | 5/2012 | Alferness et al. |
| 8,197,441 B2 | 6/2012 | Webler et al. |
| 8,216,302 B2 | 7/2012 | Wilson et al. |
| 8,236,013 B2 | 8/2012 | Chu |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,295,902 B2 * | 10/2012 | Salahieh ................ A61B 5/01 |
| | | 600/374 |
| 8,323,335 B2 | 12/2012 | Rowe et al. |
| 8,332,051 B2 | 12/2012 | Sommer et al. |
| 8,398,672 B2 | 3/2013 | Kleshinski et al. |
| 8,425,402 B2 | 4/2013 | Annest et al. |
| 8,449,606 B2 | 5/2013 | Eliasen et al. |
| 8,475,525 B2 | 7/2013 | Maisano et al. |
| 8,480,730 B2 | 7/2013 | Maurer et al. |
| 8,523,881 B2 | 9/2013 | Cabiri et al. |
| 8,545,553 B2 | 10/2013 | Zipory et al. |
| 8,628,569 B2 | 1/2014 | Benichou et al. |
| 8,628,571 B1 | 1/2014 | Hacohen |
| 8,641,704 B2 * | 2/2014 | Werneth ............ A61B 18/1492 |
| | | 606/32 |
| 8,721,588 B2 | 5/2014 | Echarri et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,852,272 B2 | 10/2014 | Gross et al. |
| 8,858,623 B2 | 10/2014 | Miller et al. |
| 8,870,949 B2 | 10/2014 | Rowe |
| 8,870,950 B2 | 10/2014 | Hacohen |
| 8,961,594 B2 | 2/2015 | Maisano et al. |
| 8,961,595 B2 | 2/2015 | Alkhatib |
| 8,961,596 B2 | 2/2015 | Maisano et al. |
| 8,979,922 B2 | 3/2015 | Jayasinghe et al. |
| 9,005,273 B2 | 4/2015 | Salahieh et al. |
| 9,034,032 B2 | 5/2015 | McLean et al. |
| 9,034,033 B2 | 5/2015 | McLean et al. |
| 9,173,712 B2 | 11/2015 | Annest et al. |
| 9,241,702 B2 | 1/2016 | Maisano et al. |
| 9,326,870 B2 | 5/2016 | Berglund et al. |
| 2002/0013571 A1 * | 1/2002 | Goldfarb ............ A61B 17/0469 |
| | | 606/1 |
| 2002/0032481 A1 | 5/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0069570 A1 * | 4/2003 | Witzel ................ A61B 18/1492 |
| | | 606/28 |
| 2003/0083742 A1 | 5/2003 | Spence et al. |
| 2003/0093096 A1 | 5/2003 | McGuckin, Jr. et al. |
| 2003/0144732 A1 * | 7/2003 | Cosgrove ............ A61F 2/2445 |
| | | 623/2.11 |
| 2003/0167071 A1 | 9/2003 | Martin et al. |
| 2003/0225454 A1 | 12/2003 | Mathis et al. |
| 2003/0229350 A1 | 12/2003 | Kay |
| 2003/0236568 A1 | 12/2003 | Hojeibane et al. |
| 2004/0039442 A1 * | 2/2004 | St. Goar .......... A61B 17/00234 |
| | | 623/2.36 |
| 2004/0117009 A1 | 6/2004 | Cali et al. |
| 2004/0133274 A1 | 7/2004 | Webler et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0220596 A1 * | 11/2004 | Frazier ................ A61B 17/0057 |
| | | 606/153 |
| 2004/0236419 A1 | 11/2004 | Milo |
| 2004/0260317 A1 | 12/2004 | Bloom et al. |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059997 A1 | 3/2005 | Bauman et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0154448 A1 | 7/2005 | Cully et al. |
| 2005/0177180 A1 | 8/2005 | Kaganov et al. |
| 2005/0177228 A1 | 8/2005 | Solem |
| 2005/0203606 A1 | 9/2005 | Vancamp |
| 2005/0216039 A1 | 9/2005 | Lederman |
| 2005/0216079 A1 | 9/2005 | MaCoviak |
| 2005/0222665 A1 | 10/2005 | Arayani |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0009800 A1 | 1/2006 | Christianson et al. |

(56) References Cited

U.S. PATENT DOCUMENTS

| | | |
|---|---|---|
| 2006/0020247 A1* | 1/2006 | Kagan .............. A61B 17/00234 604/264 |
| 2006/0020326 A9 | 1/2006 | Bolduc et al. |
| 2006/0020327 A1 | 1/2006 | Lashinski et al. |
| 2006/0052821 A1 | 3/2006 | Abbot et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0189993 A1* | 8/2006 | Stone .............. A61B 17/0401 604/506 |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0259135 A1 | 11/2006 | Navia et al. |
| 2006/0259137 A1 | 11/2006 | Artof et al. |
| 2006/0276871 A1* | 12/2006 | Lamson ............. A61B 17/0401 623/1.11 |
| 2006/0276891 A1 | 12/2006 | Nieminen et al. |
| 2006/0282161 A1 | 12/2006 | Huynh et al. |
| 2007/0016287 A1 | 1/2007 | Cartledge |
| 2007/0016288 A1 | 1/2007 | Gurskis |
| 2007/0021781 A1 | 1/2007 | Jervis et al. |
| 2007/0027533 A1* | 2/2007 | Douk .................... A61F 2/2445 623/2.11 |
| 2007/0032787 A1 | 2/2007 | Hassett et al. |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0067027 A1* | 3/2007 | Moaddeb ............. A61F 2/2448 623/2.11 |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1* | 5/2007 | Davidson ......... A61B 17/00234 606/144 |
| 2007/0123936 A1 | 5/2007 | Goldin et al. |
| 2007/0144539 A1 | 6/2007 | van der Burg et al. |
| 2007/0162107 A1 | 7/2007 | Haug et al. |
| 2007/0168013 A1 | 7/2007 | Douglas |
| 2007/0185532 A1* | 8/2007 | Stone ................ A61B 17/0401 606/232 |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0233239 A1* | 10/2007 | Navia .................... A61F 2/2445 623/2.37 |
| 2007/0244554 A1* | 10/2007 | Rafiee .................... A61F 2/2451 623/2.11 |
| 2007/0244556 A1* | 10/2007 | Rafiee .................... A61F 2/2451 623/2.11 |
| 2007/0250160 A1 | 10/2007 | Rafiee |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1* | 1/2008 | Stone .............. A61B 17/0401 606/316 |
| 2008/0027483 A1 | 1/2008 | Cartledge |
| 2008/0035160 A1 | 2/2008 | Woodson et al. |
| 2008/0058866 A1 | 3/2008 | Young et al. |
| 2008/0077231 A1 | 3/2008 | Heringes et al. |
| 2008/0097595 A1 | 4/2008 | Gabbay |
| 2008/0140116 A1 | 6/2008 | Bonutti |
| 2008/0167714 A1* | 7/2008 | St. Goar .......... A61B 17/00234 623/2.11 |
| 2008/0190989 A1 | 8/2008 | Crews et al. |
| 2008/0228267 A1 | 9/2008 | Spence et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0093670 A1 | 4/2009 | Annest |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries |
| 2009/0240326 A1 | 9/2009 | Wilson et al. |
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | Van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab |
| 2010/0174358 A1 | 7/2010 | Rabkin |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |

(56) References Cited

U.S. PATENT DOCUMENTS

| | | |
|---|---|---|
| 2010/0324668 A1 | 12/2010 | Maurer et al. |
| 2011/0004296 A1 | 1/2011 | Lutter et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098727 A1 | 4/2011 | Kaiser et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0184510 A1 | 7/2011 | Maisano |
| 2011/0190879 A1 | 8/2011 | Bobo et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0143320 A1 | 1/2012 | Eliasen et al. |
| 2012/0035712 A1 | 2/2012 | Maisano |
| 2012/0083806 A1 | 4/2012 | Goertzen |
| 2012/0123531 A1* | 5/2012 | Tsukashima ........... A61F 2/2448 623/2.37 |
| 2012/0130374 A1 | 5/2012 | Bouduban et al. |
| 2012/0130421 A1 | 5/2012 | Hafez et al. |
| 2012/0158053 A1 | 6/2012 | Paulos |
| 2012/0179086 A1* | 7/2012 | Shank ................... A61F 2/04 604/8 |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0030522 A1 | 1/2013 | Rowe et al. |
| 2013/0041459 A1 | 2/2013 | Wilson et al. |
| 2013/0053951 A1 | 2/2013 | Baliarda |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0253640 A1* | 9/2013 | Meiri ................. A61B 17/0487 623/2.11 |
| 2013/0281760 A1 | 10/2013 | Farnan et al. |
| 2013/0296925 A1 | 11/2013 | Chanduszko et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0058405 A1 | 2/2014 | Foster |
| 2014/0114390 A1 | 4/2014 | Tobis et al. |
| 2014/0114404 A1* | 4/2014 | Gammie ............ A61B 17/0401 623/2.11 |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0275756 A1 | 9/2014 | Bender et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018876 A1 | 1/2015 | Ewers et al. |
| 2015/0018940 A1 | 1/2015 | Quill et al. |
| 2015/0025553 A1 | 1/2015 | Del Nido et al. |
| 2015/0045879 A1 | 2/2015 | Longoria et al. |
| 2015/0051698 A1 | 2/2015 | Baliarda et al. |
| 2015/0073545 A1 | 3/2015 | Braido |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142103 A1 | 5/2015 | Vidlund |
| 2015/0182336 A1 | 7/2015 | Zipory et al. |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2016/0242762 A1 | 8/2016 | Gilmore et al. |
| 2017/0209137 A1* | 7/2017 | Gilmore ............ A61B 17/0401 |

FOREIGN PATENT DOCUMENTS

| | | |
|---|---|---|
| EP | 1759663 | 3/2007 |
| EP | 1 836 971 | 9/2007 |
| EP | 1 968 491 | 7/2010 |
| WO | 1992/005093 | 4/1992 |
| WO | 1997/041778 | 11/1997 |
| WO | 2000/28923 | 5/2000 |
| WO | 2001/010306 | 2/2001 |
| WO | 2004/069055 | 8/2004 |
| WO | 2004/082538 | 9/2004 |
| WO | 2005/021063 | 3/2005 |
| WO | 2005/102194 | 11/2005 |
| WO | 2006/097931 | 9/2006 |
| WO | 2007/080595 | 7/2007 |
| WO | 2008/068756 | 6/2008 |
| WO | 2009/039400 | 3/2009 |
| WO | 2009081396 A2 | 7/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/128502 | 11/2010 |
| WO | 2010/128503 | 11/2010 |
| WO | 2011/051942 | 5/2011 |
| WO | 2011/089601 | 7/2011 |
| WO | 2011/143263 | 11/2011 |
| WO | 2012/127309 | 9/2012 |
| WO | 2013/011502 | 1/2013 |
| WO | 2013003228 A1 | 1/2013 |
| WO | 2013/028145 | 2/2013 |
| WO | 2013/078497 | 6/2013 |
| WO | 2014/064694 | 5/2014 |
| WO | 2014/087402 | 6/2014 |
| WO | 2014/108903 | 7/2014 |
| WO | 2014/141239 | 9/2014 |
| WO | 2015015497 A1 | 2/2015 |
| WO | 2015/063580 | 5/2015 |
| WO | 2015/193728 | 12/2015 |

(56) References Cited

FOREIGN PATENT DOCUMENTS

| WO | 2016/087934 | 6/2016 |
|---|---|---|
| WO | 2016189391 A2 | 12/2016 |
| WO | 2017059426 A1 | 4/2017 |

OTHER PUBLICATIONS

WIPO International Search Report and a Written Opinion both dated Dec. 8, 2016, which issued during the processing of International Patent Application No. PCT/IL2016/000840.
USPTO Non-Final Office Action dated Sep. 26, 2017, which issued during the prosecution of U.S. Appl. No. 15/104,467.
WIPO International Search Report and a Written Opinion both dated Nov. 20, 2017, which issued during the processing of International Patent Application No. PCT/US2017/047442.
An International Search Report and a Written Opinion both dated Dec. 6, 2013, which issued during the prosecution of Applicant's PCT/IL2013/050470.
Alfieri et al., "An effective technique to correct anterior mitral leaflet prolapse," J Card Surg 14(6):468-470 (1999).
Alfieri et al., "Novel suture device for beating heart mitral leaflet approximation," Annals of Thoracic Surgery 74:1488 1493 (2002).
Alfieri et al., "The double orifice technique in mitral valve repair: a simple solution for complex problems," Journal of Thoracic Cardiovascular Surgery 122:674-681 (2001).
Amplatzer Cardiac Plug Brochure (English Pages), AGA Medical Corporation, Plymouth, MN Copyright 2008-2011, downloaded Jan. 11, 2011.
Beale BS, "Surgical Repair of Collateral Ligament Injuries," presented at 63rd CVMA Convention, Halifax, Nova Scotia, Canada, Jul. 6-9, 2011.
Dentistry Today, "Implant Direct" product information page, Jun. 1, 2011, downloaded Dec. 10, 2012 from http://dentistrytoday.com/top25implant-i/5558-implant-direct.
Maisano et al., "The double-orifice technique as a standardized approach to treat mitral regurgitation due to severe myxomatous disease: surgical technique," European Journal of Cardio-thoracic Surgery 17 (2000) 201-205.
Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.
Smith & Nephew MINITAC™ TI 2.0 Suture Anchor Product Description, downloaded on Dec. 9, 2012 from http://global.smith-nephew.com/us/MINITAC_TI_2_SUTURE_ANCHR_3127.htm.
Second Notice of Allowance dated May 10, 2013, which issued during the prosecution of U.S. Appl. No. 12/692,061.
An Interview Summary dated Oct. 24, 2012, which issued during the prosecution of U.S. Appl. No. 12/692,061.
An Office Action dated Jul. 6, 2012, which issued during the prosecution of U.S. Appl. No. 12/692,061.
A Notice of Allowance dated Mar. 6, 2013, which issued during the prosecution of U.S. Appl. No. 12/692,061.
An International Search Report and a Written Opinion both dated May 19, 2011, which issued during the prosecution of Applicant's PCT/IL11/00064.
An International Search Report and a Written Opinion both dated Jan. 22, 2013, which issued during the prosecution of Applicant's PCT/IL2012/000282.
An Office Action dated Dec. 5, 2013, which issued during the prosecution of U.S. Appl. No. 13/485,145.
An International Search Report and a Written Opinion both dated Mar. 17, 2014, which issued during the prosecution of Applicant's PCT/IL2013/050937.
Invitation to pay additional fees in PCT/IL2014/050027 dated Apr. 4 2014.
An International Search Report and a Written Opinion both dated May 28, 2014, which issued during the prosecution of Applicant's PCT/IL2014/050027.
U.S. Appl. No. 60/902,146, filed Feb. 16, 2007.

European Search Report dated Apr. 10, 2015, which issued during the prosecution of Applicant's European App No. 11734451.5.
European Search Report dated May 15, 2015, which issued during the prosecution of Applicant's Eurogean App No. 12814417.7.
An Office Action dated Sep. 14, 2015, which issued during the prosecution of U.S. Appl. No. 13/553,081.
An English Translation of an Office Action dated Jun. 30, 2015 which issued during the prosecution of Chinese Patent Application No. 201180015301.6.
An English Translation of an Office Action dated Jul. 7, 2015 which issued during the prosecution of Japanese Patent Application No. 2012-549463.
An Office Action dated Oct. 7, 2015, which issued during the prosecution of U.S. Appl. No. 13/574,088.
Invitation to Pay Additional Fees dated Apr. 20, 2015, which issuef during the prosecution of Applicant's PCT/IB2014/002351.
An International Search Report and a Written Opinion both dated Jun. 10, 2015, which issued during the prosecution of Applicant's PCT/IB2014/002351.
An Office Action dated Feb. 2, 2015, which issued during the prosecution of U.S. Appl. No. 14/143,355.
An English Translation of an Office Action dated Feb. 10, 2015, which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An English Translation of an Office Action dated Jun. 30, 2014 which issued during the prosecution of Chinese Patent Application No. 201180015301.6.
An Office Action dated Sep. 25, 2014, which issued during the prosecution of U.S. Appl. No. 13/485,145.
An English Translation of an Office Action dated Oct. 28, 2014,which issued during the prosecution of Japanese Patent Application No. 2012-549463.
Notice of Allowance dated Dec. 9, 2014, which issued during the prosecution of U.S. Appl. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8 2016, 2014, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
An Office Action dated May 11, 2016, which issued during the prosecution of U.S. Appl. No. 13/574,088.
An International Search Report and a Written Opinion both dated Apr. 15, 20165, 2014, which issued during the prosecution of Applicant's PCT/IB2015/002354.
U.S. Appl. No. 62/167,660, filed May 28, 2015.
An English Translation of an Office Action dated Jun. 23, 2016 which issued during the prosecution of Chinese Patent Application No. 201480028044.3. (the relevant part only).
U.S. Appl. No. 62/086,269, filed Dec. 2, 2014.
U.S. Appl. No. 15/104,467, filed Jun. 14, 2016, US 20170209137, U.S. Pat. No. 9,907,547.
U.S. Appl. No. 15/619,881, filed Jun. 12, 2017, US 20170273681.

(56) References Cited

OTHER PUBLICATIONS

CNIPA, Office Action for CN Patent Application Serial No. 2016800303355, dated Mar. 25, 2019 (English Translation).
EPO Article 94(3) EPC Communication for European Patent Application Serial No. 17191569.7, dated Nov. 27, 2018.
EPO, Communication in EP 16734021.5, pp. 8, dated Dec. 5, 2018.
WIPO, International Search Report and Written Opinion issued in IA PCT/US18/040147, pp. 16, dated Oct. 15, 2018.
WIPO, International Search Report and Written Opinion issued in PCT/US18/036609, dated Sep. 18, 2018.
USPTO, Non-Final Office Action for U.S. Appl. No. 15/619,881 (dated Apr. 18, 2019).
CIPO, First Office Action for CN Patent Application 201911053963.7. pp. 8 (dated Apr. 22, 2021).
CIPO, Second Office Action for CN Patent Application 201911053963.7, pp. 12 (dated Nov. 24, 2021).
EPO, Office Action for EP Patent Application 17191569.7, pp. 5 (dated Dec. 1, 2021).
USPTO, Non-Final Office Action for U.S. Appl. No. 16/811,070, pp. 10 (dated Jan. 19, 2022).
EPO, European Search Report for EP Patent Application 17191569.7 (dated Jan. 23, 2018).
USPTO, Notice of Allowance for U.S. Appl. No. 15/104,467 (dated Jan. 11, 2018).
USPTO, Non-Final Office Action of U.S. Appl. No. 16/003,408 (dated Aug. 6, 2020).

\* cited by examiner

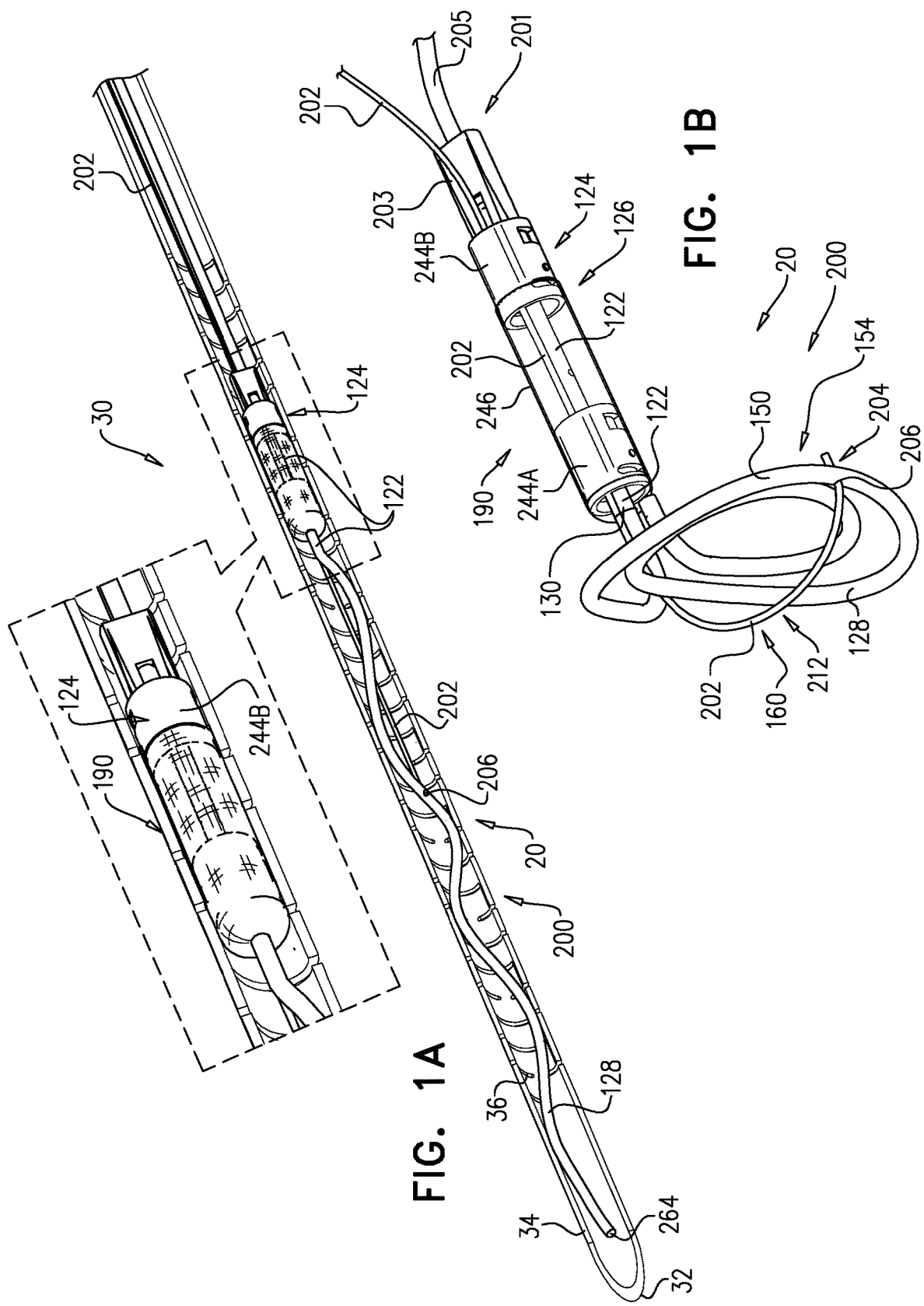

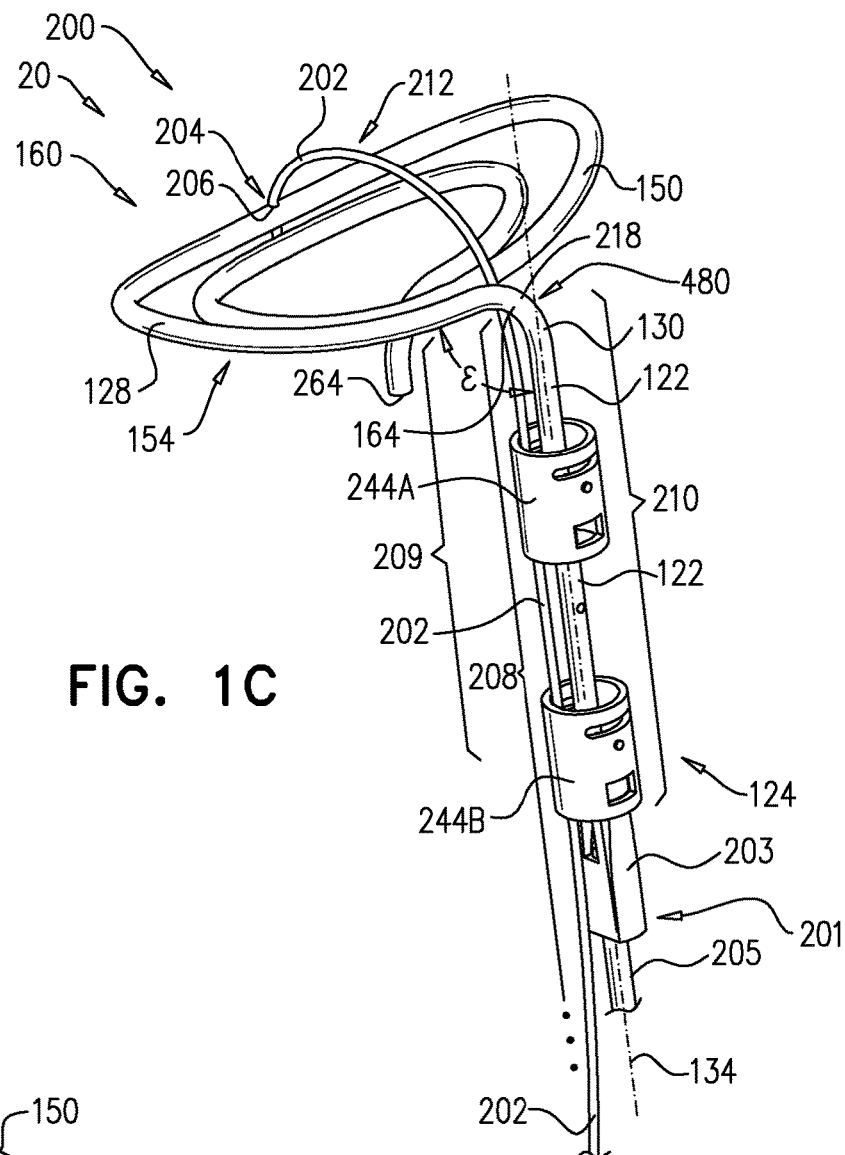
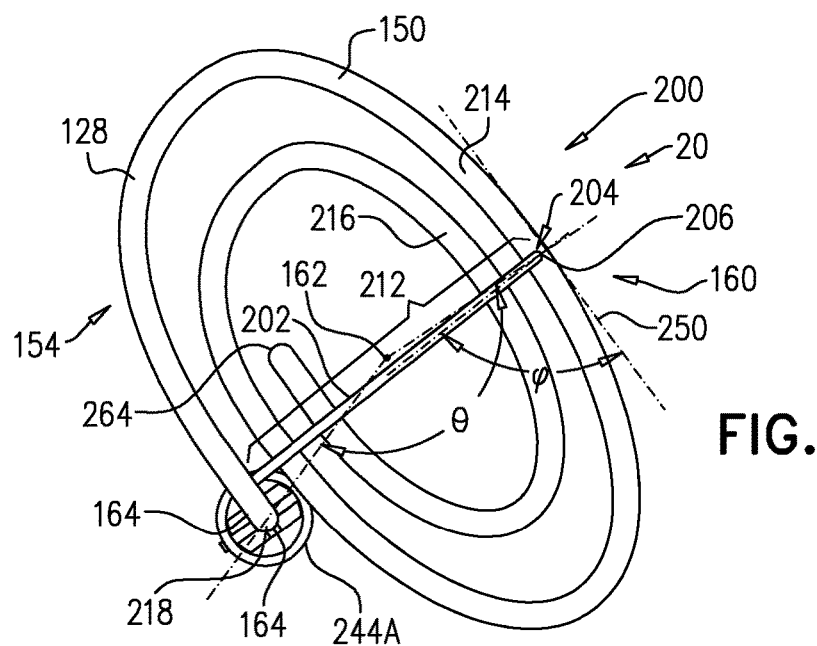
FIG. 1C
FIG. 1D

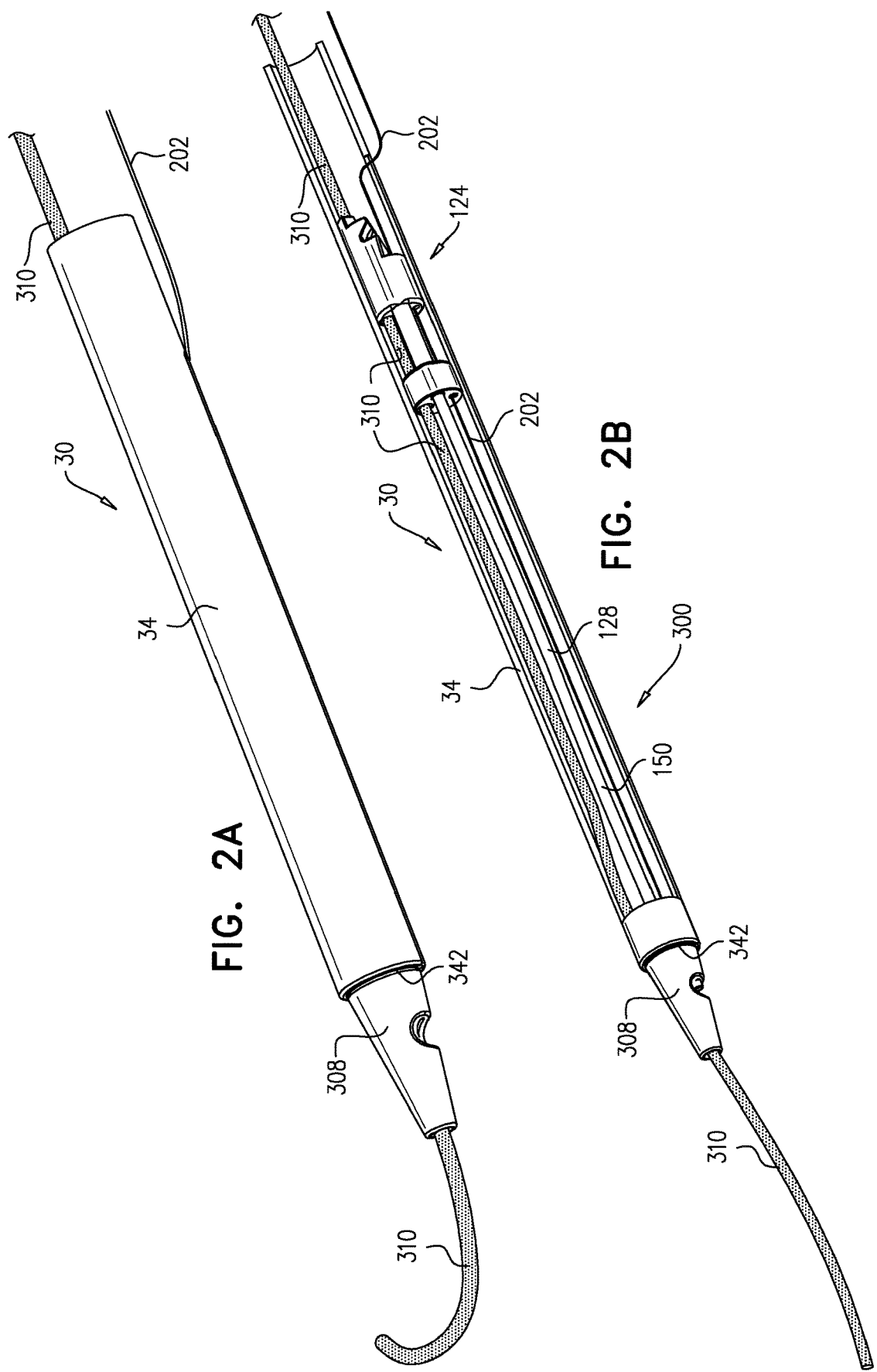

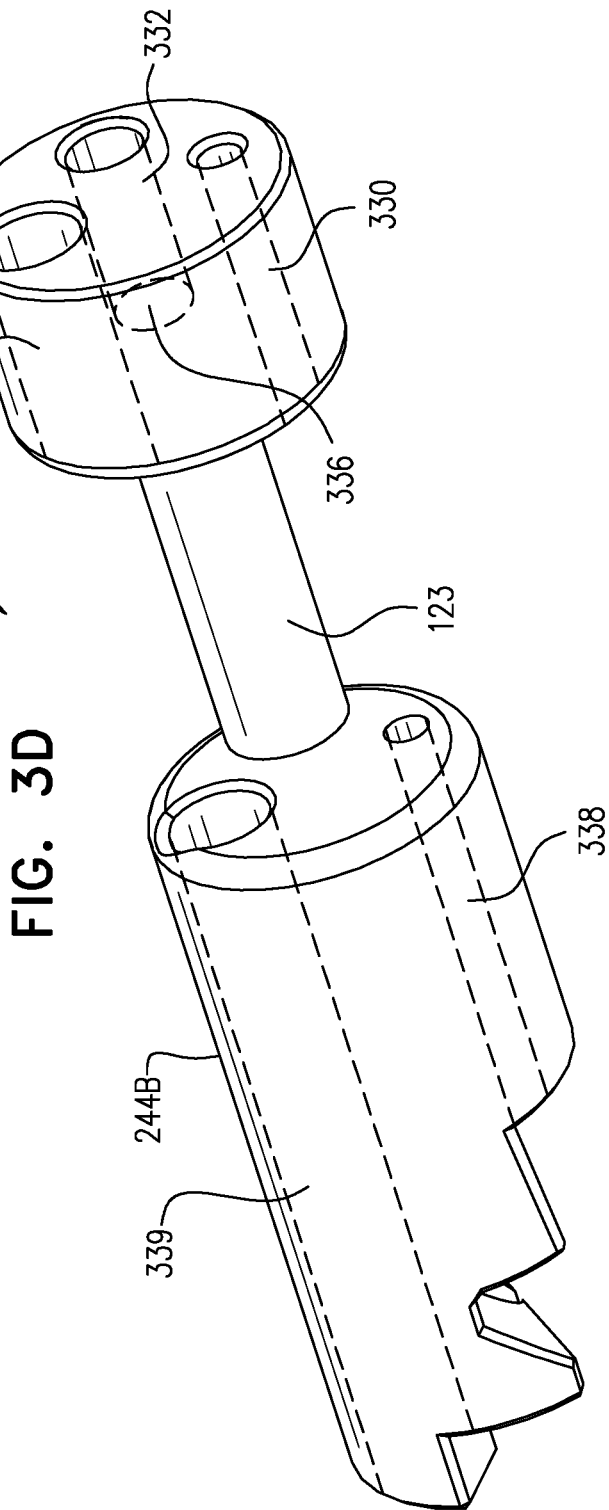

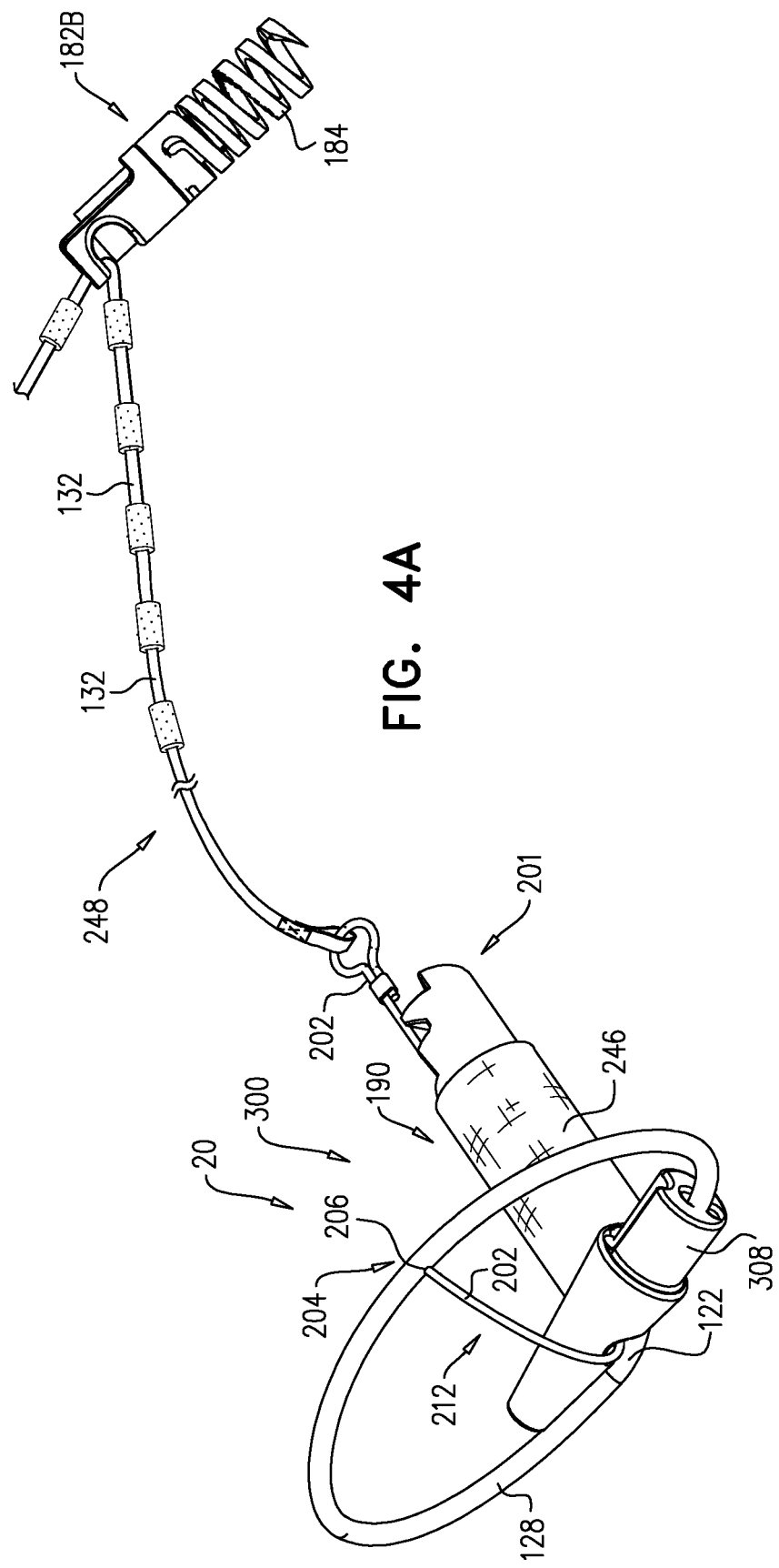

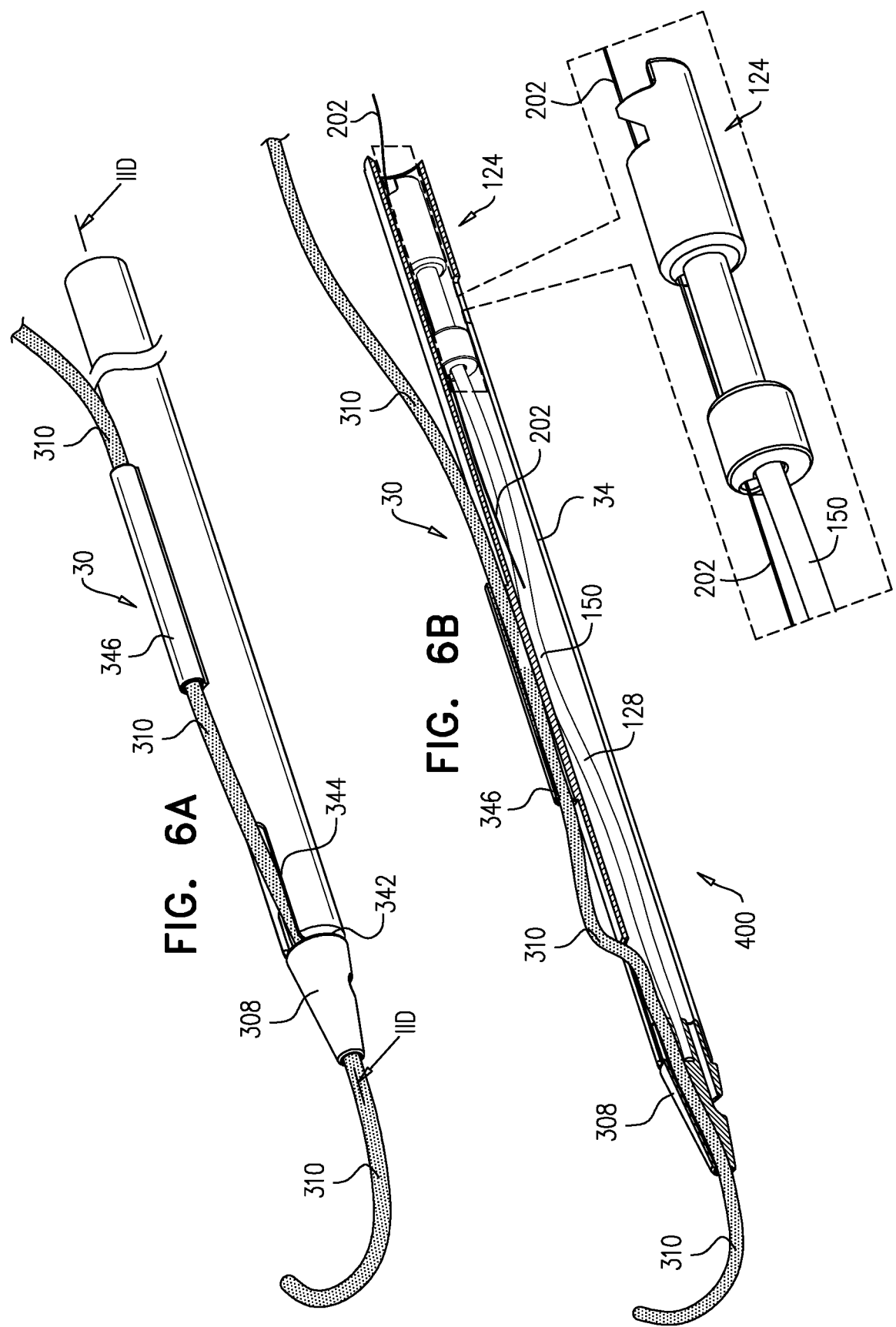

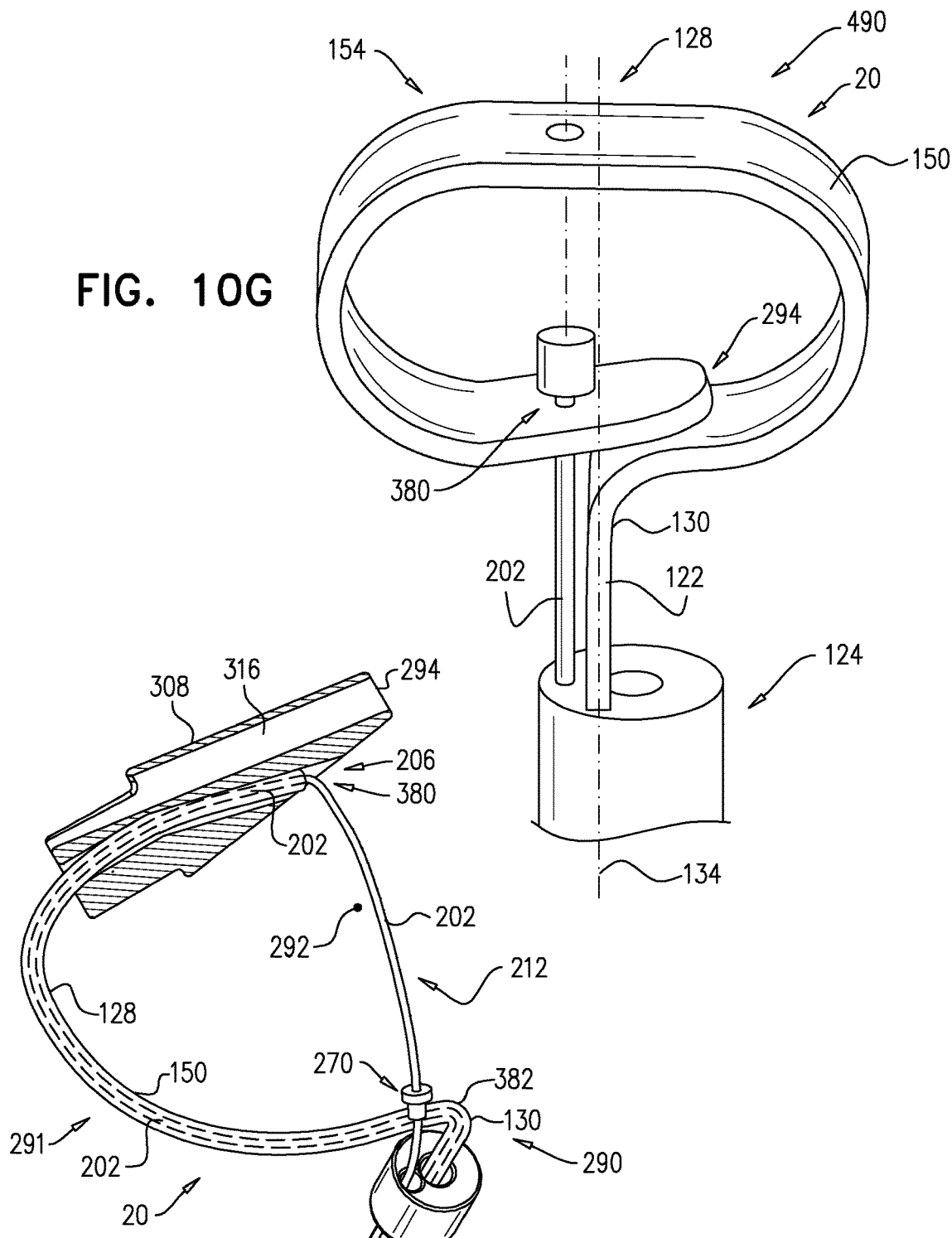

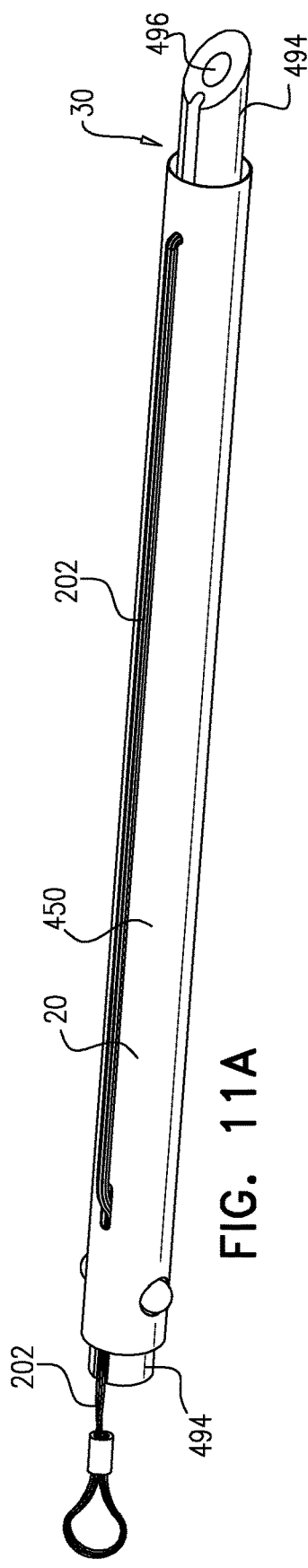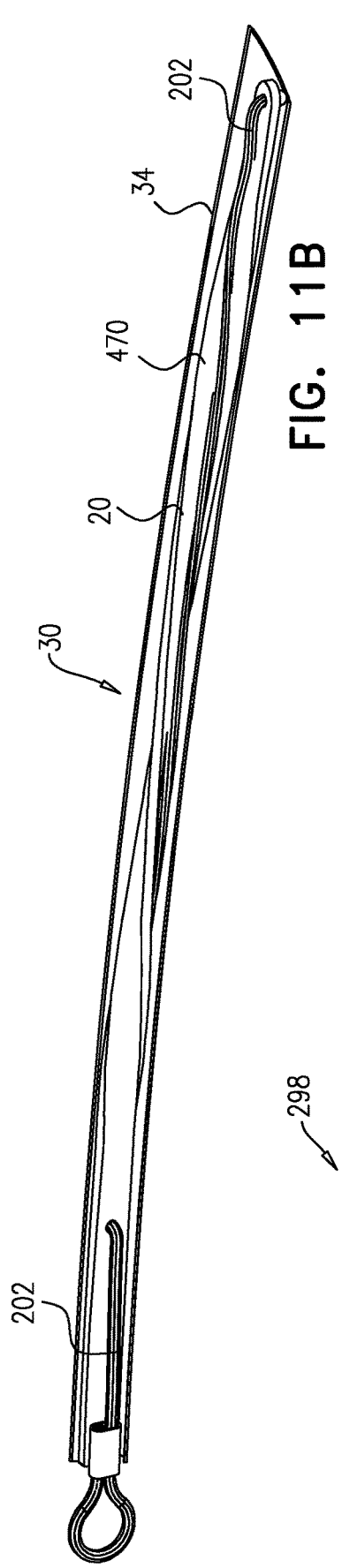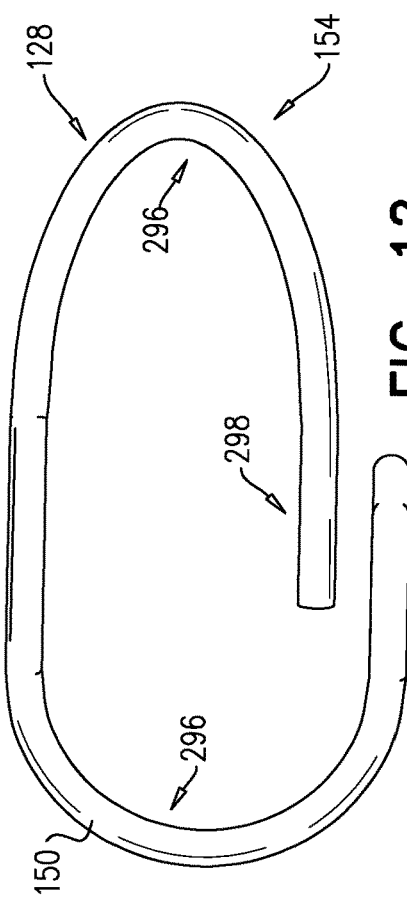

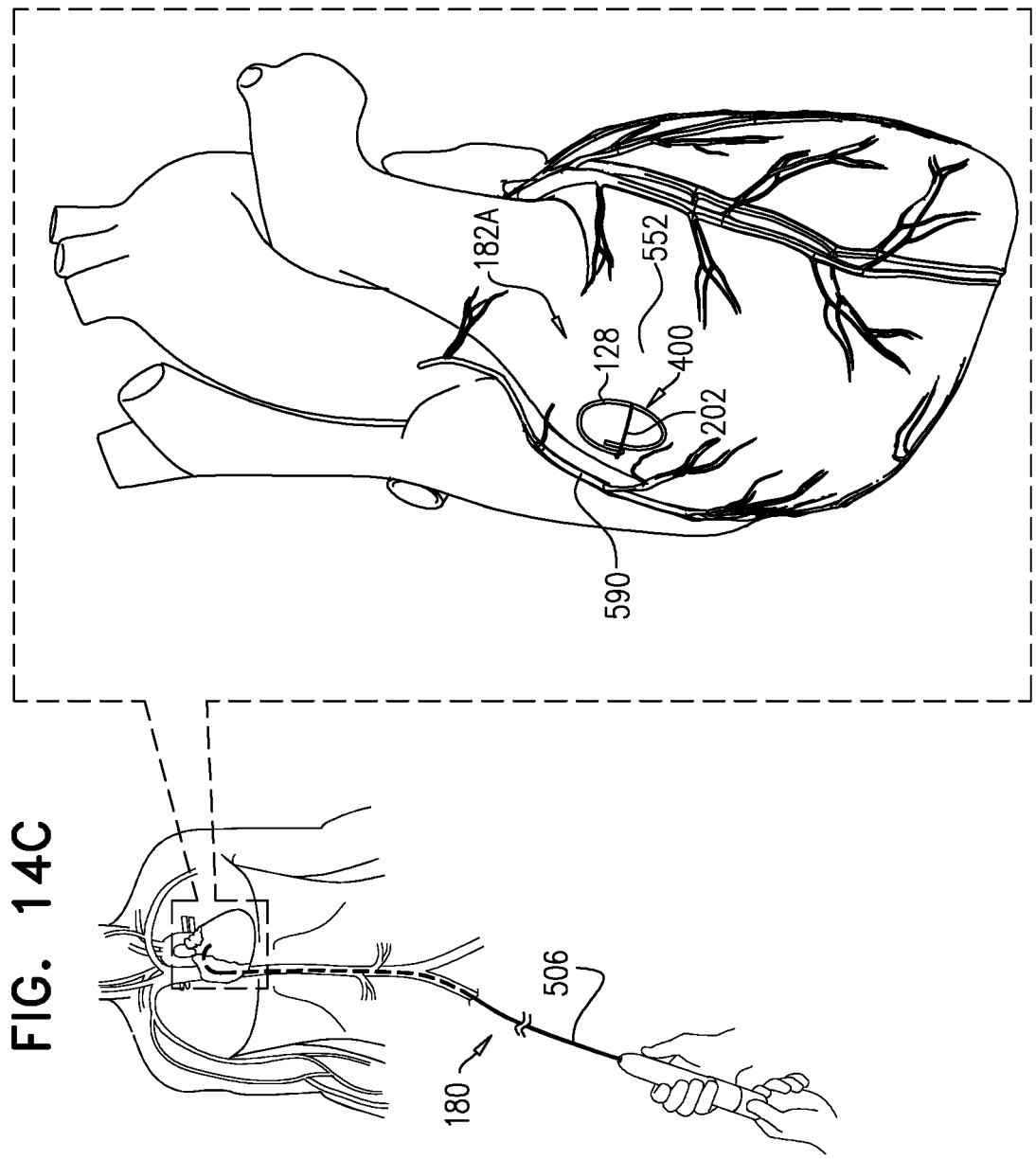

OFF-CENTER TISSUE ANCHORS WITH TENSION MEMBERS

CROSS-REFERENCE TO RELATED APPLICATIONS

The present application:

(a) claims priority from U.S. Provisional Application 62/167,660, filed May 28, 2015; and (b) is a continuation-in-part of International Application PCT/IB2015/002354, filed Dec. 2, 2015, which published as PCT Publication WO 2016/087934 to Gilmore et al., and which claims priority from (i) U.S. Provisional Application 62/086,269, filed Dec. 2, 2014, and (ii) U.S. Provisional Application 62/167,660, filed May 28, 2015.

The present application is related to International Application PCT/IB2016/000840, entitled, "Off-center tissue anchors with tension members," filed May 26, 2016 on even date herewith, which published as PCT Publication WO 2016/189391 to Gilmore et al., and which claims priority from the above-mentioned applications.

All of the above-mentioned applications are assigned to the assignee of the present application and are incorporated herein by reference.

FIELD OF THE APPLICATION

The present invention relates generally to tissue anchors, and specifically to tissue anchors for implantation in soft tissue, such as cardiac tissue.

BACKGROUND OF THE APPLICATION

Tissue anchors are used for anchoring elements, such as electrode leads or sutures, to tissue, such as bone or soft tissue.

SUMMARY OF THE APPLICATION

Some embodiments of the present invention provide a tissue anchor that comprises (a) an anchor shaft, (b) a tissue anchor head connected to a proximal portion of the anchor shaft, and (c) a tissue-coupling element, which extends from a distal end of the anchor shaft, and which comprises a wire, which is shaped as an open loop having more than one turn when the tissue anchor is unconstrained by a deployment tool. Typically, the tissue anchor further comprises a flexible elongate tension member, which is typically distinct from the wire of the tissue-coupling element, and which is fixed to a site on the open loop and crosses at least a portion of the open loop when the tissue anchor is unconstrained by the deployment tool. The flexible elongate tension member typically includes (a) a distal portion that is fixed to a site on the open loop, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses at least a portion of the open loop when the tissue anchor is unconstrained by the deployment tool.

Tension is applied to the tissue-coupling element of the tissue anchor via the flexible elongate tension member. The applied tension is resisted by the outward force of the open loop. The applied tension compresses and stiffens the open loop. This arrangement of tension distribution may overcome any natural tendency of the open loop to straighten if tension were to be applied along the central longitudinal axis via the anchor shaft, and thus may allow the application of a greater load to the open loop. It is noted that the maximum design stiffness of the open loop is constrained by the need for the open loop to be straightened for delivery in a deployment shaft of the deployment tool.

For some applications, the tissue-coupling element is off-center with respect to a central longitudinal axis of the anchor shaft. This off-centeredness allows the tissue-coupling element to be rotated during implantation so as to avoid contact with a sensitive anatomic structure, such as a blood vessel. The off-centeredness of the tissue-coupling element thus allows the surgeon to select an anchoring site from a plurality of anchoring sites around an exit site of the tissue anchor on the heart wall, without the need to relocate the exit site by removing the tissue-coupling element and again penetrating the deployment tool through the heart wall to redeliver the tissue-coupling element. The off-centeredness of the tissue-coupling element allows for the biasing of the tissue-coupling element away from the exit site, by rotating the tissue-coupling element to find a point of minimal impact on the cardiac circulation.

For some applications, a deployment tool is provided for delivering the tissue anchor, while in a constrained state, through a wall of a heart of a subject, typically by advancing a sharp distal piercing tip of the deployment tool through the wall. A surgeon, after delivering the tissue-coupling element through the wall of the heart, ascertains whether the tissue-coupling element overlies a coronary blood vessel, such as the right coronary artery (RCA). If the tissue-coupling element overlies the coronary blood vessel, the surgeon rotates the tissue anchor until the tissue-coupling element no longer overlies the coronary blood vessel. The surgeon then brings the tissue-coupling element into contact with an external surface of the heart, by applying tension the anchor head in the heart chamber.

Without the techniques of the present invention, the tissue-coupling element might inadvertently compress a blood vessel, which might result in cardiac complications including but not limited to angina, myocardial infarction, reduced blood flow, and/or a reduction in circulation efficiency in cardiac tissue. Removal of such an improperly positioned tissue-coupling element might be required, which might result in additional complications and injury to the patient.

For some applications, the anchor head is shaped so as to define a passage in which the proximal portion of the flexible elongate tension member is slidably disposed. The flexible elongate tension member comprises a locking stopper, which is axially fixed to the proximal or the crossing portion of the flexible elongate tension member. The locking stopper and the passage are sized and shaped such that the size and shape of the passage prevent proximal movement of the locking stopper past the passage. The locking stopper limits the total load that can be applied to the open loop by the flexible elongate tension member, thereby reducing excessive, unnecessary strain on the open loop. Additional load (tension) that is applied by the flexible elongate tension member pulls on the entire tissue anchor, and does not further increase the load applied across the open loop.

Typically, the tissue anchor is configured to allow relative axial motion between the at least a portion of the anchor shaft and the longitudinal segment of the proximal portion of the flexible elongate tension member when the tissue anchor is unconstrained by the deployment tool. Such axial motion allows tension to be applied to the flexible elongate tension member without also being applied to the anchor shaft, and allows the open loop to be unwound and the flexible elongate tension member to be disposed alongside a portion of the flexible elongate tension member. Typically, the longitudinal segment of the proximal portion of the flexible elongate tension member is coupled in sliding communication with the at least a portion of the anchor shaft when the tissue anchor is unconstrained by the deployment tool. For some applications, the tissue anchor comprises one or more annular elements, which are disposed around the at least a portion of the anchor shaft, and couple the flexible elongate tension member in the sliding communication with the at least a portion of the anchor shaft when the tissue anchor is unconstrained by the deployment tool. For example, the annular elements may comprise one or more collars, loops, or rings.

In experiments on porcine heart cadavers conducted by the inventors, a tissue anchor comprising the spiral and the flexible elongate tension member remained firmly implanted in tissue of the ventricular wall, without damaging the tissue, and without fracturing of the tissue anchor under high loads. The inventors found that loads of up to 25 N could be safety applied. It was noted that the tension applied through the flexible elongate tension member was of a magnitude of three times that of the load that could be applied through the central longitudinal axis of the anchor shaft.

In some applications of the present invention, the tissue-coupling element is shaped as an open shape when the tissue anchor is unconstrained by the deployment tool. The flexible elongate tension member (a) extends from a distal site on the open shape, the distal site located within 7 mm of a distal end of the open shape, and (b) includes a proximal portion, which has a longitudinal segment that runs alongside at least a portion of the anchor shaft when the tissue anchor is unconstrained by the deployment tool. For some applications, the distal site on the open shape is at the distal end of the open shape. For some applications, the wire is shaped so as to define a channel (i.e., the wire is tubular), and the flexible elongate tension member passes through at least a portion of the channel.

For some applications, a tissue anchor system is provided, which comprises (a) a first off-center tissue anchor, such as described above, (b) a second tissue anchor, and (c) one or more tethers, which are configured to couple (i) the anchor head of first tissue anchor to (ii) the second tissue anchor. For some applications, the second tissue anchor comprises a helical tissue-coupling element. For other applications, the second tissue anchor comprises a stent. For applications in which the tissue anchor comprises the flexible elongate tension member, as described above, the one or more tethers are fixed to the flexible elongate tension member. When tension is applied to the one or more tethers, the tension is transmitted to the flexible elongate tension member, rather than to the anchor shaft via the anchor head.

There is therefore provided, in accordance with an inventive concept 1 of the present invention, apparatus for delivery in a constrained state within a deployment tool, the apparatus including a tissue anchor, which includes:
an anchor shaft;
a tissue-coupling element, which (a) extends from a distal end of the anchor shaft, (b) includes a wire, and (c) is shaped as an open shape when the tissue anchor is unconstrained by the deployment tool; and
a flexible elongate tension member, which (a) extends from a distal site on the open shape, the distal site located within 7 mm of a distal end of the open shape, and (b) includes a proximal portion, which has a longitudinal segment that runs alongside at least a portion of the anchor shaft when the tissue anchor is unconstrained by the deployment tool,
wherein the tissue anchor is configured to allow relative axial motion between the at least a portion of the anchor shaft and the longitudinal segment of the proximal portion of the flexible elongate tension member when the tissue anchor is unconstrained by the deployment tool.

Inventive concept 2. The apparatus according to inventive concept 1, wherein a radius of the flexible elongate tension member is less than a radius of the wire.

Inventive concept 3. The apparatus according to inventive concept 2, wherein the radius of the flexible elongate tension member is less than 50% of the radius of the wire.

Inventive concept 4. The apparatus according to inventive concept 1, wherein the anchor shaft includes a sealing element.

Inventive concept 5. The apparatus according to inventive concept 1, wherein the anchor shaft has a central longitudinal axis that is straight when the tissue anchor is unconstrained by the deployment tool.

Inventive concept 6. The apparatus according to inventive concept 1, wherein the anchor shaft and the tissue-coupling element are integral to one another.

Inventive concept 7. The apparatus according to inventive concept 1, wherein a cross-sectional area of the wire is at least 0.09 mm2.

Inventive concept 8. The apparatus according to inventive concept 7, wherein the cross-sectional area of the wire is no more than 2.9 mm2.

Inventive concept 9. The apparatus according to inventive concept 1, wherein the flexible elongate tension member includes Nitinol.

Inventive concept 10. The apparatus according to inventive concept 1, wherein the open shape is an open loop having more than one turn when the tissue anchor is unconstrained by the deployment tool.

Inventive concept 11. The apparatus according to inventive concept 10, wherein the open loop is shaped as a spiral when the tissue anchor is unconstrained by the deployment tool.

Inventive concept 12. The apparatus according to inventive concept 11, wherein the spiral is shaped as a three-dimensional spiral when the tissue anchor is unconstrained by the deployment tool.

Inventive concept 13. The apparatus according to inventive concept 11, wherein the spiral is shaped as an elliptical spiral when the tissue anchor is unconstrained by the deployment tool.

Inventive concept 14. The apparatus according to inventive concept 10, wherein the open loop is shaped as a three-dimensional open loop when the tissue anchor is unconstrained by the deployment tool.

Inventive concept 15. The apparatus according to inventive concept 14, wherein, when the tissue anchor is unconstrained by the deployment tool:
a greatest longitudinal dimension of the three-dimensional open loop, measured in parallel to a central longitudinal axis of the anchor shaft, is between 1 and 5 mm, and
a greatest lateral dimension of the three-dimensional open loop, measured perpendicular to the central longitudinal axis, is between 4 and 20 mm.

Inventive concept 16. The apparatus according to inventive concept 10, wherein, when the tissue anchor is unconstrained by the deployment tool:
the open loop is shaped so as to define an outermost turn and a second-to-outermost at least partial turn, and the outermost turn at least partially overlaps the second-to-outermost at east partial turn.

inventive concept 17. The apparatus according to inventive concept 10, wherein, when the tissue anchor is unconstrained by the deployment tool, the open loop is shaped so as to define one or more curved segments and one or more straight segments.

Inventive concept 18. The apparatus according to inventive concept 17, wherein, when the tissue anchor is unconstrained by the deployment tool, the open loop is shaped so as to define the one or more curved segments and two or more straight segments.

Inventive concept 19. The apparatus according to inventive concept 10, wherein, when the tissue anchor is unconstrained by the deployment tool:

the open loop has a greatest lateral dimension, measured perpendicular to a central longitudinal axis of the anchor shaft, and a distance between (a) a radially-outer end of the open loop and (b) a radially-inner-most point of the open loop, measured perpendicular to the central longitudinal axis, is equal to at least 30% of the greatest lateral dimension.

Inventive concept 20. The apparatus according to inventive concept 19, wherein a ratio of the greatest longitudinal dimension and the greatest lateral dimension is between 1:2 and 1:18 when the tissue anchor is unconstrained by the deployment tool.

Inventive concept 21. The apparatus according to inventive concept 10, wherein the wire extends from the distal end of the anchor shaft at a radially-outer end of the open loop when the tissue anchor is unconstrained by the deployment tool.

Inventive concept 22. The apparatus according to inventive concept 21, wherein, when the tissue anchor is unconstrained by the deployment tool, the open loop surrounds a center point, and the wire does not intersect the center point.

Inventive concept 23. The apparatus according to inventive concept 10, wherein the wire extends from the distal end of the anchor shaft at a radially-inner end of the open loop when the tissue anchor is unconstrained by the deployment tool.

Inventive concept 24. The apparatus according to any one of inventive concepts wherein the distal site is located within 3 mm of the distal end of the open shape.

Inventive concept 25. The apparatus according to inventive concept 24, wherein the distal site on the open shape is at the distal end of the open shape.

Inventive concept 26. The apparatus according to any one of inventive concepts 1-23, wherein, when the tissue anchor is unconstrained by the deployment tool, (a) a line segment that terminates at (i) the distal site on the open shape and (ii) a proximal end of the tissue-coupling element may have a total length that equals a percentage of (b) a total length of the tissue-coupling element, measured the along tissue-coupling element, the percentage between 25% and 75%.

Inventive concept 27. The apparatus according to any one of inventive concepts 1-23, wherein the wire is shaped so as to define a channel, and wherein the flexible elongate tension member passes through at least a portion of the channel.

Inventive concept 28. The apparatus according to inventive concept 27, wherein the flexible elongate tension member passes through the entire channel, and the distal site on the open shape is a distal-end opening of the open shape.

Inventive concept 29. The apparatus according to inventive concept 28, wherein a distal end portion of the flexible elongate tension member is fixed at or beyond a proximal end of the open shape.

Inventive concept 30. The apparatus according to inventive concept 27, wherein the channel has a proximal lateral opening within 7 mm of a proximal end of the wire, and wherein the proximal portion of the flexible elongate tension member passes through the proximal lateral opening.

Inventive concept 31. The apparatus according to inventive concept 30, wherein the proximal portion of the flexible elongate tension member passes through the proximal lateral opening and through a proximal-end opening of the channel.

Inventive concept 32. The apparatus according to inventive concept 27, wherein the channel has a lateral opening at the site, and wherein the distal portion of the flexible elongate tension member passes through the lateral opening.

Inventive concept 33. The apparatus according to inventive concept 27, wherein the tissue-coupling element further includes a tip, which is fixed to a distal end of the wire, and has, at a widest longitudinal site along the tip, a greatest tip outer cross-sectional area that equals at least 150% of an average wire cross-sectional area of the wire, wherein the distal site is on the tip, wherein the tip is shaped so as to define an extension of the channel, and wherein the flexible elongate tension member passes through a portion of the tip in the extension of the channel, and exits the tip at the distal site.

Inventive concept 34. The apparatus according to any one of inventive concepts 1-23, wherein the wire is shaped so as to define first and second major opposing surfaces connected by first and second minor opposing surfaces, wherein the first and the second major opposing surfaces and the first and the second minor opposing surfaces extend along at least 90% of a total length of the wire, and wherein a total surface area of the first minor opposing surface is less than 10% of a total surface area of the major opposing surface.

Inventive concept 35. The apparatus according to inventive concept 34, wherein the wire is shaped so as to define an opening within 7 mm of a proximal end of the wire, and wherein the proximal portion of the flexible elongate tension member passes through the opening.

Inventive concept 36. The apparatus according to inventive concept 34, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 37. The apparatus according to inventive concept 34, wherein, when the tissue anchor is unconstrained by the deployment tool:

a greatest longitudinal dimension of the open shape, measured in parallel to a central longitudinal axis of the anchor shaft, is between 0.25 and 5 mm, and a greatest lateral dimension of the open shape, measured perpendicular to the central longitudinal axis, is between 4 and 20 mm.

Inventive concept 38. The apparatus according to inventive concept 34, wherein, when the tissue anchor is unconstrained by the deployment tool:

a greatest longitudinal dimension of the open shape, measured in parallel to a central longitudinal axis of the anchor shaft, is between 5 and 15 mm, and a greatest lateral dimension of the open shape, measured perpendicular to the central longitudinal axis, is between 4 and 20 mm.

Inventive concept 39. The apparatus according to any one of inventive concepts 1-23, wherein, extending along at least 90% of a total length of the wire, the wire has a greatest major dimension and a greatest minor dimension perpendicular to the greatest major dimension, and wherein the greatest major dimension equals at least 150% of the greatest minor dimension.

Inventive concept 40. The apparatus according to inventive concept 39, wherein the wire is shaped so as to define an opening within 7 mm of a proximal end of the wire, and wherein the proximal portion of the flexible elongate tension member passes through the opening.

Inventive concept 41. The apparatus according to inventive concept 39, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 42. The apparatus according to inventive concept 39, wherein, when the tissue anchor is unconstrained by the deployment tool:

a greatest longitudinal dimension of the open shape, measured in parallel to a central longitudinal axis of the anchor shaft, is between 0.25 and 5 mm, and a greatest lateral dimension of the open shape, measured perpendicular to the central longitudinal axis, is between 4 and 20 mm.

Inventive concept 43. The apparatus according to inventive concept 39, wherein, when the tissue anchor is unconstrained by the deployment tool:

a greatest longitudinal dimension of the open shape, measured in parallel to a central longitudinal axis of the anchor shaft, is between 5 and 15 mm, and a greatest lateral dimension of the open shape, measured perpendicular to the central longitudinal axis, is between 4 and 20 mm.

Inventive concept 44. The apparatus according to any one of inventive concepts 1-23, wherein at a plurality of locations along the wire, a cross section of the wire, taken perpendicular to a longitudinal axis of the wire, has a shape that has at least one straight side.

Inventive concept 45. The apparatus according to inventive concept 44, wherein the at least one straight side has a length of at least 3 mm.

Inventive concept 46. The apparatus according to any one of inventive concepts 1-23, wherein the wire is shaped so as to define a proximal opening within 7 mm of a proximal end of the wire, and wherein the proximal portion of the flexible elongate tension member passes through the proximal opening.

Inventive concept 47. The apparatus according to any one of inventive concepts 1-23, wherein the longitudinal segment of the proximal portion of the flexible elongate tension member is coupled in sliding communication with the at least a portion of the anchor shaft when the tissue anchor is unconstrained by the deployment tool.

Inventive concept 48. The apparatus according to inventive concept 47, wherein the tissue anchor includes one or more annular elements, which are disposed around the at least a portion of the anchor shaft, and couple the flexible elongate tension member in the sliding communication with the at least a portion of the anchor shaft when the tissue anchor is unconstrained by the deployment tool.

Inventive concept 49. The apparatus according to any one of inventive concepts 1-23, wherein a proximally-facing surface defined by the tissue-coupling element is concave when the tissue anchor is unconstrained by the deployment tool.

Inventive concept 50. The apparatus according to any one of inventive concepts 1-23, wherein a proximally-facing surface defined by the tissue-coupling element is convex when the tissue anchor is unconstrained by the deployment tool.

Inventive concept 51. The apparatus according to any one of inventive concepts 1-23, wherein the apparatus further includes one or more tethers, which are fixed to the flexible elongate tension member.

Inventive concept 52. The apparatus according to any one of inventive concepts 1-23, wherein the tissue anchor is a first tissue anchor, and wherein the apparatus further includes:

a second tissue anchor, which is separate and distinct from the first tissue anchor; and one or more tethers, which are configured to couple (a) the flexible elongate tension member to (h) the second tissue anchor.

Inventive concept 53. The apparatus according to inventive concept 52, wherein the one or more tethers are fixed to (a) the flexible elongate tension member and (b) the second tissue anchor.

Inventive concept 54. The apparatus according to inventive concept 52, wherein the one or more tethers are (a) fixed to the second tissue anchor and (b) not fixed to the anchor shaft of the first tissue anchor.

Inventive concept 55. The apparatus according to inventive concept 52, wherein the second tissue anchor includes a helical tissue-coupling element.

Inventive concept 56. The apparatus according to inventive concept 52, wherein the second tissue anchor includes a stent.

Inventive concept 57. The apparatus according to any one of inventive concepts 1-23, wherein the tissue anchor is a first tissue anchor, and wherein the apparatus further includes a second tissue anchor, which is separate and distinct from the first tissue anchor, and wherein the flexible elongate tension member is coupled to the second tissue anchor.

Inventive concept 58. The apparatus according to inventive concept 57, wherein the flexible elongate tension member is fixed to the second tissue anchor.

Inventive concept 59. The apparatus according to any one of inventive concepts 1-23, wherein, when the tissue-coupling element is constrained by the deployment tool, a longitudinal portion of the flexible elongate tension member runs alongside a portion of the wire.

Inventive concept 60. The apparatus according to any one of inventive concepts 1-23, wherein application to the flexible elongate tension member of a distally-directed force of at least 1 N while the tissue anchor is unconstrained draws the distal end of the open shape toward the distal end of the anchor shaft.

Inventive concept 61. The apparatus according to any one of inventive concepts 1-23, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 62. The apparatus according to inventive concept 61, wherein at least 95% of the area of the projection of the tissue-coupling element on the plane would fall within the first angle.

Inventive concept 63. The apparatus according to inventive concept 61, wherein at least 80% of the area of the projection of the tissue-coupling element on the plane would fall within a third angle of 150 degrees in the plane having the vertex at the central longitudinal axis.

Inventive concept 64. The apparatus according to any one of inventive concepts 1-23, wherein the tissue anchor includes an anchor head connected to a proximal portion of the anchor shaft, wherein the anchor head is shaped so as to define a passage in which the proximal portion of the flexible elongate tension member is slidably disposed, wherein the flexible elongate tension member includes a locking stopper, which is axially fixed to the flexible elongate tension member, and wherein the locking stopper and the passage are sized and shaped such that the size and shape of the passage prevent proximal movement of the locking stopper past the passage.

Inventive concept 65. The apparatus according to any one of inventive concepts 1-23, wherein the tissue-coupling element further includes a tip, which is fixed to a distal end of the wire, and has, at a widest longitudinal site along the tip, a greatest tip outer cross-sectional area that equals at least 150% of an average wire cross-sectional area of the wire.

Inventive concept 66. The apparatus according to inventive concept 65, wherein the distal site is on the tip.

Inventive concept 67. The apparatus according to inventive concept 65, wherein the tip is shaped so as to define a guidewire lumen therethrough.

Inventive concept 68. The apparatus according to inventive concept 65, further including the deployment tool, which includes a deployment shaft shaped so as to define a deployment-shaft lumen, wherein the deployment shaft has a deployment-shaft outer cross-sectional area which equals between 90% and 110% of the greatest tip outer cross-sectional area, and wherein the tip is shaped so as to removably engage a distal end of the deployment shaft.

There is further provided, in accordance with an inventive concept 69 of the present invention, apparatus for delivery in a constrained state within a deployment tool, the apparatus including a tissue anchor, which includes:

an anchor shaft having a central longitudinal axis;

a tissue-coupling element, which (a) extends from a distal end of the anchor shaft, and (b) includes a wire, wherein when the tissue anchor is unconstrained by the deployment tool: (a) the wire is shaped as an open shape, and (b) if the tissue-coupling element were to be projected onto a plane that is perpendicular to the central longitudinal axis, the open shape would surround between 170 and 355 degrees of a point in the plane; and a flexible elongate tension member, which includes (a) a distal portion that is fixed to a site on the wire, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses at least a portion of the open shape when the tissue anchor is unconstrained by the deployment tool, wherein the tissue anchor is configured to allow relative axial motion between the at least a portion of the anchor shaft and the longitudinal segment of the proximal portion of the flexible elongate tension member when the tissue anchor is unconstrained by the deployment tool.

Inventive concept 70. The apparatus according to inventive concept 69, wherein the tissue anchor includes an anchor head connected to a proximal portion of the anchor shaft, wherein the anchor head is shaped so as to define a passage in which the proximal portion of the flexible elongate tension member is slidably disposed, wherein the flexible elongate tension member includes a locking stopper, which is axially fixed to the proximal or the crossing portion of the flexible elongate tension member, and wherein the locking stopper and the passage are sized and shaped such that the size and shape of the passage prevent proximal movement of the locking stopper past the passage.

Inventive concept 71. The apparatus according to inventive concept 69, wherein the open shape is shaped as a portion of a circle or a portion of an ellipse when the tissue anchor is unconstrained by the deployment tool.

Inventive concept 72. The apparatus according to inventive concept 69, wherein the point falls on a projection onto the plane of a line segment that terminates at (a) the site on the wire and (b) a proximal end of the wire when the tissue anchor is unconstrained by the deployment tool.

Inventive concept 73. The apparatus according to inventive concept 69, wherein the site on the wire is at a distal end of the wire.

Inventive concept 74. The apparatus according to inventive concept 73, wherein the wire is shaped so as to define a channel, through which a portion of the flexible elongate tension member passes and exits the wire at the distal end of the wire.

Inventive concept 75. The apparatus according to inventive concept 69, wherein a radius of the flexible elongate tension member is less than a radius of the wire.

Inventive concept 76. The apparatus according to inventive concept 75, wherein the radius of the flexible elongate tension member is less than 50% of the radius of the wire.

Inventive concept 77. The apparatus according to any one of inventive concepts 69-76, wherein, when the tissue anchor is unconstrained by the deployment tool, (a) a line segment that terminates at (i) the site on the wire and (ii) a proximal end of the tissue-coupling element may have a total length that equals a percentage of (b) a total length of the tissue-coupling element, measured the along tissue-coupling element, the percentage between 25% and 75%.

Inventive concept 78. The apparatus according to any one of inventive concepts 69-76, wherein, when the tissue anchor is unconstrained by the deployment tool:

a greatest longitudinal dimension of the open shape, measured in parallel to a central longitudinal axis of the anchor shaft, is between 0.25 and 5 mm, and a greatest lateral dimension of the open shape, measured perpendicular to the central longitudinal axis, is between 4 and 20 mm.

There is still further provided, in accordance with an inventive concept 79 of the present invention, apparatus for delivery in a constrained state within a deployment tool, the apparatus including a tissue anchor, which includes:

an anchor shaft;

a tissue-coupling element, which (a) extends from a distal end of the anchor shaft, and (b) includes a wire, which is shaped as an open loop having more than one turn when the tissue anchor is unconstrained by the deployment tool; and a flexible elongate tension member, which includes (a) a distal portion that is fixed to a site on the open loop, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses at least a portion of the open loop when the tissue anchor is unconstrained by the deployment tool, wherein the tissue anchor is configured to allow relative axial motion between the at least a portion of the anchor shaft and the longitudinal segment of the proximal portion of the flexible elongate tension member when the tissue anchor is unconstrained by the deployment tool.

Inventive concept 80. The apparatus according to inventive concept 79, wherein the open loop is shaped as a spiral when the tissue anchor is unconstrained by the deployment tool.

Inventive concept 81. The apparatus according to inventive concept 80, wherein the spiral is shaped as a three-dimensional spiral when the tissue anchor is unconstrained by the deployment tool.

Inventive concept 82. The apparatus according to inventive concept 80, wherein the spiral is shaped as an elliptical spiral when the tissue anchor is unconstrained by the deployment tool.

Inventive concept 83. The apparatus according to inventive concept 79, wherein the open loop is shaped as a three-dimensional open loop when the tissue anchor is unconstrained by the deployment tool.

Inventive concept 84. The apparatus according to inventive concept 83, wherein, when the tissue anchor is unconstrained by the deployment tool:

a greatest longitudinal dimension of the three-dimensional open loop, measured in parallel to a central longitudinal axis of the anchor shaft, is between 1 and 5 mm, and a greatest lateral dimension of the three-dimensional open loop, measured perpendicular to the central longitudinal axis, is between 4 and 20 mm.

Inventive concept 85. The apparatus according to inventive concept 79, wherein the site is on an outermost turn of the open loop when the tissue anchor is unconstrained by the deployment tool.

Inventive concept 86. The apparatus according to inventive concept 79, wherein the site is on a second-to-outermost turn of the open loop when the tissue anchor is unconstrained by the deployment tool.

Inventive concept 87. The apparatus according to inventive concept 79, wherein a radius of the flexible elongate tension member is less than a radius of the wire.

Inventive concept 88. The apparatus according to inventive concept 87, wherein the radius of the flexible elongate tension member is less than 50% of the radius of the wire.

Inventive concept 89. The apparatus according to inventive concept 79, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the anchor shaft, an angle between (a) the flexible elongate tension member and (b) a tangent to the open loop at the site would be between 70 and 90 degrees.

Inventive concept 90. The apparatus according to inventive concept 79, wherein, when the tissue anchor is unconstrained by the deployment tool:

the open loop is shaped so as to define an outermost turn and a second-to-outermost at least partial turn, and the outermost turn at least partially overlaps the second-to-outermost at least partial turn.

Inventive concept 91. The apparatus according to inventive concept 79, wherein, when the tissue anchor is unconstrained by the deployment tool, the open loop is shaped so as to define one or more curved segments and one or more straight segments.

Inventive concept 92. The apparatus according to inventive concept 91, wherein, when the tissue anchor is unconstrained by the deployment tool, the open loop is shaped so as to define the one or more curved segments and two or more straight segments.

Inventive concept 93. The apparatus according to inventive concept 79, wherein, when the tissue anchor is unconstrained by the deployment tool:

the open loop has a greatest lateral dimension, measured perpendicular to a central longitudinal axis of the anchor shaft, and a distance between (a) a radially-outer end of the open loop and (b) a radially-inner-most point of the open loop, measured perpendicular to the central longitudinal axis, is equal to at least 30% of the greatest lateral dimension.

Inventive concept 94. The apparatus according to inventive concept 93, wherein a ratio of the greatest longitudinal dimension and the greatest lateral dimension is between 1:2 and 1:18 when the tissue anchor is unconstrained by the deployment tool.

Inventive concept 95. The apparatus according to inventive concept 79, wherein the anchor shaft includes a sealing element.

Inventive concept 96. The apparatus according to inventive concept 79, wherein the anchor shaft has a central longitudinal axis that is straight when the tissue anchor is unconstrained by the deployment tool.

Inventive concept 97. The apparatus according to inventive concept 79, wherein the anchor shaft and the tissue-coupling element are integral to one another.

Inventive concept 98. The apparatus according to inventive concept 79, wherein a cross-sectional area of the wire is at least 0.09 mm2.

Inventive concept 99. The apparatus according to inventive concept 98, wherein the cross-sectional area of the wire is no more than 2.9 mm2.

Inventive concept 100. The apparatus according to inventive concept 79, wherein the flexible elongate tension member includes Nitinol.

Inventive concept 101. The apparatus according to any one of inventive concepts 79-100, wherein the tissue anchor includes an anchor head connected to a proximal portion of the anchor shaft, and wherein, when the tissue anchor is unconstrained by the deployment tool:
  the anchor shaft has a central longitudinal axis,
  the anchor head is coaxial with the central longitudinal axis, and
  the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (h) the area would partially overlap, at least 3 mm from the vertex, both rays of a second angle of between 45 and 180 degrees in the plane having the vertex at the central longitudinal axis.

Inventive concept 102. The apparatus according to inventive concept 101, wherein at least 95% of the area of the projection of the tissue-coupling element on the plane would fall within the first angle.

Inventive concept 103. The apparatus according to inventive concept 101, wherein at least 80% of the area of the projection of the tissue-coupling element on the plane would fall within a third angle of 150 degrees in the plane having the vertex at the central longitudinal axis.

Inventive concept 104. The apparatus according to any one of inventive concepts 79-100,
  wherein the tissue anchor includes an anchor head connected to a proximal portion of the anchor shaft,
  wherein the anchor head is shaped so as to define a passage in which the proximal portion of the flexible elongate tension member is slidably disposed,
  wherein the flexible elongate tension member includes a locking stopper, which is axially fixed to the proximal or the crossing portion of the flexible elongate tension member, and
  wherein the locking stopper and the passage are sized and shaped such that the size and shape of the passage prevent proximal movement of the locking stopper past the passage.

Inventive concept 105. The apparatus according to inventive concept 104, wherein the locking stopper is axially fixed to the proximal or the crossing portion of the flexible elongate tension member at a distance of between 7 and 22 mm from the site on the open loop.

Inventive concept 106. The apparatus according to inventive concept 104, wherein, if the tissue-coupling element were straightened in an elongated configuration, the locking stopper would be a distance of between 7 and 12 mm from the passage.

Inventive concept 107. The apparatus according to any one of inventive concepts 79-100, wherein the site on the open loop is a first site on the open loop, and wherein, when the tissue anchor is unconstrained by the deployment tool and the flexible elongate tension member is tensioned straight:
  the open loop surrounds a center point,
  the wire extends from the distal end of the anchor shaft at a second site on the open loop, and
  if the tissue-coupling element and the flexible elongate tension member were to be projected onto a plane that is perpendicular to a central longitudinal axis of the anchor shaft, an angle between the first and the second sites, having a vertex at the center point, would be between 130 and 180 degrees.

Inventive concept 108. The apparatus according to inventive concept 107, wherein the angle is between 150 and 180 degrees.

Inventive concept 109. The apparatus according to inventive concept 108, wherein the angle is between 170 and 180 degrees.

Inventive concept 110. The apparatus according to inventive concept 107, the second site is at a radially-outer end of the open loop when the tissue anchor is unconstrained by the deployment tool.

Inventive concept 111. The apparatus according to any one of inventive concepts 79-100, wherein, when the tissue anchor is unconstrained by the deployment tool:
  the open loop surrounds a center point, and
  (a) a site distance between the site and the distal end of the anchor shaft is greater than (b) a center-point distance between the center point and the distal end of the anchor shaft, when the tissue anchor is unconstrained by the deployment tool.

Inventive concept 112. The apparatus according to inventive concept 111, wherein the site distance equals at least 150% of the center-point distance, when the tissue anchor is unconstrained by the deployment tool.

Inventive concept 113. The apparatus according to inventive concept 112, wherein the site distance equals at least 175% of the center-point distance when the tissue anchor is unconstrained by the deployment tool.

Inventive concept 114. The apparatus according to any one of inventive concepts 79-100, wherein the longitudinal segment of the proximal portion of the flexible elongate tension member is coupled in sliding communication with the at least a portion of the anchor shaft when the tissue anchor is unconstrained by the deployment tool.

Inventive concept 115. The apparatus according to inventive concept 114, wherein the tissue anchor includes one or more annular elements, which are disposed around the at least a portion of the anchor shaft, and couple the flexible elongate tension member in the sliding communication with the at least a portion of the anchor shaft when the tissue anchor is unconstrained by the deployment tool.

Inventive concept 116. The apparatus according to any one of inventive concepts 79-100, wherein the flexible elongate tension member is not fixed to any portion of the open loop beyond 2 mm from the site on the open loop, measured when the tissue anchor is unconstrained by the deployment tool.

Inventive concept 117. The apparatus according to any one of inventive concepts 79-100, wherein, when the tissue anchor is unconstrained by the deployment tool:
  the open loop has a greatest lateral dimension, measured perpendicular to a central longitudinal axis of the anchor shaft, and the flexible elongate tension member is not fixed to any portion of the open loop beyond a distance from the site on the open loop, wherein the distance equals 30% of the greatest lateral dimension.

Inventive concept 118. The apparatus according to any one of inventive concepts 79-100, wherein the flexible elongate tension member is fixed to the open loop only at the site on the open loop.

Inventive concept 119. The apparatus according to any one of inventive concepts 79-100, wherein, when the tissue anchor is unconstrained by the deployment tool:
the open loop has a greatest lateral dimension, measured perpendicular to a central longitudinal axis of the anchor shaft, and
the at least a portion of the open loop crossed by the crossing portion has a length that equals at least 50% of the greatest lateral dimension.

Inventive concept 120. The apparatus according to inventive concept 119, wherein the length of the at least a portion of the open loop crossed by the crossing portion equals at least 75% of the greatest lateral dimension when the tissue anchor is unconstrained by the deployment tool.

Inventive concept 121. The apparatus according to inventive concept 120, wherein the length of the at least a portion of the open loop crossed by the crossing portion equals at least 90% of the greatest lateral dimension when the tissue anchor is unconstrained by the deployment tool.

Inventive concept 122. The apparatus according to any one of inventive concepts 79-100, wherein the wire extends from the distal end of the anchor shaft at a radially-outer end of the open loop when the tissue anchor is unconstrained by the deployment tool.

Inventive concept 123. The apparatus according to inventive concept 122, wherein, when the tissue anchor is unconstrained by the deployment tool, the open loop surrounds a center point, and the wire intersects the center point.

Inventive concept 124. The apparatus according to inventive concept 122, wherein, when the tissue anchor is unconstrained by the deployment tool, the open loop surrounds a center point, and the wire does not intersect the center point.

Inventive concept 125. The apparatus according to any one of inventive concepts 79-100, wherein the wire extends from the distal end of the anchor shaft at a radially-inner end of the open loop when the tissue anchor is unconstrained by the deployment tool.

Inventive concept 126. The apparatus according to any one of inventive concepts 79-100, wherein a proximally-facing surface defined by the tissue-coupling element is concave when the tissue anchor is unconstrained by the deployment tool.

Inventive concept 127. The apparatus according to any one of inventive concepts 79-100, wherein a proximally-facing surface defined by the tissue-coupling element is convex when the tissue anchor is unconstrained by the deployment tool.

Inventive concept 128. The apparatus according to any one of inventive concepts 79-100, wherein the apparatus further includes one or more tethers, which are fixed to the flexible elongate tension member.

Inventive concept 129. The apparatus according to any one of inventive concepts 79-100,
wherein the tissue anchor is a first tissue anchor, and
wherein the apparatus further includes:
a second tissue anchor, which is separate and distinct from the first tissue anchor; and
one or more tethers, which are configured to couple (a) the flexible elongate tension member to (b) the second tissue anchor.

Inventive concept 130. The apparatus according to inventive concept 129, wherein the one or more tethers are fixed to (a) the flexible elongate tension member and (b) the second tissue anchor.

Inventive concept 131. The apparatus according to inventive concept 129, wherein the one or more tethers are (a) fixed to the second tissue anchor and (b) not fixed to the anchor shaft of the first tissue anchor.

Inventive concept 132. The apparatus according to inventive concept 129, wherein the second tissue anchor includes a helical tissue-coupling element.

Inventive concept 133. The apparatus according to inventive concept 129, wherein the second tissue anchor includes a stent.

Inventive concept 134. The apparatus according to any one of inventive concepts 79-100,
wherein the tissue anchor is a first tissue anchor, and
wherein the apparatus further includes a second tissue anchor, which is separate and distinct from the first tissue anchor, and
wherein the flexible elongate tension member is coupled to the second tissue anchor.

Inventive concept 135. The apparatus according to inventive concept 134, wherein the flexible elongate tension member is fixed to the second tissue anchor.

Inventive concept 136. The apparatus according to any one of inventive concepts 79-100, wherein, when the tissue-coupling element is constrained by the deployment tool, a longitudinal portion of the flexible elongate tension member runs alongside a portion of the wire.

Inventive concept 137. The apparatus according to any one of inventive concepts 79-100, for use with a guidewire,
wherein the tissue anchor includes an anchor head connected to a proximal portion of the anchor shaft,
wherein the anchor head is shaped so as to define:
a first passage, in which the proximal portion of the flexible elongate tension member is slidably disposed,
a second passage, in which a proximal portion of the wire of the tissue-coupling element is fixedly disposed, and
a third passage, sized for slidable passage there through of the guidewire, and
wherein the first, the second, and the third passages have respective, different central longitudinal axes.

Inventive concept 138. The apparatus according to inventive concept 137, wherein the third passage has an inner diameter of between 0.25 and 0.75 mm.

Inventive concept 139. The apparatus according to inventive concept 137, wherein a proximal end of the second passage is closed.

Inventive concept 140. The apparatus according to any one of inventive concepts 79-100, wherein the wire is shaped so as to define a channel, which has a lateral opening at the site, and wherein the distal portion of the flexible elongate tension member passes through the lateral opening.

Inventive concept 141. The apparatus according to inventive concept 140, wherein the distal portion of the flexible elongate tension member passes through the lateral opening and extends distally through at least a portion of the channel.

Inventive concept 142. The apparatus according to inventive concept 141, wherein the distal portion of the flexible elongate tension member extends distally through the at least a portion of the channel to at least within 7 mm of a distal end of the wire.

Inventive concept 143. The apparatus according to inventive concept 141, wherein the distal portion of the flexible elongate tension member extends distally through the at least a portion of the channel to the distal end of the wire.

Inventive concept 144. The apparatus according to any one of inventive concepts 79-100, wherein the wire is shaped so as to define first and second major opposing surfaces connected by first and second minor opposing surfaces, wherein the first and the second major opposing surfaces and the first and the second minor opposing surfaces extend along at least 90% of a total length of the wire, and wherein a total surface area of the first minor opposing surface is less than 10% of a total surface area of the major opposing surface.

Inventive concept 145. The apparatus according to inventive concept 144, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 146. The apparatus according to any one of inventive concepts 79-100, wherein, extending along at least 90% of a total length of the wire, the wire has a greatest major dimension and a greatest minor dimension perpendicular to the greatest major dimension, and wherein the greatest major dimension equals at least 150% of the greatest minor dimension.

Inventive concept 147. The apparatus according to inventive concept 146, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 148. The apparatus according to any one of inventive concepts 79-100, wherein at a plurality of locations along the wire, a cross section of the wire, taken perpendicular to a longitudinal axis of the wire, has a shape that has at least one straight side.

Inventive concept 149. The apparatus according to inventive concept 148, wherein the at least one straight side has a length of at least 3 mm.

There is additionally provided, in accordance with an inventive concept 150 of the present invention, apparatus for delivery in a constrained state within a deployment tool, the apparatus including a tissue anchor, which includes:

an anchor shaft;

a tissue-coupling element, which (a) extends from a distal end of the anchor shaft, (b) includes a wire and a tip, which is fixed to a distal end of the wire, and has, at a widest longitudinal site along the tip, a greatest tip outer cross-sectional area that equals at least 150% of an average wire cross-sectional area of the wire, and (c) is shaped as an open shape when the tissue anchor is unconstrained by the deployment tool; and a flexible elongate tension member, which includes (a) a distal portion that is fixed to a site on the open shape, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses at least a portion of the open shape when the tissue anchor is unconstrained by the deployment tool, wherein the tissue anchor is configured to allow relative axial motion between the at least a portion of the anchor shaft and the longitudinal segment of the proximal portion of the flexible elongate tension member when the tissue anchor is unconstrained by the deployment tool.

Inventive concept 151. The apparatus according to inventive concept 150, wherein the greatest tip outer cross-sectional area equals at least 200% of the average anchoring-element outer cross-sectional area.

Inventive concept 152. The apparatus according to inventive concept 150, wherein the greatest tip outer cross-sectional area is greater than 1 mm2.

Inventive concept 153. The apparatus according to inventive concept 150, wherein the tip includes a frustoconical portion.

Inventive concept 154. The apparatus according to inventive concept 150, wherein the tip is shaped so as to define a guidewire lumen therethrough.

Inventive concept 155. The apparatus according to inventive concept 154, wherein the tip has a central longitudinal axis, which (a) passes through a distal end-opening of the guidewire lumen, and (b) does not pass through a proximal end-opening of the guidewire lumen.

Inventive concept 156. The apparatus according to inventive concept 155, wherein a center of the distal end-opening of the guidewire lumen is disposed within 1 mm of the central longitudinal axis of the tip.

Inventive concept 157. The apparatus according to inventive concept 155, wherein the central longitudinal axis of the tip passes through the distal end of the wire.

Inventive concept 158. The apparatus according to inventive concept 150, wherein the distal portion of the flexible elongate tension member at least partially runs along the open shape between the site and the tip.

Inventive concept 159. The apparatus according to inventive concept 158, wherein the distal portion of the flexible elongate tension member, at one or more locations along the distal portion, is fixed to the tip.

Inventive concept 160. The apparatus according to inventive concept 159, wherein the tip is shaped so as to define a tension-member lumen therethrough, and wherein the distal portion of the flexible elongate tension member passes through at least a portion of the tension-member lumen.

Inventive concept 161. The apparatus according to inventive concept 150, further including the deployment tool, which includes a deployment shaft shaped so as to define a deployment-shaft lumen, wherein the deployment shaft has a deployment-shaft outer cross-sectional area which equals between 90% and 110% of the greatest tip outer cross-sectional area, and wherein the tip is shaped so as to removably engage a distal end of the deployment shaft.

Inventive concept 162. The apparatus according to inventive concept 161, wherein the tip is shaped so as to define a guidewire lumen therethrough, wherein the deployment shaft is shaped so as to define a guidewire opening through a wall of the deployment shaft, and wherein the guidewire opening reaches the distal end of the deployment shaft.

Inventive concept 163. The apparatus according to inventive concept 150, for use with a guidewire,
wherein the tissue anchor includes an anchor head connected to a proximal portion of the anchor shaft,
wherein the anchor head is shaped so as to define:
a first passage, in which the proximal portion of the flexible elongate tension member is slidably disposed,
a second passage, in which a proximal portion of the wire of the tissue-coupling element is fixedly disposed, and
a third passage, sized for slidable passage therethrough of the guidewire, and
wherein the first, the second, and the third passages have respective, different central longitudinal axes.

Inventive concept 164. The apparatus according to inventive concept 163, wherein the third passage has an inner diameter of between 0.25 and 0.75 mm.

Inventive concept 165. The apparatus according to inventive concept 163, wherein a proximal end of the second passage is closed.

Inventive concept 166. The apparatus according to inventive concept 150, wherein the open shape is an open loop having more than one turn when the tissue anchor is unconstrained by the deployment tool.

Inventive concept 167. The apparatus according to inventive concept 166, wherein the open loop is shaped as a spiral when the tissue anchor is unconstrained by the deployment tool.

Inventive concept 168. The apparatus according to inventive concept 167, wherein the spiral is shaped as a three-dimensional spiral when the tissue anchor is unconstrained by the deployment tool.

Inventive concept 169. The apparatus according to inventive concept 167, wherein the spiral is shaped as an elliptical spiral when the tissue anchor is unconstrained by the deployment tool.

Inventive concept 170. The apparatus according to inventive concept 166, wherein the open loop is shaped as a three-dimensional open loop when the tissue anchor is unconstrained by the deployment tool.

Inventive concept 171. The apparatus according to inventive concept 170, wherein, when the tissue anchor is unconstrained by the deployment tool:
a greatest longitudinal dimension of the three-dimensional open loop, measured in parallel to a central longitudinal axis of the anchor shaft, is between 1 and 5 mm, and
a greatest lateral dimension of the three-dimensional open loop, measured perpendicular to the central longitudinal axis, is between 4 and 20 mm.

Inventive concept 172. The apparatus according to inventive concept 166, wherein the site is on an outermost turn of the open loop when the tissue anchor is unconstrained by the deployment tool.

Inventive concept 173. The apparatus according to inventive concept 166, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the anchor shaft, an angle between (a) the flexible elongate tension member and (b) a tangent to the open loop at the site would be between 70 and 90 degrees.

Inventive concept 174. The apparatus according to inventive concept 166, wherein, when the tissue anchor is unconstrained by the deployment tool:
the open loop is shaped so as to define an outermost turn and a second-to-outermost at least partial turn, and
the outermost turn at least partially overlaps the second-to-outermost at least partial turn.

Inventive concept 175. The apparatus according to inventive concept 166, wherein the site on the open loop is a first site on the open loop, and wherein, when the tissue anchor is unconstrained by the deployment tool and the flexible elongate tension member is tensioned straight:
the open loop surrounds a center point,
the wire extends from the distal end of the anchor shaft at a second site on the open loop, and
if the tissue-coupling element and the flexible elongate tension member were to be projected onto a plane that is perpendicular to a central longitudinal axis of the anchor shaft, an angle between the first and the second sites, having a vertex at the center point, would be between 130 and 180 degrees.

Inventive concept 176. The apparatus according to inventive concept 175, wherein the second site is at a radially-outer end of the open loop when the tissue anchor is unconstrained by the deployment tool.

Inventive concept 177. The apparatus according to inventive concept 166, wherein the wire extends from the distal end of the anchor shaft at a radially-outer end of the open loop when the tissue anchor is unconstrained by the deployment tool.

Inventive concept 178. The apparatus according to inventive concept 166, wherein the wire extends from the distal end of the anchor shaft at a radially-inner end of the open loop when the tissue anchor is unconstrained by the deployment tool.

Inventive concept 179. The apparatus according to inventive concept 150, wherein a radius of the flexible elongate tension member is less than a radius of the wire.

Inventive concept 180. The apparatus according to inventive concept 179, wherein the radius of the flexible elongate tension member is less than 50% of the radius of the wire.

Inventive concept 181. The apparatus according to inventive concept 150, wherein the anchor shaft has a central longitudinal axis that is straight when the tissue anchor is unconstrained by the deployment tool.

Inventive concept 182. The apparatus according to inventive concept 150, wherein the anchor shaft and the tissue-coupling element are integral to one another.

Inventive concept 183. The apparatus according to any one of inventive concepts 150-182, wherein the tissue anchor includes an anchor head connected to a proximal portion of the anchor shaft, and wherein, when the tissue anchor is unconstrained by the deployment tool:
the anchor shaft has a central longitudinal axis,
the anchor head is coaxial with the central longitudinal axis, and
the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 184. The apparatus according to inventive concept 183, wherein at least 95% of the area of the projection of the tissue-coupling element on the plane would fall within the first angle.

Inventive concept 185. The apparatus according to inventive concept 183, wherein at least 80% of the area of the projection of the tissue-coupling element on the plane would fall within a third angle of 150 degrees in the plane having the vertex at the central longitudinal axis.

Inventive concept 186. The apparatus according to any one of inventive concepts 150-182,
wherein the tissue anchor includes an anchor head connected to a proximal portion of the anchor shaft,
wherein the anchor head is shaped so as to define a passage in which the proximal portion of the flexible elongate tension member is slidably disposed,
wherein the flexible elongate tension member includes a locking stopper, which is axially fixed to the proximal or the crossing portion of the flexible elongate tension member, and
wherein the locking stopper and the passage are sized and shaped such that the size and shape of the passage prevent proximal movement of the locking stopper past the passage.

Inventive concept 187. The apparatus according to inventive concept 186, wherein the locking stopper is axially fixed to the proximal or the crossing portion of the flexible elongate tension member at a distance of between 7 and 22 mm from the site on the open shape.

Inventive concept 188. The apparatus according to inventive concept 186, wherein, if the tissue-coupling element were straightened in an elongated configuration, the locking stopper would be a distance of between 7 and 12 mm from the passage.

Inventive concept 189. The apparatus according to any one of inventive concepts 150-182, wherein the longitudinal segment of the proximal portion of the flexible elongate tension member is coupled in sliding communication with the at least a portion of the anchor shaft when the tissue anchor is unconstrained by the deployment tool.

Inventive concept 190. The apparatus according to inventive concept 189, wherein the tissue anchor includes one or more annular elements, which are disposed around the at least a portion of the anchor shaft, and couple the flexible elongate tension member in the sliding communication with the at least a portion of the anchor shaft when the tissue anchor is unconstrained by the deployment tool.

Inventive concept 191. The apparatus according to any one of inventive concepts 150-182, wherein the apparatus further includes one or more tethers, which are fixed to the flexible elongate tension member.

Inventive concept 192. The apparatus according to any one of inventive concepts 150-182,
wherein the tissue anchor is a first tissue anchor, and
wherein the apparatus further includes:
a second tissue anchor, which is separate and distinct from the first tissue anchor; and
one or more tethers, which are configured to couple (a) the flexible elongate tension member to (b) the second tissue anchor.

Inventive concept 193. The apparatus according to inventive concept 192, wherein the one or more tethers are fixed to (a) the flexible elongate tension member and (b) the second tissue anchor.

Inventive concept 194. The apparatus according to inventive concept 192, wherein the one or more tethers are (a) fixed to the second tissue anchor and (b) not fixed to the anchor shaft of the first tissue anchor.

Inventive concept 195. The apparatus according to inventive concept 192, wherein the second tissue anchor includes a helical tissue-coupling element.

Inventive concept 196. The apparatus according to inventive concept 192, wherein the second tissue anchor includes a stent.

Inventive concept 197. The apparatus according to any one of inventive concepts 150-182,
wherein the tissue anchor is a first tissue anchor, and
wherein the apparatus further includes a second tissue anchor, which is separate and distinct from the first tissue anchor, and
wherein the flexible elongate tension member is coupled to the second tissue anchor.

Inventive concept 198. The apparatus according to inventive concept 197, wherein the flexible elongate tension member is fixed to the second tissue anchor.

Inventive concept 199. The apparatus according to any one of inventive concepts 150-182, wherein, when the tissue-coupling element is constrained by the deployment tool, a longitudinal portion of the flexible elongate tension member runs alongside a portion of the wire.

Inventive concept 200. The apparatus according to any one of inventive concepts 150-182, wherein the wire is shaped so as to define a channel, which has a lateral opening at the site, and wherein the distal portion of the flexible elongate tension member passes through the lateral opening.

Inventive concept 201. The apparatus according to inventive concept 200, wherein the distal portion of the flexible elongate tension member passes through the lateral opening and extends distally through at least a portion of the channel.

Inventive concept 202. The apparatus according to inventive concept 201, wherein the distal portion of the flexible elongate tension member extends distally through the at least a portion of the channel to at least within 7 mm of a distal end of the wire.

Inventive concept 203. The apparatus according to inventive concept 201, wherein the distal portion of the flexible elongate tension member extends distally through the at least a portion of the channel to the distal end of the wire.

There is yet additionally provided, in accordance with an inventive concept 204 of the present invention, a method including:
providing a tissue anchor, which includes (a) an anchor shaft, (b) a tissue-coupling element, which (i) extends from a distal end of the anchor shaft, and (ii) includes a wire, and (c) a flexible elongate tension member;
introducing, during a transcatheter procedure, the tissue anchor into a cardiac chamber of a heart of a subject, while the tissue-coupling element is constrained by a deployment tool;
delivering the tissue-coupling element through a wall of the heart; and
at least partially releasing the tissue anchor from the deployment tool such that (a) the tissue-coupling element is unconstrained by the deployment tool, (b) the tissue-coupling element is shaped as an open shape; (c) the flexible elongate tension member extends from a distal site on the open shape, the distal site located within 7 mm of a distal end of the open shape, (d) a longitudinal segment of a proximal portion of the flexible elongate tension member runs alongside at least a portion of the anchor shaft, and (e) the tissue anchor allows relative axial motion between the at least a portion of the anchor shaft and the longitudinal segment of the proximal portion of the flexible elongate tension member.

Inventive concept 205. The method according to inventive concept 204, further including, after delivering the tissue-coupling element through the wall of the heart, at least partially compressing the open shape by applying tension to the flexible elongate tension member.

Inventive concept 206. The method according to inventive concept 204, further including, after delivering the tissue-coupling element through the wall of the heart, at least partially compressing the open shape and pulling the tissue-coupling element against an external surface of the heart, by applying tension to the flexible elongate tension member.

Inventive concept 207. The method according to inventive concept 204, further including, after delivering the tissue-coupling element through the wall of the heart, drawing the distal end of the open shape toward the distal end of the anchor shaft by applying, to the flexible elongate tension member, a distally-directed force of at least 1 N while the tissue anchor is unconstrained.

Inventive concept 208. The method according to inventive concept 204, further including, after delivering the tissue-coupling element through the wall of the heart:
  ascertaining whether the tissue-coupling element overlies a coronary blood vessel; and
  if the tissue-coupling element overlies the coronary blood vessel, rotating the tissue anchor until the tissue-coupling element no longer overlies the coronary blood vessel.

Inventive concept 209. The method according to inventive concept 204, further including, after delivering the tissue-coupling element through the wall of the heart:
  rotating the tissue anchor by rotating the anchor shaft; and
  bringing the tissue-coupling element into contact with an external surface of the heart by applying tension to the flexible elongate tension member.

Inventive concept 210. The method according to inventive concept 209, wherein bringing the tissue-coupling element into contact with the external surface of the heart includes bringing the tissue-coupling element into contact with the external surface of the heart without applying any tension to the anchor shaft.

Inventive concept 211. The method according to inventive concept 204, wherein a radius of the flexible elongate tension member is less than a radius of the wire.

Inventive concept 212. The method according to inventive concept 211, wherein the radius of the flexible elongate tension member is less than 50% of the radius of the wire.

Inventive concept 213. The method according to inventive concept 204, wherein the anchor shaft includes a sealing element.

Inventive concept 214. The method according to inventive concept 204, wherein the anchor shaft has a central longitudinal axis that is straight when the tissue anchor is unconstrained by the deployment tool.

Inventive concept 215. The method according to inventive concept 204, wherein the anchor shaft and the tissue-coupling element are integral to one another.

Inventive concept 216. The method according to inventive concept 204, wherein a cross-sectional area of the wire is at least 0.09 mm2.

Inventive concept 217. The method according to inventive concept 216, wherein the cross-sectional area of the wire is no more than 2.9 mm2.

Inventive concept 218. The method according to inventive concept 204, wherein the flexible elongate tension member includes Nitinol.

Inventive concept 219. The method according to inventive concept 204, wherein the open shape is an open loop having more than one turn when the tissue anchor is unconstrained by the deployment tool.

Inventive concept 220. The method according to inventive concept 219, wherein the open loop is shaped as a spiral when the tissue anchor is unconstrained by the deployment tool.

Inventive concept 221. The method according to inventive concept 220, wherein the spiral is shaped as a three-dimensional spiral when the tissue anchor is unconstrained by the deployment tool.

Inventive concept 222. The method according to inventive concept 220, wherein the spiral is shaped as an elliptical spiral when the tissue anchor is unconstrained by the deployment tool.

Inventive concept 223. The method according to inventive concept 219, wherein the open loop is shaped as a three-dimensional open loop when the tissue anchor is unconstrained by the deployment tool.

Inventive concept 224. The method according to inventive concept 223, wherein, when the tissue anchor is unconstrained by the deployment tool:
  a greatest longitudinal dimension of the three-dimensional open loop, measured in parallel to a central longitudinal axis of the anchor shaft, is between 1 and 5 mm, and
  a greatest lateral dimension of the three-dimensional open loop, measured perpendicular to the central longitudinal axis, is between 4 and 20 mm.

Inventive concept 225. The method according to inventive concept 219, wherein, when the tissue anchor is unconstrained by the deployment tool:
  the open loop is shaped so as to define an outermost turn and a second-to-outermost at least partial turn, and
  the outermost turn at least partially overlaps the second-to-outermost at least partial turn.

Inventive concept 226. The method according to inventive concept 219, wherein, when the tissue anchor is unconstrained by the deployment tool, the open loop is shaped so as to define one or more curved segments and one or more straight segments.

Inventive concept 227. The method according to inventive concept 226, wherein, when the tissue anchor is unconstrained by the deployment tool, the open loop is shaped so as to define the one or more curved segments and two or more straight segments.

Inventive concept 228. The method according to inventive concept 219, wherein, when the tissue anchor is unconstrained by the deployment tool:
  the open loop has a greatest lateral dimension, measured perpendicular to a central longitudinal axis of the anchor shaft, and
  a distance between (a) a radially-outer end of the open loop and (b) a radially-inner-most point of the open loop, measured perpendicular to the central longitudinal axis, is equal to at least 30% of the greatest lateral dimension.

Inventive concept 229. The method according to inventive concept 228, wherein a ratio of the greatest longitudinal dimension and the greatest lateral dimension is between 1:2 and 1:18 when the tissue anchor is unconstrained by the deployment tool.

Inventive concept 230. The method according to inventive concept 219, wherein the wire extends from the distal end of the anchor shaft at a radially-outer end of the open loop when the tissue anchor is unconstrained by the deployment tool.

Inventive concept 231. The method according to inventive concept 230, wherein, when the tissue anchor is unconstrained by the deployment tool, the open loop surrounds a center point, and the wire does not intersect the center point.

Inventive concept 232. The method according to inventive concept 219, wherein the wire extends from the distal end of the anchor shaft at a radially-inner end of the open loop when the tissue anchor is unconstrained by the deployment tool.

Inventive concept 233. The method according to inventive concept 204, wherein the distal site is located within 3 mm of the distal end of the open shape.

Inventive concept 234. The method according to inventive concept 233, wherein the distal site on the open shape is at the distal end of the open shape.

Inventive concept 235. The method according to inventive concept 204, wherein, when the tissue anchor is unconstrained by the deployment tool, (a) a line segment that terminates at (i) the distal site on the open shape and (ii) a proximal end of the tissue-coupling element may have a total length that equals a percentage of (b) a total length of the tissue-coupling element, measured the along tissue-coupling element, the percentage between 25% and 75%.

Inventive concept 236. The method according to inventive concept 204, wherein the wire is shaped so as to define a channel, and wherein the flexible elongate tension member passes through at least a portion of the channel.

Inventive concept 237. The method according to inventive concept 236, wherein the flexible elongate tension member passes through the entire channel, and the distal site on the open shape is a distal-end opening of the open shape.

Inventive concept 238. The method according to inventive concept 237, wherein a distal end portion of the flexible elongate tension member is fixed at or beyond a proximal end of the open shape.

Inventive concept 239. The method according to inventive concept 236, wherein the channel has a proximal lateral opening within 7 mm of a proximal end of the wire, and wherein the proximal portion of the flexible elongate tension member passes through the proximal lateral opening.

Inventive concept 240. The method according to inventive concept 239, wherein the proximal portion of the flexible elongate tension member passes through the proximal lateral opening and through a proximal-end opening of the channel.

Inventive concept 241. The method according to inventive concept 236, wherein the channel has a lateral opening at the site, and wherein the distal portion of the flexible elongate tension member passes through the lateral opening.

Inventive concept 242. The method according to inventive concept 236,
wherein the tissue-coupling element further includes a tip, which is fixed to a distal end of the wire, and has, at a widest longitudinal site along the tip, a greatest tip outer cross-sectional area that equals at least 150% of an average wire cross-sectional area of the wire,
wherein the distal site is on the tip,
wherein the tip is shaped so as to define an extension of the channel, and
wherein the flexible elongate tension member passes through a portion of the tip in the extension of the channel, and exits the tip at the distal site.

Inventive concept 243. The method according to inventive concept 204,
wherein the wire is shaped so as to define first and second major opposing surfaces connected by first and second minor opposing surfaces,
wherein the first and the second major opposing surfaces and the first and the second minor opposing surfaces extend along at least 90% of a total length of the wire, and
wherein a total surface area of the first minor opposing surface is less than 10% of a total surface area of the major opposing surface.

Inventive concept 244. The method according to inventive concept 243, wherein the wire is shaped so as to define an opening within 7 mm of a proximal end of the wire, and wherein the proximal portion of the flexible elongate tension member passes through the opening.

Inventive concept 245. The method according to inventive concept 243, wherein the tissue anchor includes an anchor head connected to a proximal portion of the anchor shaft, and wherein, when the tissue anchor is unconstrained by the deployment tool:
the anchor shaft has a central longitudinal axis,
the anchor head is coaxial with the central longitudinal axis, and
the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 246. The method according to inventive concept 243, wherein, when the tissue anchor is unconstrained by the deployment tool:
a greatest longitudinal dimension of the open shape, measured in parallel to a central longitudinal axis of the anchor shaft, is between 0.25 and 5 mm, and
a greatest lateral dimension of the open shape, measured perpendicular to the central longitudinal axis, is between 4 and 20 mm.

Inventive concept 247. The method according to inventive concept 243, wherein, when the tissue anchor is unconstrained by the deployment tool:
a greatest longitudinal dimension of the open shape, measured in parallel to a central longitudinal axis of the anchor shaft, is between 5 and 15 mm, and
a greatest lateral dimension of the open shape, measured perpendicular to the central longitudinal axis, is between 4 and 20 mm.

Inventive concept 248. The method according to inventive concept 204,
wherein, extending along at least 90% of a total length of the wire, the wire has a greatest major dimension and a greatest minor dimension perpendicular to the greatest major dimension, and
wherein the greatest major dimension equals at least 150% of the greatest minor dimension.

Inventive concept 249. The method according to inventive concept 248, wherein the wire is shaped so as to define an opening within 7 mm of a proximal end of the wire, and wherein the proximal portion of the flexible elongate tension member passes through the opening.

Inventive concept 250. The method according to inventive concept 248, wherein the tissue anchor includes an anchor head connected to a proximal portion of the anchor shaft, and wherein, when the tissue anchor is unconstrained by the deployment tool:
  the anchor shaft has a central longitudinal axis,
  the anchor head is coaxial with the central longitudinal axis, and
  the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 251. The method according to inventive concept 248, wherein, when the tissue anchor is unconstrained by the deployment tool:
  a greatest longitudinal dimension of the open shape, measured in parallel to a central longitudinal axis of the anchor shaft, is between 0.25 and 5 mm, and
  a greatest lateral dimension of the open shape, measured perpendicular to the central longitudinal axis, is between 4 and 20 mm.

Inventive concept 252. The method according to inventive concept 248, wherein, when the tissue anchor is unconstrained by the deployment tool:
  a greatest longitudinal dimension of the open shape, measured in parallel to a central longitudinal axis of the anchor shaft, is between 5 and 15 mm, and
  a greatest lateral dimension of the open shape, measured perpendicular to the central longitudinal axis, is between 4 and 20 mm.

Inventive concept 253. The method according to inventive concept 204,
  wherein at a plurality of locations along the wire, a cross section of the wire, taken perpendicular to a longitudinal axis of the wire, has a shape that has at least one straight side.

Inventive concept 254. The method according to inventive concept 253, wherein the at least one straight side has a length of at least 3 mm.

Inventive concept 255. The method according to inventive concept 204, wherein the wire is shaped so as to define a proximal opening within 7 mm of a proximal end of the wire, and wherein the proximal portion of the flexible elongate tension member passes through the proximal opening.

Inventive concept 256. The method according to inventive concept 204, wherein the longitudinal segment of the proximal portion of the flexible elongate tension member is coupled in sliding communication with the at least a portion of the anchor shaft when the tissue anchor is unconstrained by the deployment tool.

Inventive concept 257. The method according to inventive concept 256, wherein the tissue anchor includes one or more annular elements, which are disposed around the at least a portion of the anchor shaft, and couple the flexible elongate tension member in the sliding communication with the at least a portion of the anchor shaft when the tissue anchor is unconstrained by the deployment tool.

Inventive concept 258. The method according to inventive concept 204, wherein a proximally-facing surface defined by the tissue-coupling element is concave when the tissue anchor is unconstrained by the deployment tool.

Inventive concept 259. The method according to inventive concept 204, wherein a proximally-facing surface defined by the tissue-coupling element is convex when the tissue anchor is unconstrained by the deployment tool.

Inventive concept 260. The method according to inventive concept 204, wherein one or more tethers are fixed to the flexible elongate tension member.

Inventive concept 261. The method according to inventive concept 204,
  wherein the tissue anchor is a first tissue anchor; and
  wherein the method further includes:
    implanting a second tissue anchor in the subject, which second tissue anchor is separate and distinct from the first tissue anchor; and
    facilitating repair of an atrioventricular valve of the subject by applying tension to one or more tethers that couple flexible elongate tension member to the second tissue anchor.

Inventive concept 262. The method according to inventive concept 261, further including, before applying the tension, coupling the flexible elongate tension member to the second tissue anchor using the one or more tethers.

Inventive concept 263. The method according to inventive concept 261, wherein the one or more tethers are fixed to (a) the flexible elongate tension member and (b) the second tissue anchor.

Inventive concept 204. The method according to inventive concept 261, wherein the one or more tethers are (a) fixed to the second tissue anchor and (b) not fixed to the anchor shaft of the first tissue anchor.

Inventive concept 265. The method according to inventive concept 261, wherein the second tissue anchor includes a helical tissue-coupling element.

Inventive concept 266. The method according to inventive concept 261 wherein the second tissue anchor includes a stent.

Inventive concept 267. The method according to inventive concept 204,
  wherein the tissue anchor is a first tissue anchor, and
  wherein the method further includes:
    implanting a second tissue anchor in the subject, which second tissue anchor (a) separate and distinct from the first tissue anchor, and (b) coupled to the flexible elongate tension member; and
    facilitating repair of an atrioventricular valve of the subject by applying tension to flexible elongate tension member.

Inventive concept 268. The method according to inventive concept 267 wherein the flexible elongate tension member is fixed to the second tissue anchor.

Inventive concept 269. The method according to inventive concept 204, wherein introducing includes introducing the tissue anchor while the tissue-coupling element is constrained by the deployment tool, and a longitudinal portion of the flexible elongate tension member runs alongside a portion of the wire.

Inventive concept 270. The method according to inventive concept 204, wherein the tissue anchor includes an anchor head connected to a proximal portion of the anchor shaft, and wherein, when the tissue anchor is unconstrained by the deployment tool:
  the anchor shaft has a central longitudinal axis,
  the anchor head is coaxial with the central longitudinal axis, and
  the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 271. The method according to inventive concept 270, wherein at least 95% of the area of the projection of the tissue-coupling element on the plane would fall within the first angle.

Inventive concept 272. The method according to inventive concept 270, wherein at least 80% of the area of the projection of the tissue-coupling element on the plane would fall within a third angle of 150 degrees in the plane having the vertex at the central longitudinal axis.

Inventive concept 273. The method according to inventive concept 204, wherein the tissue anchor includes an anchor head connected to a proximal portion of the anchor shaft, wherein the anchor head is shaped so as to define a passage in which the proximal portion of the flexible elongate tension member is slidably disposed, wherein the flexible elongate tension member includes a locking stopper, which is axially fixed to the flexible elongate tension member, wherein the locking stopper and the passage are sized and shaped such that the size and shape of the passage prevent proximal movement of the locking stopper past the passage, and wherein the method further includes, after delivering the tissue-coupling element through the wall of the heart:
  at least partially compressing the open shape by applying tension to the flexible elongate tension member; and
  after the passage prevents proximal movement of the locking stopper past the passage, applying, to the flexible elongate tension member, additional tension that does not further compress the open shape.

Inventive concept 274. The method according to inventive concept 204, wherein the tissue-coupling element further includes a tip, which is fixed to a distal end of the wire, and has, at a widest longitudinal site along the tip, a greatest tip outer cross-sectional area that equals at least 150% of an average wire cross-sectional area of the wire.

Inventive concept 275. The method according to inventive concept 274, wherein the distal site is on the tip.

Inventive concept 276. The method according to inventive concept 274, wherein the tip is shaped so as to define a guidewire lumen therethrough.

Inventive concept 277. The method according to inventive concept 274, wherein the deployment tool includes a deployment shaft shaped so as to define a deployment-shaft lumen, wherein the deployment shaft has a deployment-shaft outer cross-sectional area which equals between 90% and 110% of the greatest tip outer cross-sectional area, and wherein the tip is shaped so as to removably engage a distal end of the deployment shaft.

There is also provided, in accordance with an inventive concept 278 of the present invention, a method including:
  providing a tissue anchor that includes (a) an anchor shaft having a central longitudinal axis, (b) a tissue-coupling element, which (i) extends from a distal end of the anchor shaft, and (ii) includes a wire, and (c) a flexible elongate tension member, which includes a distal portion that is fixed to a site on the wire;

introducing, during a transcatheter procedure, the tissue anchor into a cardiac chamber of a heart of a subject, while the tissue-coupling element is constrained by a deployment tool;

delivering the tissue-coupling element through a wall of the heart; and at least partially releasing the tissue anchor from the deployment tool such that (a) the tissue-coupling element is unconstrained by the deployment tool, (b) the wire of the tissue-coupling element is shaped as an open shape, (c) if the tissue-coupling element were to be projected onto a plane that is perpendicular to the central longitudinal axis, the open shape would surround between 170 and 355 degrees of a point in the plane, (d) a longitudinal segment of a proximal portion of the flexible elongate tension member runs alongside at least a portion of the anchor shaft, (e) a crossing portion of the flexible elongate tension member (i) is disposed between the distal and the proximal portions along the flexible elongate tension member, and (ii) crosses at least a portion of the open shape, and (f) the tissue anchor allows relative axial motion between the at least a portion of the anchor shaft and the longitudinal segment of the proximal portion of the flexible elongate tension member.

Inventive concept 279. The method according to inventive concept 278, wherein the tissue anchor includes an anchor head connected to a proximal portion of the anchor shaft, wherein the anchor head is shaped so as to define a passage in which the proximal portion of the flexible elongate tension member is slidably disposed, wherein the flexible elongate tension member includes a locking stopper, which is axially fixed to the proximal or the crossing portion of the flexible elongate tension member, wherein the locking stopper and the passage are sized and shaped such that the size and shape of the passage prevent proximal movement of the locking stopper past the passage, and wherein the method further includes, after delivering the tissue-coupling element through the wall of the heart:
  at least partially compressing the open shape by applying tension to the flexible elongate tension member; and
  after the passage prevents proximal movement of the locking stopper past the passage, applying, to the flexible elongate tension member, additional tension that does not further compress the open shape.

Inventive concept 280. The method according to inventive concept 278, wherein the open shape is shaped as a portion of a circle or a portion of an ellipse when the tissue anchor is unconstrained by the deployment tool.

Inventive concept 281. The method according to inventive concept 278, wherein the point falls on a projection onto the plane of a line segment that terminates at (a) the site on the wire and (b) a proximal end of the wire when the tissue anchor is unconstrained by the deployment tool.

Inventive concept 282. The method according to inventive concept 278, wherein the site on the wire is at a distal end of the wire.

Inventive concept 283. The method according to inventive concept 282, wherein the wire is shaped so as to define a channel, through which a portion of the flexible elongate tension member passes and exits the wire at the distal end of the wire.

Inventive concept 284. The method according to inventive concept 278, wherein a radius of the flexible elongate tension member is less than a radius of the wire.

Inventive concept 285. The method according to inventive concept 284, wherein the radius of the flexible elongate tension member is less than 50% of the radius of the wire.

Inventive concept 286. The method according to inventive concept 278, wherein, when the tissue anchor is unconstrained by the deployment tool; (a) a line segment that terminates at (i) the site on the wire and (ii) a proximal end of the tissue-coupling element may have a total length that equals a percentage of (b) a total length of the tissue-coupling element, measured the along tissue-coupling element, the percentage between 25% and 75%.

Inventive concept 287. The method according to inventive concept 278, wherein, when the tissue anchor is unconstrained by the deployment tool:
a greatest longitudinal dimension of the open shape, measured in parallel to a central longitudinal axis of the anchor shaft, is between 0.25 and 5 mm, and
a greatest lateral dimension of the open shape, measured perpendicular to the central longitudinal axis, is between 4 and 20 mm.

There is further provided, in accordance with an inventive concept 288 of the present invention, a method including:
providing a tissue anchor that includes (a) an anchor shaft, (b) a tissue-coupling element, which (i) extends from a distal end of the anchor shaft, and (ii) includes a wire, and (c) a flexible elongate tension member;
introducing, during a transcatheter procedure, the tissue anchor into a cardiac chamber of a heart of a subject, while the tissue-coupling element is constrained by a deployment tool;
delivering the tissue-coupling element through a wall of the heart; and
at least partially releasing the tissue anchor from the deployment tool such that (a) the tissue-coupling element is unconstrained by the deployment tool, (b) the wire of the tissue-coupling element is shaped as an open loop having more than one turn, (c) a distal portion of the flexible elongate tension member is fixed to a site on the open loop, (d) a longitudinal segment of a proximal portion of the flexible elongate tension member runs alongside at least a portion of the anchor shaft, (e) a crossing portion of the flexible elongate tension member, disposed between the distal and the proximal portions along the flexible elongate tension member, crosses at least a portion of the open loop, and (f) the tissue anchor allows relative axial motion between the at least a portion of the anchor shaft and the longitudinal segment of the proximal portion of the flexible elongate tension member.

Inventive concept 289. The method according to inventive concept 288, further including, after delivering the tissue-coupling element through the wall of the heart, at least partially compressing the open loop by applying tension to the flexible elongate tension member.

Inventive concept 290. The method according to inventive concept 288, further including, after delivering the tissue-coupling element through the wall of the heart, at least partially compressing the open loop and pulling the tissue-coupling element against an external surface of the heart, by applying tension to the flexible elongate tension member.

Inventive concept 291. The method according to inventive concept 288,
wherein the tissue anchor includes an anchor head connected to a proximal portion of the anchor shaft,
wherein the anchor head is shaped so as to define a passage in which the proximal portion of the flexible elongate tension member is slidably disposed,
wherein the flexible elongate tension member includes a locking stopper, which is axially fixed to the proximal or the crossing portion of the flexible elongate tension member,
wherein the locking stopper and the passage are sized and shaped such that the size and shape of the passage prevent proximal movement of the locking stopper past the passage, and
wherein the method further includes, after delivering the tissue-coupling element through the wall of the heart:
at least partially compressing the open loop by applying tension to the flexible elongate tension member; and
after the passage prevents proximal movement of the locking stopper past the passage, applying, to the flexible elongate tension member, additional tension that does not further compress the open loop.

Inventive concept 292. The method according to inventive concept 291, wherein the locking stopper is axially fixed to the proximal or the crossing portion of the flexible elongate tension member at a distance of between 7 and 22 mm from the site on the open loop.

Inventive concept 293. The method according to inventive concept 291, wherein, if the tissue-coupling element were straightened in an elongated configuration, the locking stopper would be a distance of between 7 and 12 mm from the passage.

Inventive concept 294. The method according to inventive concept 288, wherein the open loop is shaped as a spiral when the tissue anchor is unconstrained by the deployment tool.

Inventive concept 295. The method according to inventive concept 294, wherein the spiral is shaped as a three-dimensional spiral when the tissue anchor is unconstrained by the deployment tool.

Inventive concept 296. The method according to inventive concept 294, wherein the spiral is shaped as an elliptical spiral when the tissue anchor is unconstrained by the deployment tool.

Inventive concept 297. The method according to inventive concept 288, wherein the open loop is shaped as a three-dimensional open loop when the tissue anchor is unconstrained by the deployment tool.

Inventive concept 298. The method according to inventive concept 297, wherein, when the tissue anchor is unconstrained by the deployment tool:
a greatest longitudinal dimension of the three-dimensional open loop, measured in parallel to a central longitudinal axis of the anchor shaft, is between 1 and 5 mm, and
a greatest lateral dimension of the three-dimensional open loop, measured perpendicular to the central longitudinal axis, is between 4 and 20 mm.

Inventive concept 299. The method according to inventive concept 288, further including, after delivering the tissue-coupling element through the wall of the heart:
ascertaining whether the tissue-coupling element overlies a coronary blood vessel; and
if the tissue-coupling element overlies the coronary blood vessel, rotating the tissue anchor until the tissue-coupling element no longer overlies the coronary blood vessel.

Inventive concept 300. The method according to inventive concept 288, further including, after delivering the tissue-coupling element through the wall of the heart:
rotating the tissue anchor by rotating the anchor shaft; and
bringing the tissue-coupling element into contact with an external surface of the heart by applying tension to the flexible elongate tension member.

Inventive concept 301. The method according to inventive concept 300, wherein bringing the tissue-coupling element into contact with the external surface of the heart includes bringing the tissue-coupling element into contact with the external surface of the heart without applying any tension to the anchor shaft.

Inventive concept 302. The method according to inventive concept 288, wherein the site is on an outermost turn of the open loop when the tissue anchor is unconstrained by the deployment tool.

Inventive concept 303. The method according to inventive concept 288, wherein the site is on a second-to-outermost turn of the open loop when the tissue anchor is unconstrained by the deployment tool.

Inventive concept 304. The method according to inventive concept 288, wherein a radius of the flexible elongate tension member is less than a radius of the wire.

Inventive concept 305. The method according to inventive concept 304, wherein the radius of the flexible elongate tension member is less than 50% of the radius of the wire.

Inventive concept 306. The method according to inventive concept 288, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the anchor shaft, an angle between (a) the flexible elongate tension member and (b) a tangent to the open loop at the site would be between 70 and 90 degrees.

Inventive concept 307. The method according to inventive concept 288, wherein, when the tissue anchor is unconstrained by the deployment tool:
the open loop is shaped so as to define an outermost turn and a second-to-outermost at least partial turn, and
the outermost turn at least partially overlaps the second-to-outermost at least partial turn.

Inventive concept 308. The method according to inventive concept 288, wherein, when the tissue anchor is unconstrained by the deployment tool, the open loop is shaped so as to define one or more curved segments and one or more straight segments.

Inventive concept 309. The method according to inventive concept 308, wherein, when the tissue anchor is unconstrained by the deployment tool, the open loop is shaped so as to define the one or more curved segments and two or more straight segments.

Inventive concept 310. The method according to inventive concept 288, wherein the site on the open loop is a first site on the open loop, and wherein, when the tissue anchor is unconstrained by the deployment tool and the flexible elongate tension member is tensioned straight:
the open loop surrounds a center point,
the wire extends from the distal end of the anchor shaft at a second site on the open loop, and
if the tissue-coupling element and the flexible elongate tension member were to be projected onto a plane that is perpendicular to a central longitudinal axis of the anchor shaft, an angle between the first and the second sites, having a vertex at the center point, would be between 130 and 180 degrees.

Inventive concept 311. The method according to inventive concept 310, wherein the angle is between 150 and 180 degrees.

Inventive concept 312. The method according to inventive concept 311 wherein the angle is between 170 and 180 degrees.

Inventive concept 313. The method according to inventive concept 310, wherein the second site is at a radially-outer end of the open loop when the tissue anchor is unconstrained by the deployment tool.

Inventive concept 314. The method according to inventive concept 288, wherein, when the tissue anchor is unconstrained by the deployment tool:
the open loop has a greatest lateral dimension, measured perpendicular to a central longitudinal axis of the anchor shaft, and
a distance between (a) a radially-outer end of the open loop and (b) a radially-inner-most point of the open loop, measured perpendicular to the central longitudinal axis, is equal to at least 30% of the greatest lateral dimension.

Inventive concept 315. The method according to inventive concept 314, wherein a ratio of the greatest longitudinal dimension and the greatest lateral dimension is between 1:2 and 1:18 when the tissue anchor is unconstrained by the deployment tool.

Inventive concept 316. The method according to inventive concept 288, wherein the anchor shaft includes a sealing element.

Inventive concept 317. The method according to inventive concept 288, wherein the anchor shaft has a central longitudinal axis that is straight when the tissue anchor is unconstrained by the deployment tool.

Inventive concept 318. The method according to inventive concept 288, wherein the anchor shaft and the tissue-coupling element are integral to one another.

Inventive concept 319. The method according to inventive concept 288, wherein a cross-sectional area of the wire is at least 0.09 mm2.

Inventive concept 320. The method according to inventive concept 319, wherein the cross-sectional area of the wire is no more than 2.9 mm2.

Inventive concept 321. The method according to inventive concept 288, wherein the flexible elongate tension member includes Nitinol.

Inventive concept 322. The method according to inventive concept 288, wherein the tissue anchor includes an anchor head connected to a proximal portion of the anchor shaft, and wherein, when the tissue anchor is unconstrained by the deployment tool:
the anchor shaft has a central longitudinal axis,
the anchor head is coaxial with the central longitudinal axis, and
the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 323. The method according to inventive concept 322, wherein at least 95% of the area of the projection of the tissue-coupling element on the plane would fall within the first angle.

Inventive concept 324. The method according to inventive concept 322, wherein at least 80% of the area of the projection of the tissue-coupling element on the plane would fall within a third angle of 150 degrees in the plane having the vertex at the central longitudinal axis.

Inventive concept 325. The method according to inventive concept 288, wherein, when the tissue anchor is unconstrained by the deployment tool:
the open loop surrounds a center point, and
(a) a site distance between the site and the distal end of the anchor shaft is greater than (b) a center-point distance between the center point and the distal end of the anchor shaft when the tissue anchor is unconstrained by the deployment tool.

Inventive concept 326. The method according to inventive concept 325, wherein the site distance equals at least 150% of the center-point distance when the tissue anchor is unconstrained by the deployment tool.

Inventive concept 327. The method according to inventive concept 326, wherein the site distance equals at least 175% of the center-point distance when the tissue anchor is unconstrained by the deployment tool.

Inventive concept 328. The method according to inventive concept 288, wherein the longitudinal segment of the proximal portion of the flexible elongate tension member is coupled in sliding communication with the at least a portion of the anchor shaft when the tissue anchor is unconstrained by the deployment tool.

Inventive concept 329. The method according to inventive concept 328, wherein the tissue anchor includes one or more annular elements, which are disposed around the at least a portion of the anchor shaft, and couple the flexible elongate tension member in the sliding communication with the at least a portion of the anchor shaft when the tissue anchor is unconstrained by the deployment tool.

Inventive concept 330. The method according to inventive concept 288, wherein the flexible elongate tension member is not fixed to any portion of the open loop beyond 2 mm from the site on the open loop, measured when the tissue anchor is unconstrained by the deployment tool.

Inventive concept 331. The method according to inventive concept 288, wherein, when the tissue anchor is unconstrained by the deployment tool:
the open loop has a greatest lateral dimension, measured perpendicular to a central longitudinal axis of the anchor shaft, and
the flexible elongate tension member is not fixed to any portion of the open loop beyond a distance from the site on the open loop, wherein the distance equals 30% of the greatest lateral dimension.

Inventive concept 332. The method according to inventive concept 288, wherein the flexible elongate tension member is fixed to the open loop only at the site on the open loop.

Inventive concept 333. The method according to inventive concept 288, wherein, when the tissue anchor is unconstrained by the deployment tool:
the open loop has a greatest lateral dimension, measured perpendicular to a central longitudinal axis of the anchor shaft, and
the at least a portion of the open loop crossed by the crossing portion has a length that equals at least 50% of the greatest lateral dimension.

Inventive concept 334. The method according to inventive concept 333, wherein the length of the at least a portion of the open loop crossed by the crossing portion equals at least 75% of the greatest lateral dimension when the tissue anchor is unconstrained by the deployment tool.

Inventive concept 335. The method according to inventive concept 334, wherein the length of the at least a portion of the open loop crossed by the crossing portion equals at least 90% of the greatest lateral dimension when the tissue anchor is unconstrained by the deployment tool.

Inventive concept 336. The method according to inventive concept 288, wherein the wire extends from a distal end of the anchor shaft at a radially-outer end of the open loop when the tissue anchor is unconstrained by the deployment tool.

Inventive concept 337. The method according to inventive concept 336, wherein, when the tissue anchor is unconstrained by the deployment tool, the open loop surrounds a center point, and the wire intersects the center point.

Inventive concept 338. The method according to inventive concept 336, wherein, when the tissue anchor is unconstrained by the deployment tool, the open loop surrounds a center point, and the wire does not intersect the center point.

Inventive concept 339. The method according to inventive concept 288, wherein the wire extends from a distal end of the anchor shaft at a radially-inner end of the open loop when the tissue anchor is unconstrained by the deployment tool.

Inventive concept 340. The method according to inventive concept 288, wherein a proximally-facing surface defined by the tissue-coupling element is concave when the tissue anchor is unconstrained by the deployment tool.

Inventive concept 341. The method according to inventive concept 288, wherein a proximally-facing surface defined by the tissue-coupling element is convex when the tissue anchor is unconstrained by the deployment tool.

Inventive concept 342. The method according to inventive concept 288, wherein one or more tethers are fixed to the flexible elongate tension member.

Inventive concept 343. The method according to inventive concept 288,
wherein the tissue anchor is a first tissue anchor, and
wherein the method further includes:
implanting a second tissue anchor in the subject, which second tissue anchor is separate and distinct from the first tissue anchor; and
facilitating repair of an atrioventricular valve of the subject by applying tension to one or more tethers that couple the flexible elongate tension member to the second tissue anchor.

Inventive concept 344. The method according to inventive concept 343, further including, before applying the tension, coupling the flexible elongate tension member to the second tissue anchor using the one or more tethers.

Inventive concept 345. The method according to inventive concept 343, wherein the one or more tethers are fixed to (a) the flexible elongate tension member and (b) the second tissue anchor.

Inventive concept 346. The method according to inventive concept 343, wherein the one or more tethers are (a) fixed to the second tissue anchor and (b) not fixed to the anchor shaft of the first tissue anchor.

Inventive concept 347. The method according to inventive concept 343, wherein the second tissue anchor includes a helical tissue-coupling element.

Inventive concept 348. The method according to inventive concept 343, wherein the second tissue anchor includes a stent.

Inventive concept 349. The method according to inventive concept 288,
wherein the tissue anchor is a first tissue anchor, and
wherein the method further includes:
implanting a second tissue anchor in the subject, which second tissue anchor is (a) separate and distinct from the first tissue anchor, and (b) coupled to the flexible elongate tension member; and facilitating repair of an atrioventricular valve of the subject by applying tension to flexible elongate tension member.

Inventive concept 350. The method according to inventive concept 349, wherein the flexible elongate tension member is fixed to the second tissue anchor.

Inventive concept 351. The method according to inventive concept 288, wherein introducing includes introducing the tissue anchor while the tissue-coupling element is constrained by the deployment tool, and a longitudinal portion of the flexible elongate tension member runs alongside a portion of the wire.

Inventive concept 352. The method according to inventive concept 288, wherein the tissue anchor includes an anchor head connected to a proximal portion of the anchor shaft, wherein the anchor head is shaped so as to define:

a first passage, in which the proximal portion of the flexible elongate tension member is slidably disposed, a second passage, in which a proximal portion of the wire of the tissue-coupling element is fixedly disposed, and a third passage, sized for slidable passage therethrough of a guidewire, and wherein the first, the second, and the third passages have respective, different central longitudinal axes.

Inventive concept 353. The method according to inventive concept 352, wherein the third passage has an inner diameter of between 0.25 and 0.75 mm.

Inventive concept 354. The method according to inventive concept 352, wherein a proximal end of the second passage is closed.

Inventive concept 355. The method according to inventive concept 288, wherein the wire is shaped so as to define a channel, which has a lateral opening at the site, and wherein the distal portion of the flexible elongate tension member passes through the lateral opening.

Inventive concept 356. The method according to inventive concept 355, wherein the distal portion of the flexible elongate tension member passes through the lateral opening and extends distally through at least a portion of the channel.

Inventive concept 357. The method according to inventive concept 356, wherein the distal portion of the flexible elongate tension member extends distally through the at least a portion of the channel to at least within 7 mm of a distal end of the wire.

Inventive concept 358. The method according to inventive concept 356, wherein the distal portion of the flexible elongate tension member extends distally through the at least a portion of the channel to the distal end of the wire.

Inventive concept 359. The method according to inventive concept 288, wherein the wire is shaped so as to define first and second major opposing surfaces connected by first and second minor opposing surfaces, wherein the first and the second major opposing surfaces and the first and the second minor opposing surfaces extend along at least 90% of a total length of the wire, and wherein a total surface area of the first minor opposing surface is less than 10% of a total surface area of the major opposing surface.

Inventive concept 360. The method according to inventive concept 359, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 361. The method according to inventive concept 288, wherein, extending along at least 90% of a total length of the wire, the wire has a greatest major dimension and a greatest minor dimension perpendicular to the greatest major dimension, and wherein the greatest major dimension equals at least 150% of the greatest minor dimension.

Inventive concept 362. The method according to inventive concept 361, wherein the tissue anchor includes an anchor head connected to a proximal portion of the anchor shaft, and wherein, when the tissue anchor is unconstrained by the deployment tool:

the anchor shaft has a central longitudinal axis, the anchor head is coaxial with the central longitudinal axis, and the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 363. The method according to inventive concept 288, wherein at a plurality of locations along the wire, across section of the wire, taken perpendicular to a longitudinal axis of the wire, has a shape that has at least one straight side.

Inventive concept 364. The method according to inventive concept 363, wherein the at least one straight side has a length of at least 3 mm.

There is still further provided, in accordance with an inventive concept 365 of the present invention, a method including:

providing a tissue anchor that includes (a) an anchor shaft, (b) a tissue-coupling element, which (i) extends from a distal end of the anchor shaft, (ii) includes a wire and a tip, which is fixed to a distal end of the wire; and has, at a widest longitudinal site along the tip, a greatest tip outer cross-sectional area that equals at least 150% of an average wire cross-sectional area of the wire, and (c) a flexible elongate tension member;

introducing, during a transcatheter procedure, the tissue anchor into a cardiac chamber of a heart of a subject, while the tissue-coupling element is constrained by a deployment tool;

delivering the tissue-coupling element through a wall of the heart; and at least partially releasing the tissue anchor from the deployment tool such that (a) the tissue-coupling element is unconstrained by the deployment tool, (b) the tissue-coupling element is shaped as an open shape, (c) a distal portion of the flexible elongate tension member is fixed to a site on the open shape, (d) a longitudinal segment of a proximal portion of the flexible elongate tension member runs alongside at least a portion of the anchor shaft, (e) a crossing portion of the flexible elongate tension member (i) is disposed between the distal and the proximal portions along the flexible elongate tension member, and (ii) crosses at least a portion of the open shape, and (f) the tissue anchor allows relative axial motion between the at least a portion of the anchor shaft and the longitudinal segment of the proximal portion of the flexible elongate tension member.

Inventive concept 366. The method according to inventive concept 365, further including, after delivering the tissue-coupling element through the wall of the heart, at least partially compressing the open shape by applying tension to the flexible elongate tension member.

Inventive concept 367. The method according to inventive concept 365, further including, after delivering the tissue-coupling element through the wall of the heart, at least partially compressing the open shape and pulling the tissue-coupling element against an external surface of the heart, by applying tension to the flexible elongate tension member.

Inventive concept 368. The method according to inventive concept 365, wherein the greatest tip outer cross-sectional area equals at least 200% of the average anchoring-element outer cross-sectional area.

Inventive concept 369. The method according to inventive concept 365, wherein the greatest tip outer cross-sectional area is greater than 1 mm2.

Inventive concept 370. The method according to inventive concept 365, wherein the tip includes a frustoconical portion.

Inventive concept 371. The method according to inventive concept 365, wherein the tip is shaped so as to define a guidewire lumen therethrough.

Inventive concept 372. The method according to inventive concept 371, wherein the tip has a central longitudinal axis, which (a) passes through a distal end-opening of the guidewire lumen, and (b) does not pass through a proximal end-opening of the guidewire lumen.

Inventive concept 373. The method according to inventive concept 372, wherein a center of the distal end-opening of the guidewire lumen is disposed within 1 mm of the central longitudinal axis of the tip.

Inventive concept 374. The method according to inventive concept 372, wherein the central longitudinal axis of the tip passes through the distal end of the wire.

Inventive concept 375. The method according to inventive concept 365, wherein the distal portion of the flexible elongate tension member at least partially runs along the open shape between the site and the tip.

Inventive concept 376. The method according to inventive concept 375, wherein the distal portion of the flexible elongate tension member, at one or more locations along the distal portion, is fixed to the tip.

Inventive concept 377. The method according to inventive concept 376, wherein the tip is shaped so as to define a tension-member lumen therethrough, and wherein the distal portion of the flexible elongate tension member passes through at least a portion of the tension-member lumen.

Inventive concept 378. The method according to inventive concept 365, wherein the deployment tool includes a deployment shaft shaped so as to define a deployment-shaft lumen, wherein the deployment shaft has a deployment-shaft outer cross-sectional area which equals between 90% and 110% of the greatest tip outer cross-sectional area, and wherein the tip is shaped so as to removably engage a distal end of the deployment shaft.

Inventive concept 379. The method according to inventive concept 378, wherein the tip is shaped so as to define a guidewire lumen therethrough, wherein the deployment shaft is shaped so as to define a guidewire opening through a wall of the deployment shaft, and wherein the guidewire opening reaches the distal end of the deployment shaft.

Inventive concept 380. The method according to inventive concept 365, wherein the tissue anchor includes an anchor head connected to a proximal portion of the anchor shaft, wherein the anchor head is shaped so as to define:

a first passage, in which the proximal portion of the flexible elongate tension member is slidably disposed, a second passage, in which a proximal portion of the wire of the tissue-coupling element is fixedly disposed, and a third passage, sized for slidably passage therethrough of a guidewire, and wherein the first, the second, and the third passages have respective, different central longitudinal axes.

Inventive concept 381. The method according to inventive concept 380, wherein the third passage has an inner diameter of between 0.25 and 0.75 mm.

Inventive concept 382. The method according to inventive concept 380, wherein a proximal end of the second passage is closed.

Inventive concept 383. The method according to inventive concept 365, wherein the open shape is an open loop having more than one turn when the tissue anchor is unconstrained by the deployment tool.

Inventive concept 384. The method according to inventive concept 383, wherein the open loop is shaped as a spiral when the tissue anchor is unconstrained by the deployment tool.

Inventive concept 385. The method according to inventive concept 384, wherein the spiral is shaped as a three-dimensional spiral when the tissue anchor is unconstrained by the deployment tool.

Inventive concept 386. The method according to inventive concept 384, wherein the spiral is shaped as an elliptical spiral when the tissue anchor is unconstrained by the deployment tool.

Inventive concept 387. The method according to inventive concept 383, wherein the open loop is shaped as a three-dimensional open loop when the tissue anchor is unconstrained by the deployment tool.

Inventive concept 388. The method according to inventive concept 387, wherein, when the tissue anchor is unconstrained by the deployment tool:

a greatest longitudinal dimension of the three-dimensional open loop, measured in parallel to a central longitudinal axis of the anchor shaft, is between 1 and 5 mm, and a greatest lateral dimension of the three-dimensional open loop, measured perpendicular to the central longitudinal axis, is between 4 and 20 mm.

Inventive concept 389. The method according to inventive concept 383, wherein the site is on an outermost turn of the open loop when the tissue anchor is unconstrained by the deployment tool.

Inventive concept 390. The method according to inventive concept 383, wherein, when the tissue anchor is unconstrained by the deployment tool and the flexible elongate tension member is tensioned straight, if the tissue-coupling element and the flexible elongate tension member were to be projected onto a plane that is perpendicular to a central longitudinal axis of the anchor shaft, an angle between (a) the flexible elongate tension member and (b) a tangent to the open loop at the site would be between 70 and 90 degrees.

Inventive concept 391. The method according to inventive concept 383, wherein, when the tissue anchor is unconstrained by the deployment tool:
  the open loop is shaped so as to define an outermost turn and a second-to-outermost at least partial turn, and
  the outermost turn at least partially overlaps the second-to-outermost at east partial turn.

Inventive concept 392. The method according to inventive concept 383, wherein the site on the open loop is a first site on the open loop, and wherein, when the tissue anchor is unconstrained by the deployment tool and the flexible elongate tension member is tensioned straight:
  the open loop surrounds a center point,
  the wire extends from the distal end of the anchor shaft at a second site on the open loop, and
  if the tissue-coupling element and the flexible elongate tension member were to be projected onto a plane that is perpendicular to a central longitudinal axis of the anchor shaft, an angle between the first and the second sites, having a vertex at the center point, would be between 130 and 180 degrees.

Inventive concept 393. The method according to inventive concept 392, wherein the second site is at a radially-outer end of the open loop when the tissue anchor is unconstrained by the deployment tool.

Inventive concept 394. The method according to inventive concept 383, wherein the wire extends from the distal end of the anchor shaft at a radially-outer end of the open loop when the tissue anchor is unconstrained by the deployment tool.

Inventive concept 395. The method according to inventive concept 383, wherein the wire extends from the distal end of the anchor shaft at a radially-inner end of the open loop when the tissue anchor is unconstrained by the deployment tool.

Inventive concept 396. The method according to inventive concept 365, wherein a radius of the flexible elongate tension member is less than a radius of the wire.

Inventive concept 397. The method according to inventive concept 396, wherein the radius of the flexible elongate tension member is less than 50% of the radius of the wire.

Inventive concept 398. The method according to inventive concept 365, wherein the anchor shaft has a central longitudinal axis that is straight when the tissue anchor is unconstrained by the deployment tool.

Inventive concept 399. The method according to inventive concept 365, wherein the anchor shaft and the tissue-coupling element are integral to one another.

Inventive concept 400. The method according to inventive concept 365, wherein the tissue anchor includes an anchor head connected to a proximal portion of the anchor shaft, and wherein, when the tissue anchor is unconstrained by the deployment tool:
  the anchor shaft has a central longitudinal axis,
  the anchor head is coaxial with the central longitudinal axis, and
  the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

Inventive concept 401. The method according to inventive concept 400, wherein at least 95% of the area of the projection of the tissue-coupling element on the plane would fall within the first angle.

Inventive concept 402. The method according to inventive concept 400, wherein at least 80% of the area of the projection of the tissue-coupling element on the plane would fall within a third angle of 150 degrees in the plane having the vertex at the central longitudinal axis.

Inventive concept 403. The method according to inventive concept 365,
  wherein the tissue anchor includes an anchor head connected to a proximal portion of the anchor shaft,
  wherein the anchor head is shaped so as to define a passage in which the proximal portion of the flexible elongate tension member is slidably disposed,
  wherein the flexible elongate tension member includes a locking stopper, which is axially fixed to the proximal or the crossing portion of the flexible elongate tension member,
  wherein the locking stopper and the passage are sized and shaped such that the size and shape of the passage prevent proximal movement of the locking stopper past the passage, and
  wherein the method further includes, after delivering the tissue-coupling element through the wall of the heart:
    at least partially compressing the open shape by applying tension to the flexible elongate tension member; and
    after the passage prevents proximal movement of the locking stopper past the passage, applying, to the flexible elongate tension member, additional tension that does not further compress the open shape.

Inventive concept 404. The method according to inventive concept 403, wherein the locking stopper is axially fixed to the proximal or the crossing portion of the flexible elongate tension member at a distance of between 7 and 22 mm from the site on the open shape.

Inventive concept 405. The method according to inventive concept 403, wherein, if the tissue-coupling element were straightened in an elongated configuration, the locking stopper would be a distance of between 7 and 12 mm from the passage.

Inventive concept 406. The method according to inventive concept 365, wherein the longitudinal segment of the proximal portion of the flexible elongate tension member is coupled in sliding communication with the at least a portion of the anchor shaft when the tissue anchor is unconstrained by the deployment tool.

Inventive concept 407. The method according to inventive concept 406, wherein the tissue anchor includes one or more annular elements, which are disposed around the at least a portion of the anchor shaft, and couple the flexible elongate tension member in the sliding communication with the at least a portion of the anchor shaft when the tissue anchor is unconstrained by the deployment tool.

Inventive concept 408. The method according to inventive concept 365, wherein one or more tethers are fixed to the flexible elongate tension member.

Inventive concept 409. The method according to inventive concept 365,
  wherein the tissue anchor is a first tissue anchor, and
  wherein the method further includes:
    implanting a second tissue anchor in the subject, which second tissue anchor is separate and distinct from the first tissue anchor; and facilitating repair of an atrioventricular valve of the subject by applying tension to one or more tethers that couple the flexible elongate tension member to the second tissue anchor.

Inventive concept 410. The method according to inventive concept 409, further including, before applying the tension, coupling the flexible elongate tension member to the second tissue anchor using the one or more tethers.

Inventive concept 411. The method according to inventive concept 409, wherein the one or more tethers are (a) fixed to the second tissue anchor and (b) not fixed to the anchor shaft of the first tissue anchor.

Inventive concept 412. The method according to inventive concept 409, wherein the second tissue anchor includes a helical tissue-coupling element.

Inventive concept 413. The method according to inventive concept 409, wherein the second tissue anchor includes a stent.

Inventive concept 414. The method according to inventive concept 365,
wherein the tissue anchor is a first tissue anchor, and
wherein the method further includes:
implanting a second tissue anchor in the subject, which second tissue anchor is (a) separate and distinct from the first tissue anchor, and (b) coupled to the flexible elongate tension member; and
facilitating repair of an atrioventricular valve of the subject by applying tension to flexible elongate tension member.

Inventive concept 415. The method according to inventive concept 414, wherein the flexible elongate tension member is fixed to the second tissue anchor.

Inventive concept 416. The method according to inventive concept 365, wherein introducing includes introducing the tissue anchor while the tissue-coupling element is constrained by the deployment tool, and a longitudinal portion of the flexible elongate tension member runs alongside a portion of the wire.

Inventive concept 417. The method according to inventive concept 365, wherein the wire is shaped so as to define a channel, which has a lateral opening at the site, and wherein the distal portion of the flexible elongate tension member passes through the lateral opening.

Inventive concept 418. The method according to inventive concept 417, wherein the distal portion of the flexible elongate tension member passes through the lateral opening and extends distally through at least a portion of the channel.

Inventive concept 419. The method according to inventive concept 418, wherein the distal portion of the flexible elongate tension member extends distally through the at least a portion of the channel to at least within 7 mm of a distal end of the wire.

Inventive concept 420. The method according to inventive concept 418, wherein the distal portion of the flexible elongate tension member extends distally through the at least a portion of the channel to the distal end of the wire.

Inventive concept 421. The apparatus according to any one of inventive concepts 1, 69, 79, and 150, wherein the tissue anchor is shaped so as to define a bend at an interface between the tissue-coupling element and the anchor shaft.

Inventive concept 422. The apparatus according to inventive concept 421, wherein the bend has an angle of between 45 and 135 degrees.

Inventive concept 423. The apparatus according to inventive concept 422, wherein the angle is between 60 and 120 degrees.

There is additionally provided, in accordance with an application of the present invention, apparatus for delivery in a constrained state within a deployment tool, the apparatus including a tissue anchor, which includes:
an anchor shaft;
an anchor head connected to a proximal portion of the anchor shaft; and
a tissue-coupling element, which extends from a distal end of the anchor shaft, wherein, when the tissue anchor is unconstrained by the deployment tool:
the anchor shaft has a central longitudinal axis,
the anchor head is coaxial with the central longitudinal axis, and
the tissue-coupling element is shaped such that if the tissue-coupling element were to be projected onto a plane that is perpendicular to the central longitudinal axis, (a) at least 80% of an area of a projection of the tissue-coupling element on the plane would fall within a first angle of 180 degrees in the plane having a vertex at the central longitudinal axis, and (b) the area would partially overlap, at least 3 mm from the vertex, both rays of a second angle of between 45 and 180 degrees in the plane having the vertex at the central longitudinal axis.

For some applications, at least 95% of the area of the projection of the tissue-coupling element on the plane would fall within the first angle.

For some applications, at least 80% of the area of the projection of the tissue-coupling element on the plane would fall within a third angle of 150 degrees in the plane having the vertex at the central longitudinal axis.

For some applications, an outer portion of the area of the projection of the tissue-coupling element on the plane would fall within all angular positions of a fourth angle of 90 degrees in the plane having the vertex at the central longitudinal axis, which outer portion consists of all points of the area at least 3 mm from the vertex.

For some applications, these techniques are practiced in combination with any of the inventive concepts described hereinabove.

There is yet additionally provided, in accordance with an application of the present invention, a method including:
providing a tissue anchor that includes (a) an anchor shaft, (b) an anchor head connected to a proximal portion of the anchor shaft, and (c) a tissue-coupling element, which extends from a distal end of the anchor shaft;
introducing, during a transcatheter procedure, the tissue anchor into a cardiac chamber of a heart of a subject, while the tissue-coupling element is constrained by a deployment tool;
delivering the tissue-coupling element through a wall of the heart; and
at least partially releasing the tissue anchor from the deployment tool such that (a) the tissue-coupling element is unconstrained by the deployment tool, (b) the anchor head is coaxial with a central longitudinal axis of the anchor shaft, and (c) the tissue-coupling element is shaped such that if the tissue-coupling element were to be projected onto a plane that is perpendicular to the central longitudinal axis, (i) at least 80% of an area of a projection of the tissue-coupling element on the plane would fall within a first angle of 180 degrees in the plane having a vertex at the central longitudinal axis, and (ii) the area would partially overlap, at least 3 mm from the vertex, both rays of a second angle of between 45 and 180 degrees in the plane having the vertex at the central longitudinal axis.

For some applications, the method further includes, after delivering the tissue-coupling element through the wall of the heart:

ascertaining whether the tissue-coupling element overlies a coronary blood vessel; and if the tissue-coupling element overlies the coronary blood vessel, rotating the tissue anchor until the tissue-coupling element no longer overlies the coronary blood vessel.

For some applications, the method further includes, after delivering the tissue-coupling element through the wall of the heart, rotating the tissue anchor and bringing the tissue-coupling element into contact with an external surface of the heart.

For some applications:

introducing the tissue anchor into the cardiac chamber includes introducing the tissue anchor into an atrium of the heart, and bringing the tissue-coupling element into contact with the external surface of the heart includes bringing the tissue-coupling element into contact with an external surface of a ventricle of the heart.

For some applications:

introducing the tissue anchor into the atrium includes introducing the tissue anchor into a right atrium, and bringing the tissue-coupling element into contact with the external surface of the ventricle includes bringing the tissue-coupling element into contact with an external surface of a right ventricle.

For some applications, at least 95% of the area of the projection of the tissue-coupling element on the plane would fall within the first angle.

For some applications, at least 80% of the area of the projection of the tissue-coupling element on the plane would fall within a second angle of 150 degrees in the plane having the vertex at the central longitudinal axis.

For some applications, an outer portion of the area of the projection of the tissue-coupling element on the plane would fall within all angular positions of a second angle of 90 degrees in the plane having the vertex at the central longitudinal axis, which outer portion consists of all points of the area at least 3 mm from the vertex.

For some applications, these techniques are practiced in combination with any of the inventive concepts described hereinabove.

The present invention will be more fully understood from the following detailed description of embodiments thereof, taken together with the drawings, in which:

BRIEF DESCRIPTION OF THE DRAWINGS

FIG. 1A is a schematic illustration of a tissue anchor before deployment from a deployment tool, in accordance with an application of the present invention;

FIGS. 1B-D are schematic illustrations of the tissue anchor of FIG. 1A after deployment from the deployment tool, in accordance with an application of the present invention;

FIGS. 2A-B are schematic illustrations of another tissue anchor before deployment from a deployment tool, in accordance with an application of the present invention;

FIG. 3D is a schematic illustration of an anchor head of the tissue anchor of FIGS. 2A-3C, in accordance with an application of the present invention;

FIGS. 4A-B are schematic illustrations of two configurations of a tissue anchor system, in accordance with respective applications of the present invention;

FIGS. 6A-B are schematic illustrations of yet another tissue anchor before deployment from a deployment tool, in accordance with an application of the present invention;

FIGS. 10A-H are schematic illustrations of configurations of tissue anchors, in accordance with respective applications of the present invention;

FIG. 11A is a schematic illustration of the tissue anchor of FIG. 10E before deployment from a deployment tool, in accordance with an application of the present invention;

FIG. 11B is a schematic illustration of the tissue anchor of FIG. 10F before deployment from a deployment tool, in accordance with an application of the present invention;

FIG. 12 is a schematic illustration of another configuration of an open loop of a tissue anchor, in accordance with an application of the present invention;

FIGS. 14A-D are schematic illustrations of a method for deploying the tissue anchor system of FIG. 4B for repairing a tricuspid valve, in accordance with an application of the present invention;

DETAILED DESCRIPTION OF APPLICATIONS

Figure 3A:
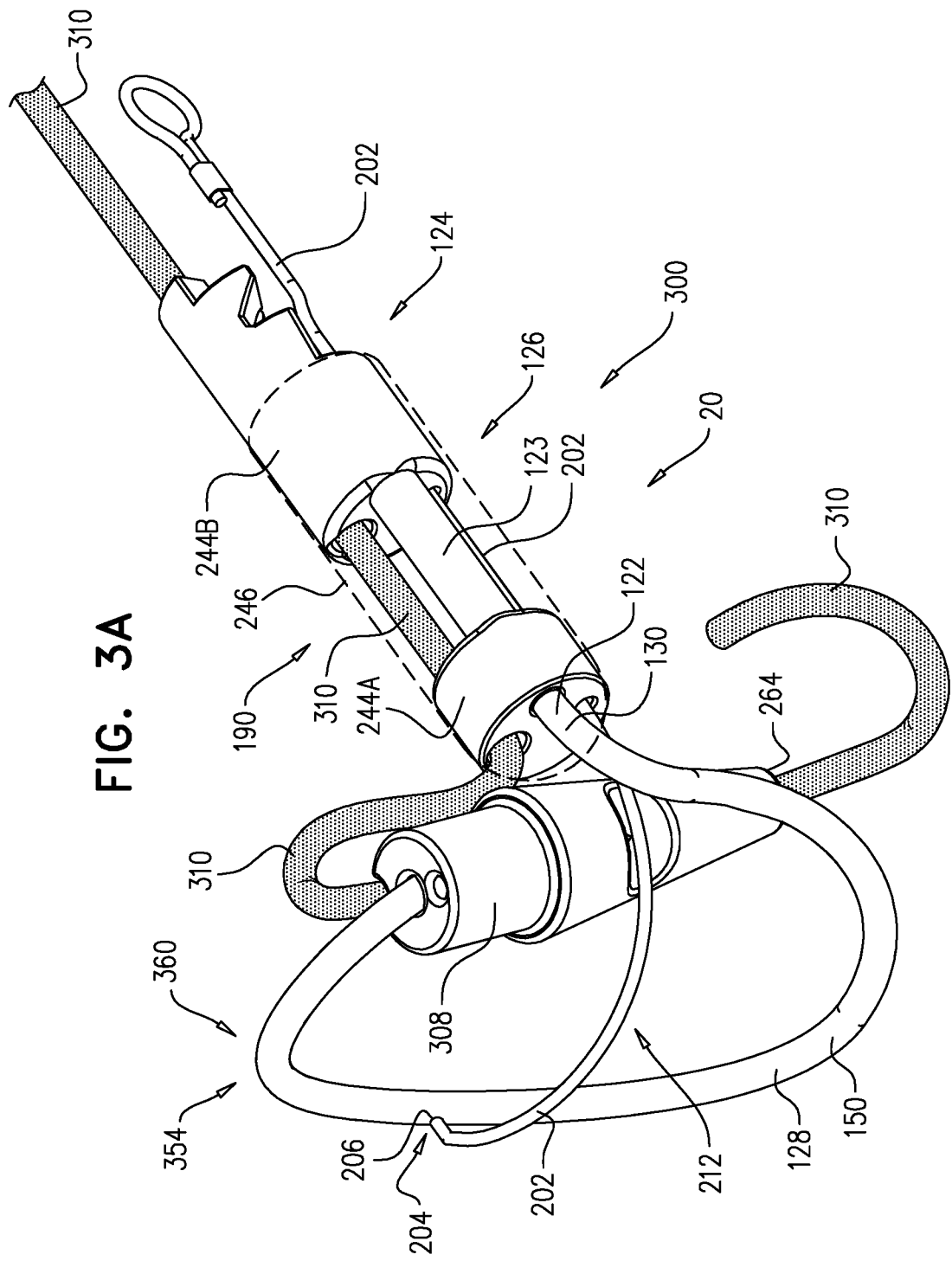
FIGS. 3A-C are schematic illustrations of the tissue anchor of FIGS. 2A-B after deployment from the deployment tool, in accordance with an application of the present invention.

Some embodiments of the present invention provide a tissue anchor 20 and a deployment tool 30, which is typically configured to deliver the tissue anchor through a wall of a heart of a subject.

FIG. 1A is a schematic illustration of a tissue anchor 200 before deployment from deployment tool 30, and FIGS. 1B-D are schematic illustrations of tissue anchor 200 after deployment from deployment tool 30, in accordance with an application of the present invention. Tissue anchor 200 is one implementation of tissue anchor 20, described above. Tissue anchor 200 comprises (a) an anchor shaft 122, (b) an anchor head 124 connected to a proximal portion 126 of anchor shaft 122, and (c) a tissue-coupling element 128, which extends from a distal end 130 of anchor shaft 122. For some applications, anchor shaft 122 and tissue-coupling element 128 are integral to one another; for example, anchor shaft 122 and tissue-coupling element 128 may comprise a wire.

Deployment tool 30 is configured to constrain tissue-coupling element 128 while delivering tissue-coupling element 128 through tissue. For some applications, deployment tool 30 is shaped so as to define a sharp distal piercing tip 32, which is advanced through the wall of the heart of the subject. Typically, during delivery, such as shown in FIG. 1A, deployment tool 30 is configured to hold tissue-coupling element 128 in an elongated, unwound configuration, which may be straight (configuration not shown) or curvy (such as shown in FIG. 1A). For some applications, deployment tool 30 comprises a deployment shaft 34 shaped so as to define a deployment-shaft lumen, such as a hypodermic needle. The deployment-shaft lumen is sized to hold tissue-coupling element 128 constrained therein, and, optionally, to hold other portions of tissue anchor 20 therein, such as anchor shaft 122 and/or anchor head 124. For some applications, deployment tool 30 has a length of between 100 and 180 cm, and/or an inner diameter of between 2 and 6 mm. For some applications, deployment tool 30 comprises a distal-most rigid portion, which typically has a length of 5 to 25 mm, and the remaining proximal portion of the deployment tool is flexible (but not extendable or compressible). For some applications, the proximal portion is shaped so as to define one or more lateral slots 36, which provide flexibility to the proximal portion, while maintaining a backbone that prevents longitudinal compression and extension of the proximal portion. Typically, deployment tool 30 is advanced within a steerable catheter tube, as is known in the art, which may, for example, comprise a braided material. Typically, tissue anchor 20 is provided in sterile packaging, optionally pre-positioned in deployment tool 30.

For some applications, tissue-coupling element 128 comprises a wire 150. For some applications, a cross-sectional area of wire 150 is at least 0.09 mm2 (such as at least 0.18 mm2), no more than 3 mm2 (e.g., no more than 2.9 mm2), and/or between 0.09 mm2 (such as 0.18 mm2) and 3 mm2 (e.g., 2.9 mm2). For some applications, wire 150 has a circular cross-section, and a diameter of wire 150 is at least 0.18 mm, no more than 2 mm, and/or between 0.18 and 2 mm. For some applications, a distal end 152 of wire 150 does not define a sharp distal tip; for example, the distal end may be blunt. For some applications, wire 150 comprises metal, such as Nitinol. For some applications, wire 150 comprises one or more radiopaque markers.

FIG. 1A shows tissue anchor 200 (including tissue-coupling element 128, anchor shaft 122, and anchor head 124) fully constrained by deployment tool 30. Typically, when tissue-coupling element 128 is constrained by the deployment tool, a longitudinal portion of flexible elongate tension member 202, described hereinbelow, runs alongside a portion of wire 150. For some applications, deployment tool 30 comprises a removable driver 201, which comprises a driver head 203 and at least one shaft 205 that is coupled to the driver head. Driver head 203 is removably coupled to anchor head 124 during penetration of tissue-coupling element 128 through tissue, as described hereinbelow. The at least one shaft 205 is configured to controllably detach the driver head from the anchor head. For example, a deployment needle may run through a channel of the at least one shaft; pulling on the needle detaches the driver head from the anchor head.

When tissue anchor 200 is fully constrained by deployment tool 30, tissue-coupling element 128 typically has an outer diameter of at least 0.3 mm, no more than 4 mm, and/or between 0.3 and 4 mm, such as at least 1 mm, no more than 3 mm, and/or between 1 and 3 mm.

For some applications, anchor shaft 122 and tissue-coupling element 128 are integral to one another; for example, anchor shaft 122 and tissue-coupling element 128 may both comprise wire 150, as shown.

Figure 7:
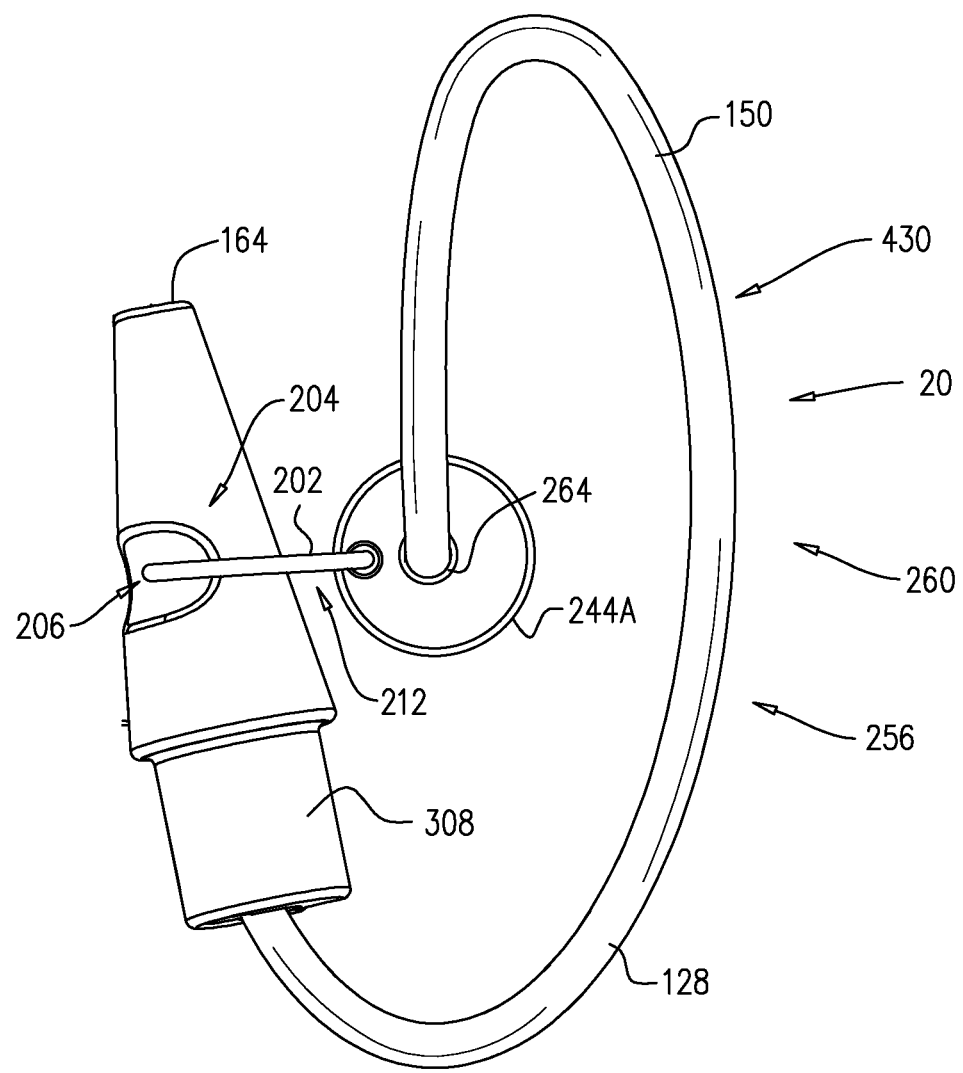
FIG. 7 is a schematic illustration of still another tissue anchor after deployment from a deployment tool, in accordance with an application of the present invention.

When tissue anchor 200 is unconstrained by deployment tool 30, such as shown in FIGS. 1B-D, wire 150 is shaped as an open loop 154 (e.g., a three-dimensional open loop), such as a spiral 160 (e.g., a three-dimensional spiral) around a center point 162 (labeled in FIG. 1D). For some applications, such as shown in FIGS. 1B-D, wire 150 extends from distal end 130 of anchor shaft 122 at a radially-outer end 164 of open loop 154 (e.g., spiral 160) (labeled in FIGS. 1C and 1D), when tissue anchor 200 is unconstrained by deployment tool 30. For some applications, wire 150 intersects center point 162 when tissue anchor 200 is unconstrained by deployment tool 30 (configuration not shown), while for other applications, wire 150 does not intersect center point 162 when tissue anchor 200 is unconstrained by deployment tool 30 (as shown). For other applications, such as shown in FIG. 7, described hereinbelow, wire 150 extends from distal end 130 of anchor shaft 122 at radially-inner end 264 of an open loop 354 (e.g., a spiral 360).

Tissue anchor 200 further comprises a flexible elongate tension member 202, which includes:
- a distal portion 204 that is fixed to a site 206 on open loop 154 (e.g., spiral 160) (such as by welding, soldering, crimping, and/or knotting, and/or as described hereinbelow with reference to FIGS. 9A-F),
- a proximal portion 208, which has a longitudinal segment 209 that runs alongside at least a portion 210 of anchor shaft 122 (labeled in FIG. 1C, in which the at least a portion 210 of anchor shaft 122 is the entire length of anchor shaft 122), and
- a crossing portion 212, which (a) is disposed between distal and proximal portions 204 and 208 along flexible elongate tension member 202, and (b) crosses at least a portion of open loop 154 (e.g., spiral 160) when tissue anchor 200 is unconstrained by deployment tool 30.

Although flexible elongate tension member 202 is fixed to wire 150 of tissue-coupling element 128, flexible elongate tension member 202 is typically distinct from wire 150. In other words, flexible elongate tension member 202 and wire 150 are not two longitudinal portions of a single continuous wire, i.e., are not longitudinally contiguous with each other.

Tension is applied to tissue-coupling element 128 of tissue anchor 200 via flexible elongate tension member 202. The applied tension is resisted by the outward force of open loop 154 (e.g., spiral 160). The applied tension at least partially compresses and stiffens open loop 154 (e.g., spiral 160). This arrangement of tension distribution may overcome any natural tendency of open loop 154 (e.g., spiral 160) to straighten (i.e., unwind) if tension were to be applied along a central longitudinal axis 134 of anchor shaft 122 via anchor shaft 122, and thus may allow the application of a greater load to open loop 154 (e.g., spiral 160). In addition, this stiffening technique allows open loop 154 (e.g., spiral 160) to be manufactured less stiff than it otherwise would need to be, which facilitates straightening and delivering the tissue anchor, and subsequent stiffening in situ.

Typically, before tension is applied to flexible elongate tension member 202, when tissue anchor 200 is unconstrained by deployment tool 30, flexible elongate tension member 202 is not taut across the at least a portion of open loop 154 (e.g., spiral 160). For example, flexible elongate tension member 202 may arc distally, such as can best be seen in FIG. 1C.

Typically, tissue anchor 200 is configured to allow relative axial motion between the at least a portion 210 of anchor shaft 122 and longitudinal segment 209 of proximal portion 208 of flexible elongate tension member 202 when tissue anchor 200 is unconstrained by deployment tool 30 (as flexible elongate tension member 202 is tensioned and pulls on tissue-coupling element 128, tissue anchor 200 becomes progressively more constrained by flexible elongate tension member 202; the relative axial motion nevertheless remains possible). In other words, longitudinal segment 209 of proximal portion 208 of flexible elongate tension member 202 is axially moveable with respect to the at least a portion 210 of anchor shaft 122 when tissue anchor 200 is unconstrained by deployment tool 30. Such axial motion allows tension to be applied to flexible elongate tension member 202 without also being applied to anchor shaft 122, and allows open loop 154 (e.g., spiral 160) to be unwound and flexible elongate tension member 202 to be disposed alongside a portion of flexible elongate tension member 202, as shown in FIG. 1A (in which deployment tool 30 constrains both constrain tissue-coupling element 128 and flexible elongate tension member 202). Typically, longitudinal segment 209 of proximal portion 208 of flexible elongate tension member 202 is coupled in sliding communication with the at least a portion 210 of anchor shaft 122, when tissue anchor 200 is unconstrained by deployment tool 30. For some applications, tissue anchor 200 comprises one or more annular elements, which are disposed around the at least a portion of anchor shaft 122, and couple flexible elongate tension member 202 in the sliding communication with the at least a portion 210 of anchor shaft 122, when tissue anchor 200 is unconstrained by deployment tool 30. For example, the annular elements may comprise one or more collars 244, described hereinbelow, loops, or rings.

For some applications, flexible elongate tension member 202 is not fixed to any portion of open loop 154 (e.g., spiral 160) beyond 2 mm from site 206 on open loop 154 (e.g., spiral 160), measured when tissue anchor 200 is unconstrained by deployment tool 30. Alternatively or additionally, when tissue anchor 200 is unconstrained by deployment tool 30, flexible elongate tension member 202 is not fixed to any portion of open loop 154 (e.g., spiral 160) beyond a distance from site 206 on open loop 154 (e.g., spiral 160), which distance equals 30% of greatest lateral dimension D3 of open loop 154 (e.g., spiral 160) of tissue-coupling element 128, measured perpendicular to central longitudinal axis 134 (labeled in FIG. 5A). For some applications, flexible elongate tension member 202 is fixed to open loop 154 (e.g., spiral 160) only at site 206 on open loop 154 (e.g., spiral 160). Alternatively, a distal portion of flexible elongate tension member 202 beyond site 206 is fixed to open loop 154 (e.g., spiral 160), such as described hereinbelow with reference to FIGS. 9A-E.

Typically, when tissue anchor 200 is unconstrained by deployment tool 30, the at least a portion of open loop 154 (e.g., spiral 160) crossed by crossing portion 212 has a length that equals at least 33% (e.g., at least 50%, at least 75%, or at least 90%) of greatest lateral dimension of open loop 154 (e.g., spiral 160) of tissue-coupling element 128, measured perpendicular to central longitudinal axis 134. (A similar greatest lateral dimension D3 of open loop 354 of tissue anchor 300 is labeled in FIG. 5A).

For some applications, as shown, site 206 is on an outermost turn 214 of open loop 154 (e.g., spiral 160) (labeled in FIG. 1D), when tissue anchor 200 is unconstrained by deployment tool 30. For some other applications, site 206 is on a second-to-outermost turn 216 of open loop 154 (e.g., spiral 160) (labeled in FIG. 1D), when tissue anchor 200 is unconstrained by deployment tool 30 (configuration not shown).

Typically, a radius of flexible elongate tension member 202 is less than a radius of wire 150, such as less than 50% of the radius of wire 150. For some applications a cross-sectional area of wire 150 is at least 0.09 mm2 (such as at least 0.18 mm2), no more than 3 mm2 (e.g., no more than 2.9 mm2), and/or between 0.09 mm2 (such as 0.18 mm2) and 3 mm2 (e.g., 2.9 mm2). For some applications, flexible elongate tension member 202 comprises metal, such as a metal alloy, e.g., Nitinol. For some applications, flexible elongate tension member 202 comprises radiopaque sections or is radiopaque, to enable observation of the relative movement when tensioning.

For some applications, site 206 on open loop 154 (e.g., spiral 160) is a first site 206 on open loop 154 (e.g., spiral 160), and, when tissue anchor 200 is unconstrained by deployment tool 30 and flexible elongate tension member 202 is tensioned straight, (a) wire 150 extends from distal end 130 of anchor shaft 122 at a second site 218 on open loop 154 (e.g., spiral 160), and (b) if tissue-coupling element 128 and flexible elongate tension member 202 were to be projected onto plane 136 that is perpendicular to central longitudinal axis 134, an angle θ (theta) between the first and the second sites, having a vertex 242 at center point 162, would be between 130 and 180 degrees, such as between 150 and 180 degrees, e.g., between 170 and 180 degrees (labeled in FIG. 1D). For some applications, as shown, second site 218 is at radially-outer end 164 of open loop 154 (e.g., spiral 160).

Alternatively or additionally, for some applications, as labeled in FIG. 1D, when tissue anchor 200 is unconstrained by deployment tool 30 and flexible elongate tension member 202 is tensioned straight, if tissue-coupling element 128 and flexible elongate tension member 202 were to be projected onto plane 136 that is perpendicular to central longitudinal axis 134, an angle φ (phi) between (a) flexible elongate tension member 202 and (b) a tangent 250 to open loop 154 (e.g., spiral 160) at site 206 would be between 45 and 90 degrees, such as between 70 and 90 degrees, e.g., 90 degrees.

For some application, anchor shaft 122 comprises a sealing element 190. For some applications, sealing element 190 comprises one or more collars 244 disposed around anchor shaft 122, and, typically, a sleeve 246 that couples the collars 244 together. Sleeve 246 defines a lumen having proximal and distal ends. The flexible elongate tension member 202 slidingly passes through the lumen and its ends. (Sleeve 246 is shown in FIG. 1A; for clarity of illustration, sleeve 246 is shown as transparent in FIG. 1B, and is not shown in FIG. 1C.) In this configuration, sealing element 190 is typically sized and shaped to be inserted into the incision through the heart wall, and to provide a blood-tight seal. Sleeve 246, if provided, occludes blood flow to provide the seal. For some applications, sleeve 246 promotes hemostasis. Optionally, filament or fiber is provided within sleeve 246 to promote hemostasis. For example, sleeve 246 may comprise Dacron, and/or may be coated and/or woven to facilitate clotting.

For some applications, collars 244 comprise a distal guide collar 244A and a proximal driver collar 244B, which optionally are components of or serve as anchor head 124. For some applications, a proximal end of anchor shaft 122 is fixed within proximal driver collar 244B, as shown in FIG. 1C, or within distal driver collar 244A, as shown in FIG. 3A for tissue anchor 300. For some applications, one or more of collars 244 are radiopaque or comprise a radiopaque marker. For some applications, proximal driver collar 244B is shaped so as to be removably coupleable with an anchor-deployment shaft, such as described regarding a helical tissue anchor in PCT Publication WO 2015/063580, which is incorporated herein by reference.

For some applications, a proximally-facing surface defined by tissue-coupling element 128 is convex when tissue anchor 200 is unconstrained by deployment tool 30, such as shown in FIGS. 1B and 1C. For other applications, a proximally-facing surface defined by tissue-coupling element 128 is concave when tissue anchor 200 is unconstrained by deployment tool 30, such as shown in FIG. 5B for tissue anchor 300

Figure 4B:
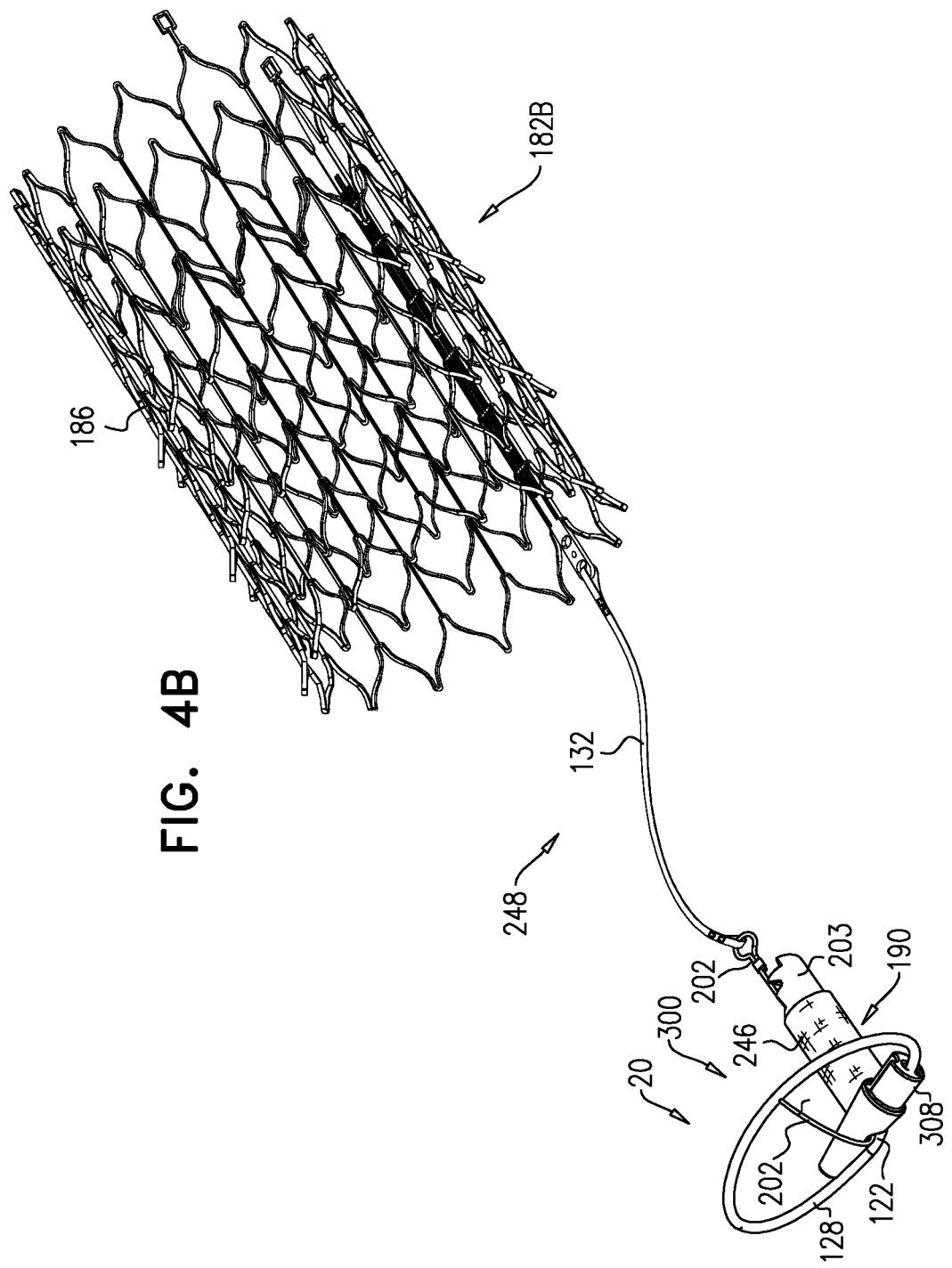

For some applications, such as shown in FIGS. 4A-B for tissue anchor 300 (described hereinbelow), one or more tethers 132 are provided, which are configured to be coupled to tissue anchor 200. Typically, the one or more tethers 132 are fixed to flexible elongate tension member 202, typically to proximal portion 208 of the tension member, such as at or near (e.g., within 1 cm of) a proximal end of proximal portion 208. When tension is applied to the one or more tethers, the tension is transmitted to flexible elongate tension member 202, rather than to anchor shaft 122 via anchor head 124. Typically, the one or more tethers are (a) fixed to the second tissue anchor and (b) not fixed to anchor shaft 122 of first tissue anchor 200.

For some applications, radially-inner end 264 of open loop 154 (e.g., spiral 160) is bent proximally, such as can be best seen in FIG. 1C. Because of the bend, radially-inner end 264 may help tissue-coupling element 128 resist rotation and uncoiling.

For some applications, when tissue anchor 200 is unconstrained by deployment tool 30, such as shown in FIGS. 1B-D, wire 150 (a) is shaped as an open loop 154 having more than one turn, such that a first complete turn of open loop 154 at least partially overlaps (i.e., runs alongside, above, and/or below) a second at-least-partial turn of open loop 154. For some applications, the first complete turn and the second at-least-partial turn radially coincide, i.e., are at a same distance as each other from a center point (configuration not shown). For other applications, as shown in the figures, an outermost turn of open loop 154 at least partially overlaps (i.e., runs alongside, above, and/or below) a second-to-outermost turn of open loop 154 (for example, an outermost turn 214 and a second-to-outermost turn 216 of open loop 154 are labeled in FIG. 1D). (As used in the present application, including in the claims, one turn equals 360 degrees. As used in the present application, including in the claims, "more than one turn" should not be understood as requiting at least two turns; instead, "more than one turn" also includes one turn plus a fraction of a turn, as described below. For example, for applications in which open loop 154 includes an outermost turn and a second-to-outermost turn, the second-to-outermost turn of open loop 154 may be a partial turn, such as shown in FIGS. 3A-C, 4A-B, 5A-D, 7, 8, 9A-F, 10E, 10G, 12, and 13A-E.)

For applications in which open loop 154 includes an outermost turn and a second-to-outermost turn, such as shown in FIG. 1D, open loop 154 has radially-outer end 164 and radially-inner end 264, which typically do not touch each other at least when tissue anchor 200 is unconstrained by deployment tool 30. For applications in which the first complete turn and the second at-least-partial turn radially coincide, the two opposite ends of the open loop typically do not touch each other at least when tissue anchor 200 is unconstrained by deployment tool 30. Open loop 154 is defined by an elongate path of wire 150 that winds more than one turn around center point 162 without forming a closed loop. The elongate path may include one or more curved segments and/or one or more straight segments, such as described hereinbelow with reference to FIG. 12. The path may fall in two dimensions, or may fall in three dimensions, in which case the open loop is a three-dimensional open loop, the elongate path of which winds around a center axis while moving parallel to the axis, without forming a closed loop.

For some applications, open loop 154 extends from distal end 130 of anchor shaft 122 at radially-outer end 164 of open loop 154. For some applications, wire 150 intersects center point 162 (labeled in FIG. 1D) when tissue anchor 200 is unconstrained by deployment tool 30 (configuration not shown), while for other applications, wire 150 does not intersect center point 162 (labeled in FIG. 1D) when tissue anchor 200 is unconstrained by deployment tool 30 (as shown).

For some applications, when tissue anchor 200 is unconstrained by deployment tool 30, such as shown in FIGS. 1B-D, wire 150 of open loop 154 is shaped as a spiral 160 (e.g., a three-dimensional spiral) around center point 162. For some of these applications, wire 150 of spiral 160 extends from distal end 130 of anchor shaft 122 at radially-outer end 164 of spiral 160. For some applications, wire 150 of spiral 160 intersects center point 162 when tissue anchor 200 is unconstrained by deployment tool 30 (configuration not shown), while for other applications, wire 150 of spiral 160 does not intersect center point 162 when tissue anchor 200 is unconstrained by deployment tool 30 (as shown). For some applications, spiral 160 is generally circular when tissue anchor 200 is unconstrained by deployment tool 30 (configuration not shown), while for other applications, spiral 160 is an elliptical spiral when the tissue anchor is unconstrained by deployment tool 30, such as shown in FIGS. 19-D.

As used in the present application, including in the claims, center point 162 is the centroid of projection 139 of tissue-coupling element 128 on plane 136. Typically, such as when tissue-coupling element 128 is shaped as a spiral, tissue-coupling element 128 is non-helical when tissue anchor 200 is unconstrained by deployment tool 30.

Reference is made to FIGS. 1A-D. For some applications, tissue anchor 200 is implanted using techniques described hereinbelow with reference to FIGS. 14A-D, 15A-C, and/or 16, optionally in combination with techniques described in one or more of the patents and patent application publications incorporated hereinbelow by reference, mutatis mutandis.

Reference is now made to FIGS. 2A-B and 3A-C, which are schematic illustrations of a tissue anchor 300 before (FIGS. 2A-B) and after (FIGS. 3A-C) deployment from deployment tool 30, in accordance with an application of the present invention. Tissue anchor 300 is one implementation of tissue anchor 20, described above. Other than as described below and shown in the figures, tissue anchor 300 is generally similar to tissue anchor 200, described hereinabove with reference to FIGS. 1A-D, and may implement any of the features thereof, mutatis mutandis.

For some applications, tissue-coupling element 128 comprises a tip 308, which is fixed to a distal end of wire 150, and has, at a widest longitudinal site 312 along tip 308 (labeled in FIG. 3C), a greatest tip outer cross-sectional area that equals at least 150% (e.g., at least 200%, or at least 300%) of an average wire cross-sectional area of wire 150 (The cross-sectional area of tip 308 is measured perpendicular to a central longitudinal axis 318 of tip 308. Similarly, the cross-sectional area of wire 150 is measured perpendicular to a central longitudinal axis of the wire, and is not a cross-sectional area of open loop 154.) Alternatively or additionally, for some applications, the greatest tip outer cross-sectional area is greater than 1 mm2, e.g., greater than 5 mm2, such as greater than 2 mm2. For some applications, tip 308 includes a frustoconical portion 314 (labeled in FIG. 3C).

Typically, tip 308 is shaped so as to define a guidewire lumen 316 therethrough. For some applications, central longitudinal axis 318 of tip 308 (a) passes through a distal end-opening 320 of guidewire lumen 316, and (b) does not pass through a proximal end-opening 322 of guidewire lumen 316. For some of these applications, a center 323 of distal end-opening 320 of guidewire lumen 316 is disposed within 1 mm of central longitudinal axis 318 of tip 308, e.g., center 323 falls on central longitudinal axis 318. Alternatively or additionally, for some of these applications, central longitudinal axis 318 of tip 308 passes through the distal end of wire 150.

In configurations in which tissue-coupling element 128 comprises tip 308, the tip temporarily serves as an atraumatic distal end of deployment shaft 34 of deployment tool 30 when the tip is removably coupled to a distal end 342 of deployment shaft 34 of deployment tool 30, as shown in FIGS. 2A-B. Thus, in these configurations, deployment tool 30 (including deployment shaft 34) is typically not shaped so as define sharp distal piercing tip 32.

For some applications, deployment shaft 34 of deployment tool 30 has a deployment-shaft outer cross-sectional area which equals between 90% and 110% (e.g., 100%) of the greatest tip outer cross-sectional area, and tip 308 is shaped so as to removably engage distal end 342 of deployment shaft 34, such as shown in FIGS. 2A-B, as well as in FIGS. 6A-B, described hereinbelow.

Although only the tissue anchors illustrated in FIGS. 2A-3C, 4A-B, 5A-D, 7, 9A-C, 10H, and 15A-C are shown comprising tip 308, the tissue anchors illustrated in FIGS. 1A-D, 9D-F, 10A-D, 10F, 12, 13A-E, 14A-D, and 16 may optionally also comprise tip 308 (such as described below with reference to FIG. 10H regarding FIGS. 10A-D and 10F).

Reference is now made to FIG. 3D, which is a schematic illustration of anchor head 124 of tissue anchor 300, in accordance with an application of the present invention. For clarity of illustration, flexible elongate tension member 202, wire 150 of tissue-coupling element 128, and guidewire 310 are not shown in FIG. 3D; these elements are shown inter alia in FIG. 3B. As mentioned above with reference to FIGS. 1A-D, for some applications, anchor head 124 comprises distal guide collar 244A and proximal driver collar 244B, which are optionally connected by a collar shaft 123.

For some applications, anchor head 124 (e.g., distal guide collar 244A thereof, as shown) is shaped so as to define:
- a first passage 330, in which proximal portion 208 of flexible elongate tension member 202 is slidably disposed,
- a second passage 332, in which a proximal portion of wire 150 of tissue-coupling element 128 is fixedly disposed, and
- a third passage 334, sized for slidable passage therethrough of guidewire 310.

First, second, and third passages 330, 332, and 334 have respective, different central longitudinal axes. The passages keep flexible elongate tension member 202, the proximal portion of wire 150, and guidewire 310 aligned with but separate from one another. For some applications, a proximal end 336 of second passage 332 is closed. For some applications, third passage 334 has an inner diameter of between 0.25 and 0.75 mm.

For some applications, distal guide collar 244A of anchor head 124 is shaped so as to define first, second, and third passages 330, 332, and 334, and proximal driver collar 244B of anchor head 124 to shaped so as to define:
- a fourth passage 338, (a) in which proximal portion 208 of flexible elongate tension member 202 is slidably disposed, and (b) which is optionally coaxial with first passage 330 (as shown), and/or
- a fifth passage 339, (a) which is sized for slidable passage therethrough of guidewire 310, and (b) which is optionally coaxially with third passage 334 (as shown).

For some applications, when tissue anchor 300 (and open loop 154 (e.g., spiral 160) thereof) is unconstrained by deployment tool 30, open loop 154 (e.g., spiral 160) has a first outer dimension, measured in a direction parallel to flexible elongate tension member 202. After tension is applied to flexible elongate tension member 202, flexible elongate tension member 202 becomes more narrow in the direction of flexible elongate tension member 202, such that open loop 154 (e.g., spiral 160) has a second outer dimension, measured in a direction parallel to flexible elongate tension member 202, which is less than the first outer dimension, e.g., no more than 90% of the first out dimension, such as no more than 80% of the first out dimension, e.g., no more than 70% of the first out dimension, no more than 50% of the first out dimension, or no more than 20% of the first out dimension. For some applications, the force applied to flexible elongate tension member 202 to achieve this reduction is between 2 and 50 N, such as between 5 and 20 N, e.g., 5 N, 7 N, 10 N, 20 N, or 30 N.

The amount of force is dependent on the radius of wire 150, and may increase as a power of the radius, such as a third or fourth power of the radius. For some applications, a smallest radius of wire 150 is chosen that is able to withstand between 5 and 20 N of force.

Reference is now made to FIGS. 4A-B, which are schematic illustrations of two configurations of a tissue anchor system 248, in accordance with respective applications of the present invention. In these applications, tissue anchor 300 is a first tissue anchor 182A of tissue anchor system 248, which further comprises (a) a second tissue anchor 182B, which is separate and distinct first tissue anchor 182A, and (b) the one or more tethers 132, which are configured to couple (i) flexible elongate tension member 202 of first tissue anchor 182A to (ii) second tissue anchor 182B. For some applications, one of the one or more tethers 132 is fixed to (a) flexible elongate tension member 202 of first tissue anchor 182A and (b) second tissue anchor 1829.

For some applications, such as shown in FIG. 4A, second tissue anchor 1829 comprises a helical tissue-coupling element 184. For example, second tissue anchor 182B may implement techniques described in PCT Publication WO 2015/193728 (e.g., with reference to FIG. 8 thereof), PCT Publication WO 2014/108903, and/or the patents and patent application publications incorporated hereinbelow by reference. For other applications, such as shown in FIG. 4B, second tissue anchor 182B comprises a stent 186. For example, second tissue anchor 182B may implement techniques described in one or more of the following applications, which are incorporated herein by reference: US Patent Application Publication 2011/0184510, US Patent Application Publication 2012/0035712, US Patent Application Publication 2013/0018459, US Patent Application Publication 2013/0046380, PCT Publication WO 2014/141239, and/or the patents and patent application publications incorporated hereinbelow by reference.

Reference is made to FIGS. 1A-D, 3A, and 4A-B. For some applications, anchor shaft 122 comprises sealing element 190, which is configured to form a blood-tight seal between a portion of anchor shall 122 inside the heart chamber and wall 194 of the heart. For some applications, sealing element 190 is annular, and snugly surrounds anchor shaft 122.

Figure 5A:
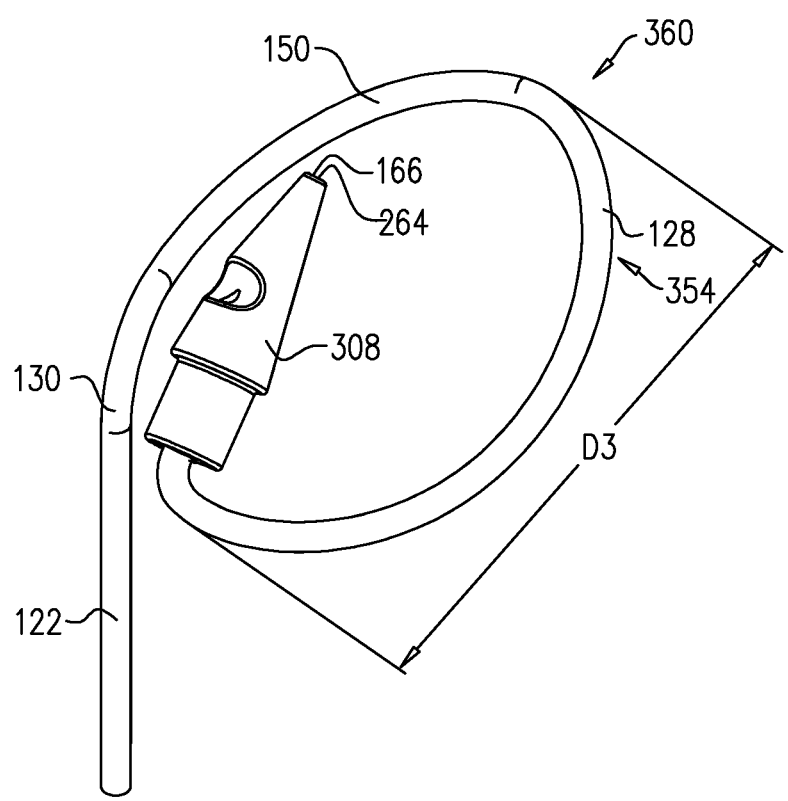
FIGS. 5A-B are schematic illustrations of a tissue-coupling element and an anchor shaft of the tissue anchor of FIGS. 2A-3C, in accordance with an application of the present invention.
Figure 5B:
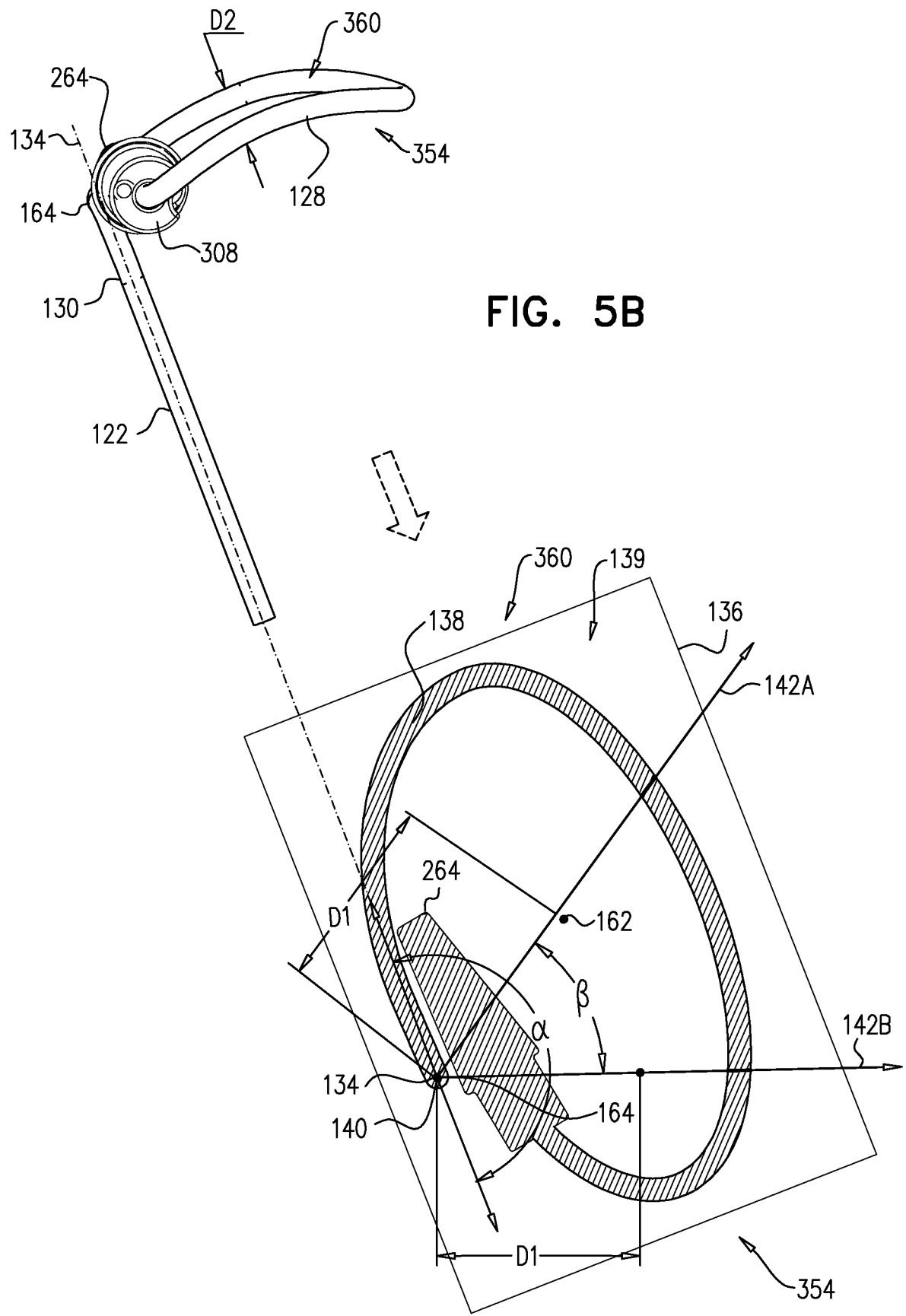

Reference is now made to FIGS. 5A-B, which are schematic illustrations of tissue-coupling element 128 and anchor shaft 122, in accordance with an application of the present invention. FIGS. 5A-B provide two views of a configuration tissue-coupling element 128 and anchor shaft 122, when tissue anchor 300 is unconstrained by deployment tool 30. The parameters of open loop 354 of tissue anchor 300 described with reference to FIGS. 5A-B may also apply to open loop 154 of tissue anchor 200, described hereinabove with reference to FIGS. 1A-D.

Reference is made to FIGS. 3A-C and 5A-D. When tissue anchor 300 is unconstrained by deployment tool 30, such as shown in FIGS. 3A-C and 5A-D:
  anchor shaft 122 has central longitudinal axis 134,
  anchor head 124 is coaxial with central longitudinal axis 134, and
  tissue-coupling element 128 is shaped such that if tissue-coupling element 128 were to be projected onto a plane 136 that is perpendicular to central longitudinal axis 134:
    at least 80% (e.g., at least 90%, such as at least 95%) of an area 138 of a projection 139 of tissue-coupling element 128 on plane 136 would fall within a first angle α (alpha) of 180 degrees in plane 136 having a vertex 140 at central longitudinal axis 134, as labeled in FIG. 2B, and
    area 138 would partially overlap, at a distance D1 of at least 3 mm from vertex 140, both rays 142A and 142B of a second angle β (beta) of between 45 and 180 degrees in plane 136 having vertex 140 at central longitudinal axis 134 (the partial overlap is illustrated by the heavier portions of the rays).

As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

Tissue-coupling element 128 is configured to have a predetermined shape when unconstrained by deployment tool 30. For example, the tissue-coupling element may comprise a shape-memory material, such as a shape-memory alloy, e.g., Nitinol. Thus, tissue-coupling element 128 automatically transitions to the predetermined shape when released from being constrained by deployment tool 30 to being unconstrained by deployment tool 30.

For some applications, central longitudinal axis 134 is straight when tissue anchor 300 is unconstrained by deployment tool 30, such as shown in FIGS. 3A-C and 5A-D.

For some applications, such as shown in FIGS. 3A-C and 5A-B, a proximally-facing surface defined by tissue-coupling element 128 (i.e., the surface defined by tissue-coupling element 128 that is configured to touch the external surface of the heart) is concave when tissue anchor 300 is unconstrained by deployment tool 30 (in other words, tissue-coupling element 128 is concave when viewed from proximal portion 126 of anchor shaft 122). Such a concave shape may approximate the natural convex shape of an external surface of the wall of the heart.

For other applications, the proximally-facing surface defined by tissue-coupling element 128 is generally flat, when tissue anchor 300 is unconstrained by deployment tool 30 (configuration not shown). Optionally, upon coming into full contact with the external surface of the heart, the proximally-facing surface defined by the tissue-coupling element may assume a concave shape conforming to the convex shape of the external surface of the heart.

For some applications, when tissue anchor 300 is unconstrained by deployment tool 30:
  a greatest longitudinal dimension D2 of tissue-coupling element 128, measured parallel to central longitudinal axis 134, is between 1 and 6 mm (such as between 2 and 5 mm) (labeled in FIG. 5B), and
  a greatest lateral dimension D3 of tissue-coupling element 128, measured perpendicular to central longitudinal axis 134, is between 4 and 25 mm (such as between 5 and 20 mm) (labeled in FIG. 5A).

Typically, a ratio of the greatest longitudinal dimension D2 and greatest lateral dimension D3 is between 1:2 and 1:18, such as between 1:5 and 1:10, e.g., 1:7 when tissue anchor 300 is unconstrained by deployment tool 30.

For some applications, tissue-coupling element 128 has a length of at least 5 mm (e.g., at least 10 mm), no more than 100 mm (e.g., no more than 60 mm), and/or between 5 and 100 mm (e.g., between 10 and 60 mm) when constrained into a straight configuration.

For some applications, when tissue anchor 300 is unconstrained by deployment tool 30, such as shown in FIGS. 3A-C and 5A-D, tissue-coupling element 128 (including wire 150 and tip 308) (a) is shaped as open loop 354 having more than one turn, such that a first complete turn of open loop 354 at least partially overlaps (i.e., runs alongside, above, and/or below) a second at-least-partial turn of open loop 354. For some applications, the first complete turn and the second at-least-partial turn radially coincide, i.e., are at a same distance as each other from a center point (configuration not shown). For other applications, as shown in the figures, an outermost turn of open loop 354 at least partially overlaps (i.e., runs alongside, above, and/or below) a second-to-outermost turn of open loop 354. For some applications, open loop 354 is a three-dimensional open loop. For some applications, open loop 354 is a spiral 360 (e.g., a three-dimensional spiral).

For some applications, open loop 354 extends from distal end 130 of anchor shaft 122 at radially-outer end 164 of open loop 354. For some applications, wire 150 intersects center point 162 (labeled in FIG. 3C) when tissue anchor 300 is unconstrained by deployment tool 30 (configuration not shown), while for other applications, wire 150 does not intersect center point 162 (labeled in FIG. 3C) when tissue anchor 300 is unconstrained by deployment tool 30 (as shown).

For some applications, such as shown in FIGS. 3A-C and 5A-D (as well as FIGS. 4A-B, 7, 9A-C, and 15A-C), when tissue anchor 300 is unconstrained by deployment tool 30, open loop 354 has more than one turn and less than two turns. For example, as shown in FIGS. 3A-C and 5A-D, open loop 354 may have more than one turn and less than 1.5 turns, such as more than one turn, e.g., more than 1.01 turns (363.6 degrees), such as more than 1.02 turns (367.2 degrees), and/or less than 1.25 turns (450 degrees).

For some applications, when tissue anchor 300 is unconstrained by deployment tool 30, such as shown in FIGS. 3A-C and 5A-D, tissue-coupling element 128 (including wire 150 and tip 308 if provided) of open loop 354 is shaped as spiral 160 (e.g., a three-dimensional spiral) around center point 162. For some of these applications, wire 150 of spiral 160 extends from distal end 130 of anchor shaft 122 at radially-outer end 164 of spiral 160. For some applications, wire 150 of spiral 160 intersects center point 162 when tissue anchor 300 is unconstrained by deployment tool 30 (configuration not shown), while for other applications, wire 150 of spiral 160 does not intersect center point 162 when tissue anchor 300 is unconstrained by deployment tool 30 (as shown). For some applications, spiral 160 is an elliptical spiral when the tissue anchor is unconstrained by deployment tool 30, such as shown in FIGS. 3A-C and 5A-D (as well as in FIGS. 4A-B, 7, 9A-C, and 15A-C).

For some applications, such as shown in FIGS. 3A-C and 5A-D (as well as FIGS. 4A-B, 7, 9A-C, and 15A-C), when the tissue anchor is unconstrained by deployment tool 30, spiral 160 has more than one turn and less than two turns. For example, as shown in FIGS. 3A-C and 5A-D, spiral 160 may have more than one turn and less than 1.5 turns, such as more than one turn and less than 1.25 turns.

For some applications, when tissue anchor 300 is unconstrained by deployment tool 30, the open loop (e.g., the spiral) has greatest lateral dimension D3 (labeled in FIG. 5A), measured perpendicular to central longitudinal axis 134, and a distance between (a) radially-outer end 164 of open loop 354 (e.g., spiral 160) and (b) a radially-inner-most point 166 of open loop 354 (e.g., spiral 160), measured perpendicular to central longitudinal axis 134, is equal to at least 30% of the greatest lateral dimension D3. Alternatively or additionally, for some applications, a distance between radially-inner-most point 166 and a closest point thereto on an outermost turn of open loop 354, measured perpendicular to central longitudinal axis 134, is equal to at least 30% of the greatest lateral dimension D3.

Figure 5C:
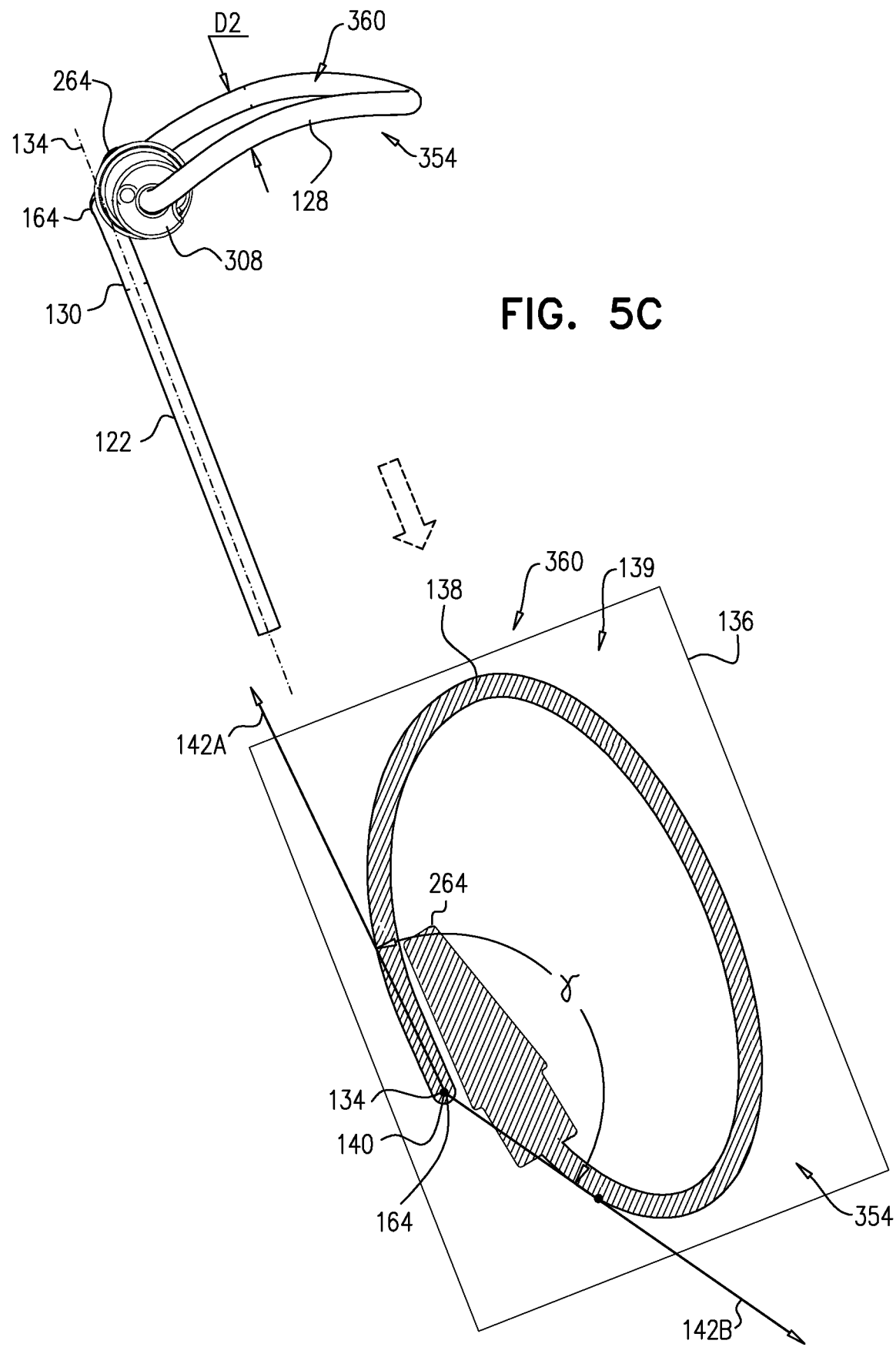
FIGS. 5C-D are schematic illustrations of a tissue-coupling element and an anchor shaft of the tissue anchor of FIGS. 2A-3C, in accordance with respective applications of the present invention.
Figure 5D:
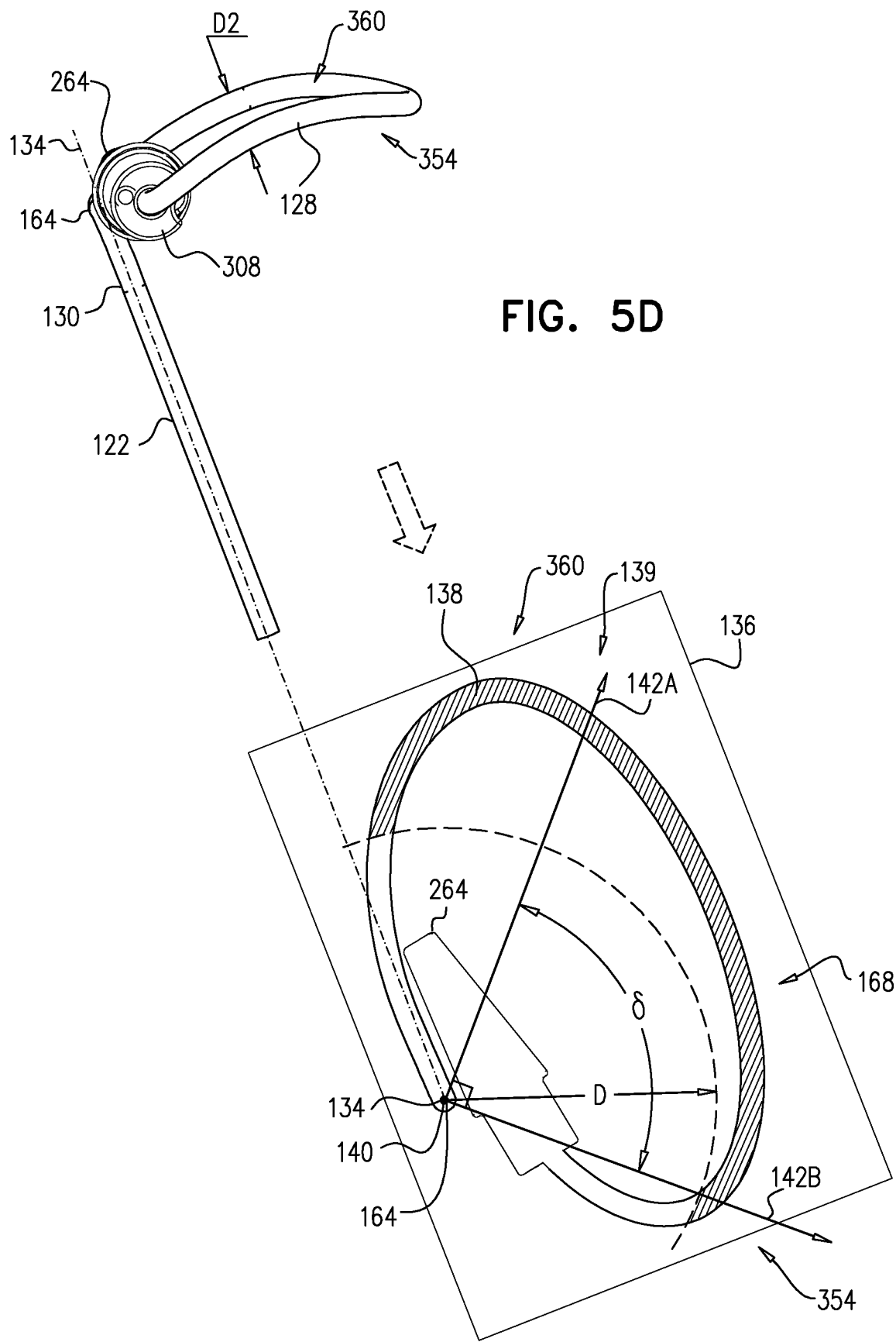

Reference is made to FIGS. 5C-D, which are schematic illustrations of tissue-coupling element 128 and anchor shaft 122, in accordance with respective applications of the present invention. The parameters of open loop 354 of tissue anchor 300 described with reference to FIGS. 5C-D may also apply to open loop 154 of tissue anchor 200, described hereinabove with reference to FIGS. 1A-D. For some applications, as shown in FIG. 5C, at least 80%, such as at least 90%, e.g., at least 95%, of area 138 of projection 139 of tissue-coupling element 128 on plane 136 would fall within a third angle γ (gamma) of 150 degrees in plane 136 having vertex 140 at central longitudinal axis 134, if tissue-coupling element 128 were to be projected onto plane 136.

For some applications, as shown in FIG. 5D, an outer portion 168 of area 138 of projection 139 of tissue-coupling element 128 on plane 136 consists of all points of area 138 at least a distance D from vertex 140; for example, the distance D may be 2 mm, such as 3 mm, e.g., 4 mm. Outer portion 168 would fall within all angular positions of a fourth angle δ (delta) of 90 degrees in plane 136 having vertex 140 at central longitudinal axis 134, which outer portion 168, if tissue-coupling element 128 were to be projected onto plane 136. In other words, at all angular positions of fourth angle δ (delta), there is at least one point of outer portion 168. (Outer portion 168 may additionally fall within angular positions outside of fourth angle δ (delta), such as shown in FIG. 5D.)

Reference is now made to FIGS. 6A-B, which are schematic illustrations of a tissue anchor 400 before deployment from deployment tool 30, in accordance with an application of the present invention. Tissue anchor 400 is one implementation of tissue anchor 20, described above. Other than as described below and shown in the figures, tissue anchor 400 is generally similar to tissue anchor 300, described hereinabove with reference to FIGS. 2A-B, 3A-D, 4A-B, and 5A-D, and may implement any of the features thereof, mutatis mutandis.

In the configuration shown in FIGS. 6A-B, guidewire 310, rather than passing through deployment shaft 34 of deployment tool 30 alongside wire 150 of tissue-coupling element 128 (as shown in FIGS. 2A-B), exits deployment shaft 34 near distal end 342 of deployment shaft 34, typically through a guidewire opening 344 (e.g., slot) that is defined by the wall of deployment shaft 34 and extends to distal end 342 of deployment shaft 34. Optionally, deployment tool 30 further comprises a guide tube 346, which is fixed to an external surface of deployment tool 30; guidewire 310 passes through guide tube 346. In addition, in the configuration shown in FIGS. 6A-B, anchor head 124 typically is not shaped so as to define third passage 334 (described hereinabove with reference to FIG. 3D), because guidewire 310 does not pass through anchor head 124.

Reference is now made to FIG. 7, which is a schematic illustration of a tissue anchor 430, in accordance with an application of the present invention. Tissue anchor 430 is one implementation of tissue anchor 20, described above. Other than as described below, tissue anchor 430 is generally similar to tissue anchor 300, described hereinabove with reference to FIGS. 2A-B, 3A-D, 4A-B, and 5A-D, and may implement any of the features thereof, mutatis mutandis. In addition, tissue anchor 430 may implement any of the features of tissue anchor 200, described hereinabove with reference to FIGS. 1A-D, mutatis mutandis, and/or tissue anchors 340, 350, 430, 370, 400, 420, 470, and/or 490, mutatis mutandis.

Tissue-coupling element 128 of tissue anchor 430 comprises wire 150, which is shaped as an open loop 256, e.g., a spiral 260. Wire 150 extends from distal end 130 of anchor shaft 122 at a radially-inner end 264 of open loop 256 (e.g., spiral 260), when tissue anchor 220 is unconstrained by deployment tool 30. This is unlike the typical configurations of open loop 154 (e.g., spiral 160) and open loop 354 (e.g., spiral 360), described hereinabove, in which wire 150 extends from distal end 130 of anchor shaft 122 at radially-outer end 164 of the open loop (e.g., the spiral). In the present configurations, when tissue anchor 430 is unconstrained by deployment tool 30, radially-inner end 264 of open loop 256 (e.g., spiral 260) is typically disposed within 15 mm of center point 162, such as coinciding with center point 162.

Typically, tissue anchor 430 comprises exactly one flexible elongate tension member 202, which includes:
  distal portion 204 that is fixed to site 206 on open loop 256 (e.g., spiral 260),
  longitudinal segment 209 of proximal portion 208 that runs alongside the at least a portion 210 of anchor shaft 122 (labeled, for example, in FIG. 3B), and
  crossing portion 212, which (a) is disposed between distal and proximal portions 204 and 208 (labeled, for example, in FIG. 3B) along flexible elongate tension member 202, and (ii) crosses at least a portion of open loop 256 (e.g., spiral 260) when tissue anchor 430 is unconstrained by deployment tool 30.

For some applications, as shown, site 206 is on outermost turn 214 of open loop 256 (e.g., spiral 260), when tissue anchor 430 is unconstrained by deployment tool 30. Flexible elongate tension member 202 may implement any of the features described hereinabove with reference to FIGS. 1A-5D, mutatis mutandis.

Figure 8:
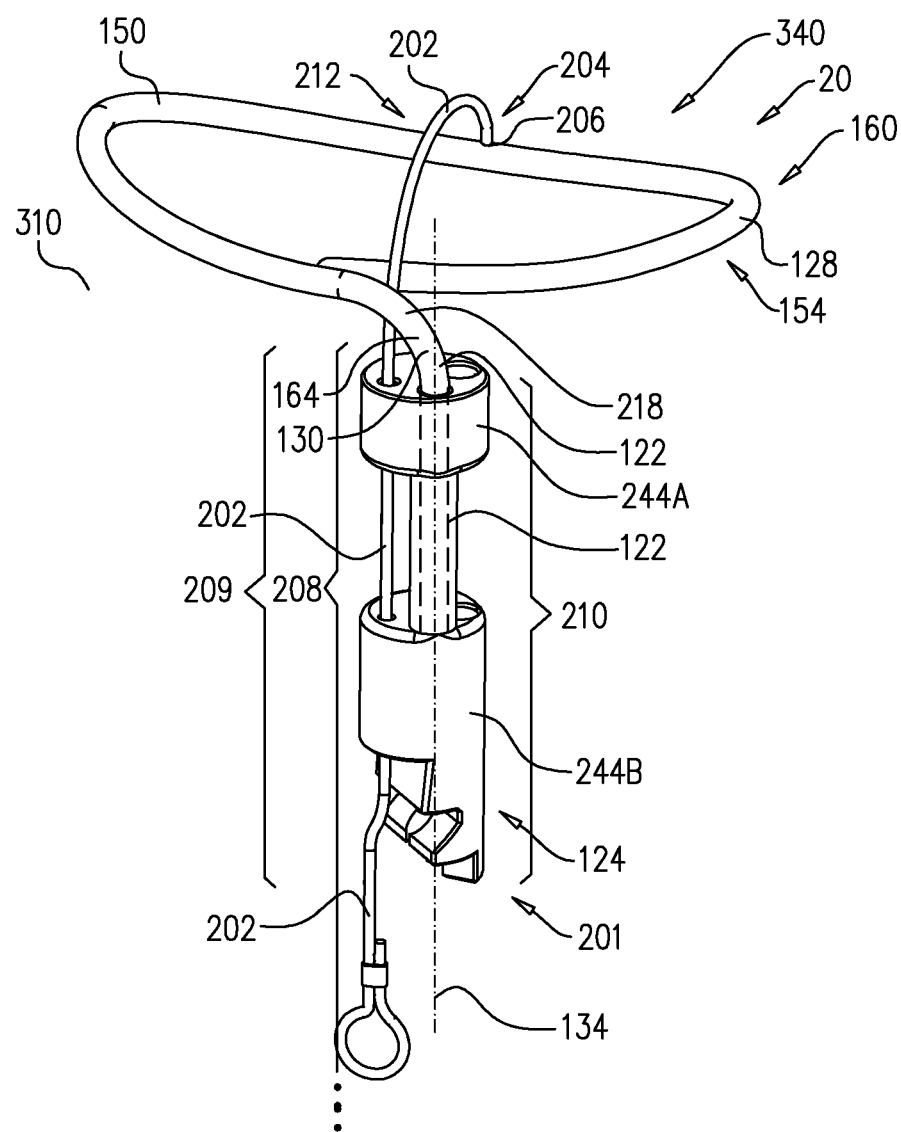
FIG. 8 is a schematic illustration of another tissue anchor after deployment from a deployment tool, in accordance with an application of the present invention.

Reference is now made to FIG. 8, which is a schematic illustration of a tissue anchor 340 after deployment from deployment tool 30, in accordance with an application of the present invention. Tissue anchor 340 is one implementation of tissue anchor 20, described above. Other than as described below and shown in the figures, tissue anchor 340 is generally similar to tissue anchor 300, described hereinabove with reference to FIGS. 2A-B, 3A-D, 4A-B, and 5A-D, and may implement any of the features thereof, mutatis mutandis. Tissue anchor 340, unlike tissue anchor 300, does not comprise tip 308; therefore, tissue anchor 340 is typically delivered using deployment shaft 34 having sharp distal piercing tip 32, as described hereinabove with reference to FIG. 1A.

Reference is made to FIGS. 9A-F, which are schematic illustrations of alternative ways to fix flexible elongate tension member 202 to site 206 of open loop 154 or open loop 354, in accordance with respective applications of the present invention. These techniques may be used in combination with any of the configurations of tissue anchor 20 described herein.

Figure 9A:
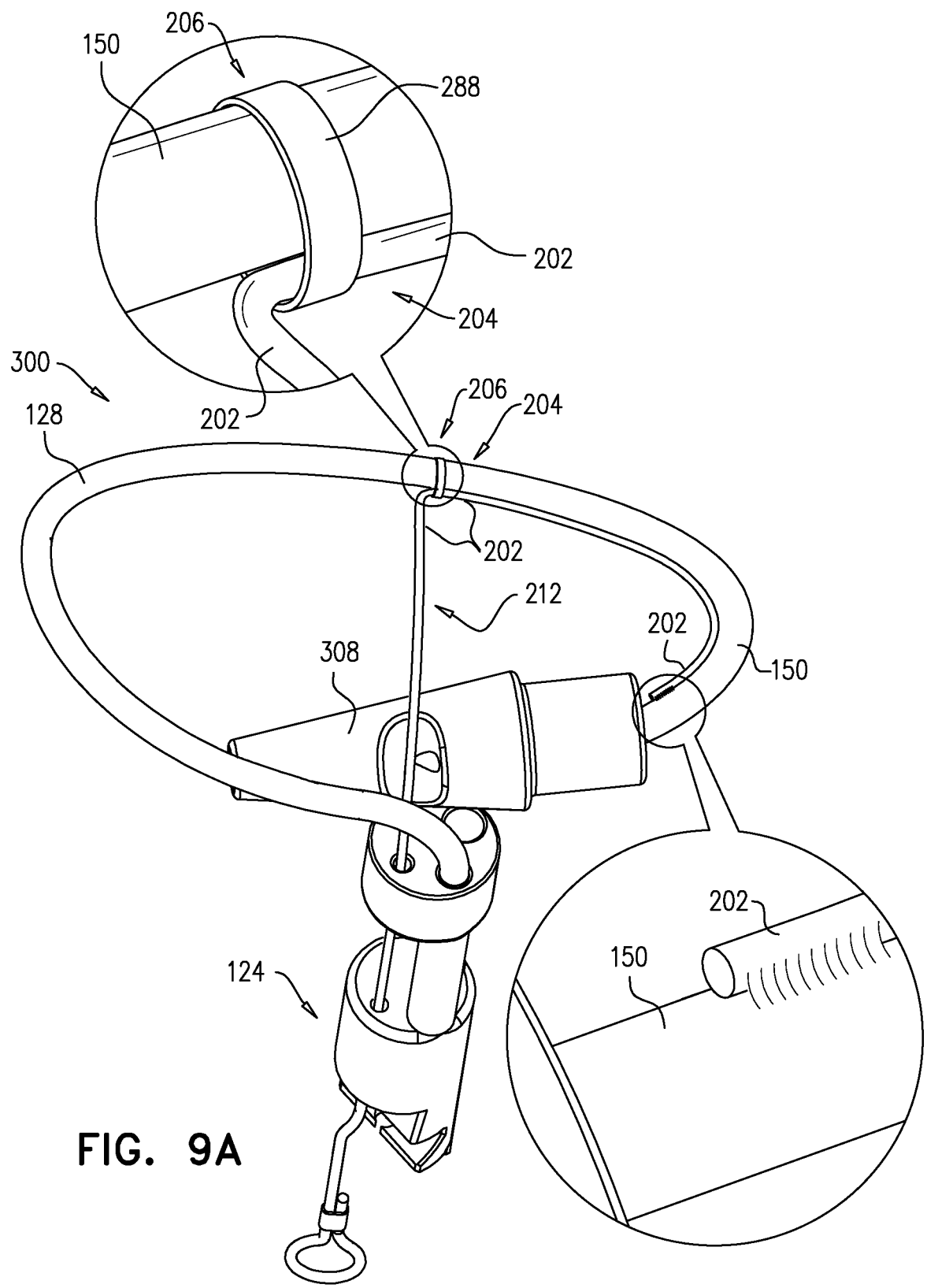
FIGS. 9A-F are schematic illustrations of alternative ways to fix a flexible elongate tension member to a site of an open loop of a tissue anchor, in accordance with respective applications of the present invention.

In the configuration shown in FIG. 9A, distal portion 204 of flexible elongate tension member 202 is fixed to site 206 on open loop 354 by crimping a crimping element 288 around wire 150. In this configuration, a distal portion of flexible elongate tension member 202 beyond site 206 is fixed (e.g., by welding or soldering) to open loop 354, such as near radially-inner end 264 of open loop 354. Distal portion 204 of flexible elongate tension member 202 at least partially runs along open loop 354 between site 206 (on open loop 354) and tip 308. The portion of flexible elongate tension member 202 between site 206 and radially-inner end 264 may be attached to wire 150, or may be held near wire 150, such as by a sleeve, as described with reference to FIG. 9E. It is noted that site 206 is the site on open loop 354 at which flexible elongate tension member 202 makes functional contact with the loop for applying tension across the loop, rather than other sites along wire 150 to which flexible elongate tension member 202 may also be attached.

Although the techniques of FIG. 9A are illustrated for open loop 354 of tissue anchor 300, these techniques may also be practiced with the other tissue anchors described herein, including with open loop 154 of tissue anchor 200, described hereinabove with reference to FIGS. 1A-D.

Figure 9B:
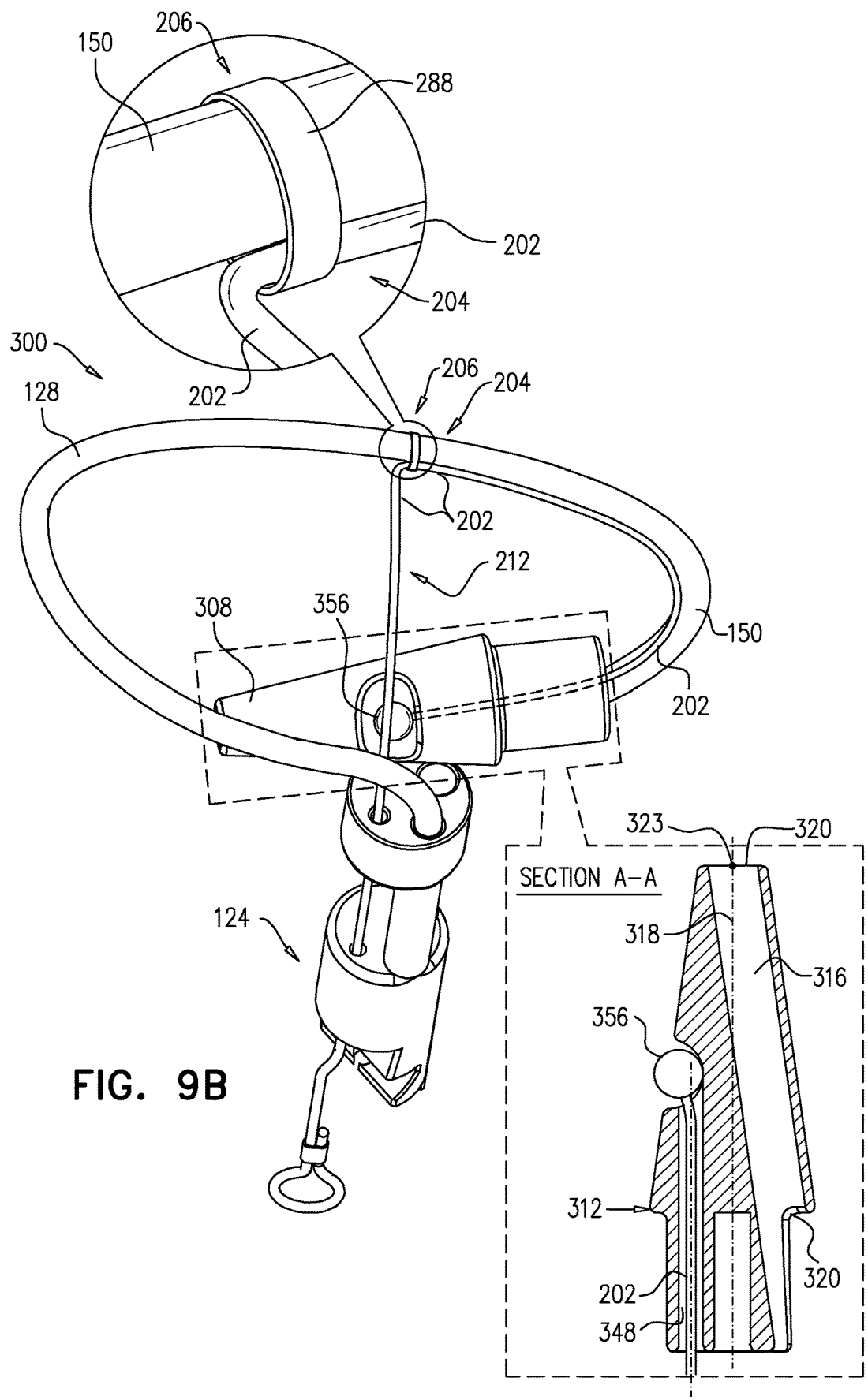

The configuration shown in FIG. 9B is generally similar to the configuration shown in FIG. 9A, except that in the configuration shown in FIG. 9B, distal portion 204 of elongate tension member 202, at one or more locations along distal portion 204, is fixed to tip 308. For some applications, tip 308 is shaped so as to define a tension-member lumen 348 therethrough, and distal portion 204 of flexible elongate tension member 202 passes through at least a portion of tension-member lumen 348. For some applications, flexible elongate tension member 202 is fixed to tip 308 by a bead 356 soldered to a distal end of flexible elongate tension member 202.

Figure 9C:
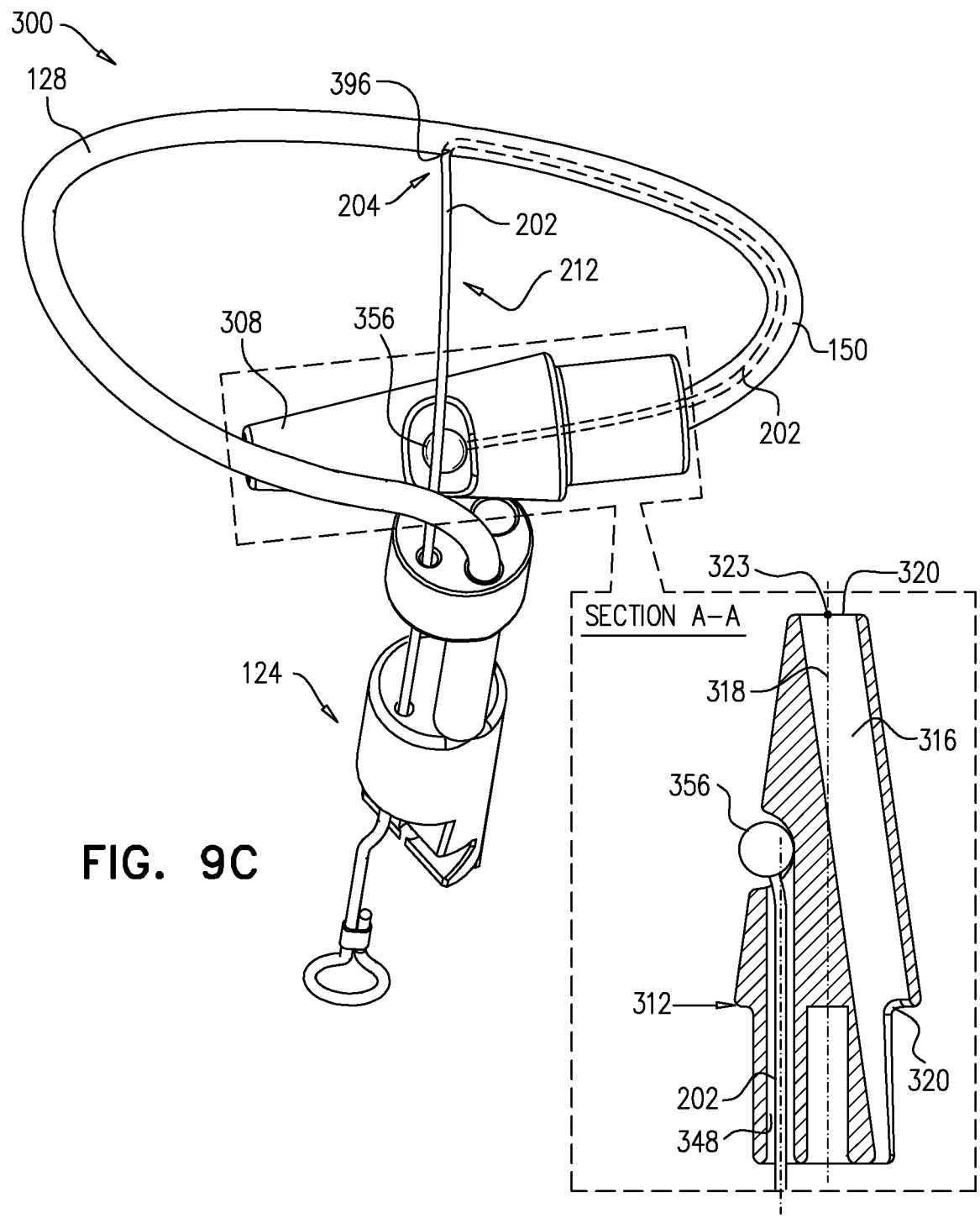

The configuration shown in FIG. 9C is generally similar to the configuration shown in FIG. 9B, except that in the configuration shown in FIG. 9C, wire 150 is shaped so as to define a channel (i.e., wire 150 is tubular), and the channel is shaped so as to define a lateral opening 396 at site 206. Distal portion 204 of flexible elongate tension member 202 enters the channel through lateral opening 396 at site 206, passes through the channel, and exits wire 150 at distal end 294 of wire 150.

Figure 9D:
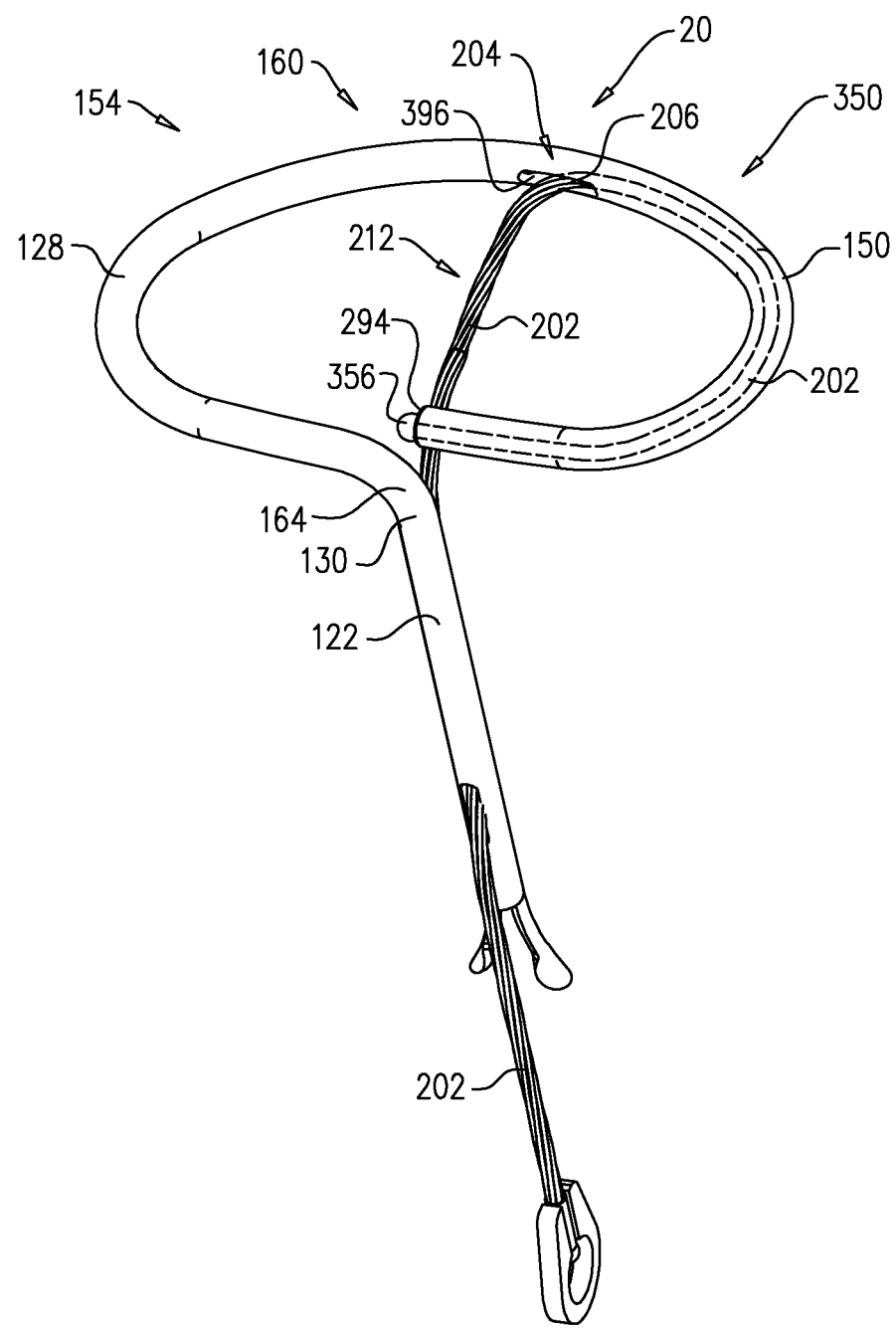

FIG. 9D is a schematic illustration of a tissue anchor 350, in accordance with an application of the present invention. Tissue anchor 350 is one implementation of tissue anchor 20, described above. Tissue anchor 350 is generally similar to the configuration of tissue anchor 300 shown in FIG. 9C, except as follows. Like the configuration shown in FIG. 9C, wire 150 is shaped so as to define a channel which has lateral opening 396 at site 206. Distal portion 204 of flexible elongate tension member 202 enters the channel through lateral opening 396 at site 206, passes through the channel, and exits wire 150 at distal end 294 of wire 150. For some applications, flexible elongate tension member 202 is fixed to distal end 294 of wire by bead 356 soldered to a distal end of flexible elongate tension member 202.

Figure 9E:
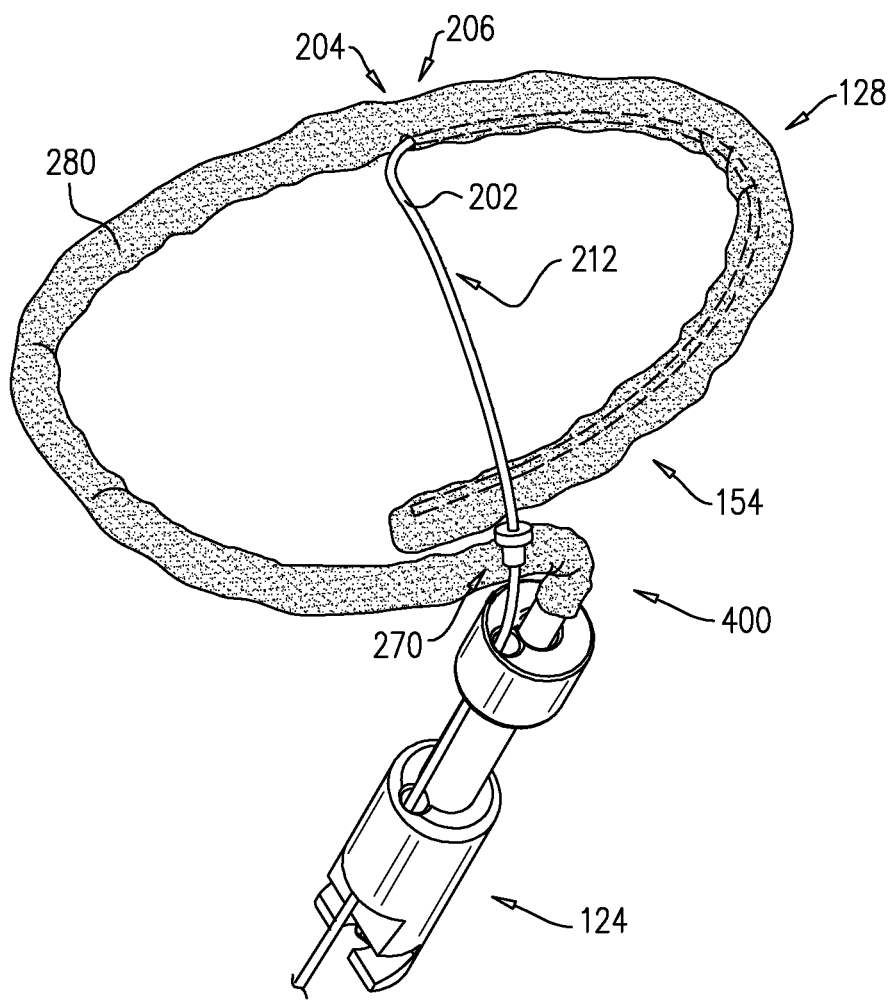

The configuration shown in FIG. 9E may be used in combination with the configuration shown in FIG. 9A, 9B, 9C, or 9D, or separately. In the configuration shown in FIG. 9E, open loop 154 is covered with a sleeve 280, which may comprise a woven material, comprising, for example, polyester. A distal portion of flexible elongate tension member 202 beyond site 206 is fixed (e.g., by welding or soldering) to open loop 154, such as near radially-inner end 264 of open loop 154 (this area of open loop 154 may facilitate attachment because this area is straighter than other portions of the open loop). Flexible elongate tension member 202 penetrates and exits sleeve 280 at site 206, such as by passing between the fibers of sleeve 280, or through an opening made in sleeve 280, which opening is optionally reinforced. Distal portion 204 of flexible elongate tension member 202 is fixed to site 206 on open loop 154 indirectly by being restrained by sleeve 280. Sleeve 280 may in addition improve tissue growth on the tissue anchor. Optionally, a more proximal portion of flexible elongate tension member 202, after crossing open loop 154, re-enters sleeve 280 through a lateral wall of the sleeve, and exits the proximal end of the sleeve.

Figure 9F:
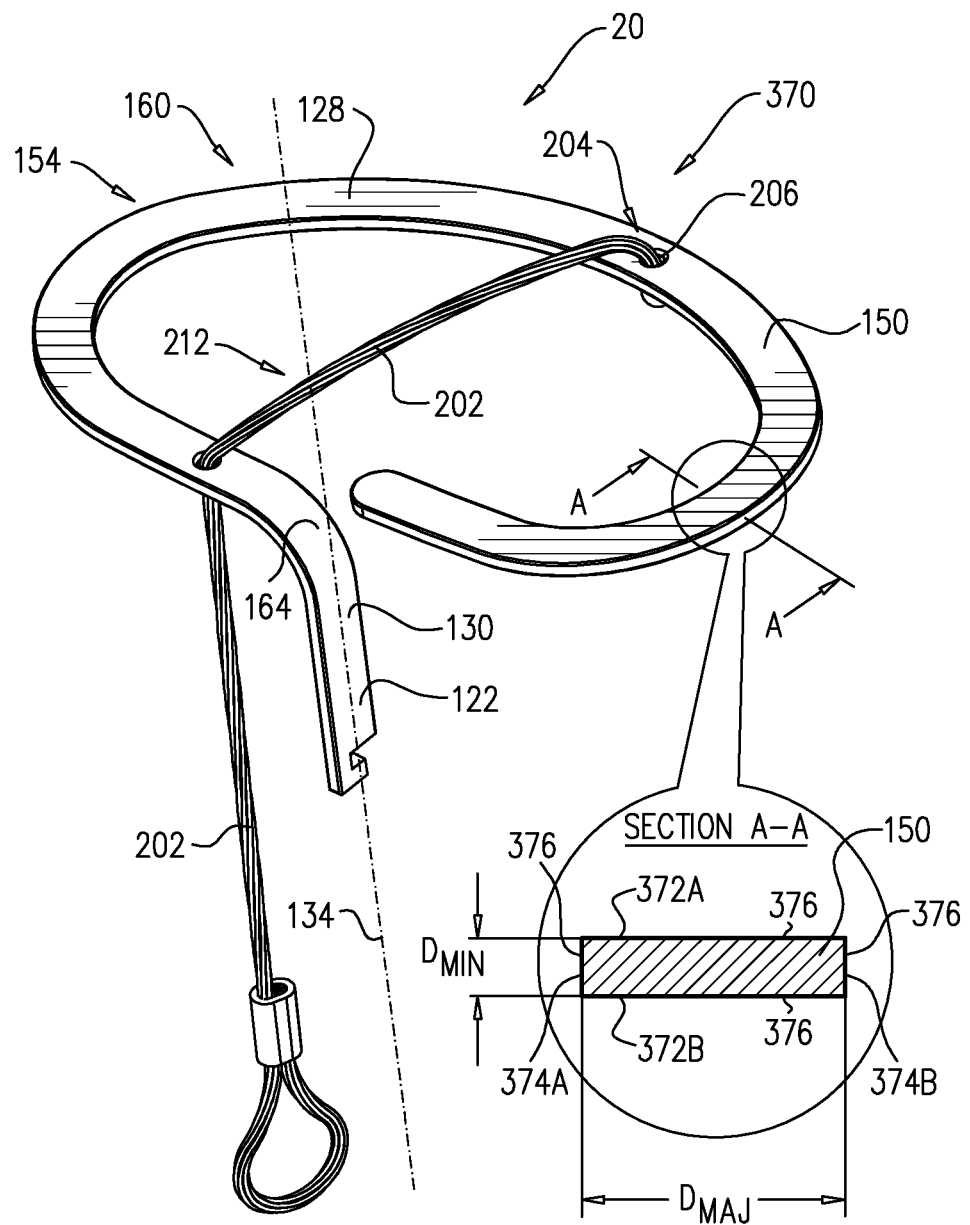

FIG. 9F is a schematic illustration of a tissue anchor 370, in accordance with an application of the present invention. Tissue anchor 370 is one implementation of tissue anchor 20, described above. Tissue anchor 370 is similar in some respect to tissue anchor 340, described hereinabove with reference to FIG. 8, and may implement any features thereof mutatis mutandis. Tissue anchor 370 optionally does not comprise anchor head 124, as shown; alternatively, tissue anchor 370 does comprise anchor head.

For some applications, wire 150 of tissue anchor 370 is shaped so as to define first and second major opposing surfaces 372A and 372B connected by first and second minor opposing surfaces 374A and 374B. First and second major opposing surfaces 372A and 372B and first and second minor opposing surfaces 374A and 374B extend along at least 90% of a total length of wire 150. A total surface area of first minor opposing surface 374A is less than 20%, e.g., less than 10%, such as less than 5%, of a total surface area of major opposing surface 372A.

Alternatively or additionally, for some applications, extending along at least 90% of a total length of wire 150, wire 150 has a greatest major dimension $D_{MAJ}$ and a greatest minor dimension $D_{MIN}$ perpendicular to the greatest major dimension $D_{MAJ}$. The greatest major dimension $D_{MAJ}$ equals at least 150% (e.g., at least 200%, such as at least 300%) of the greatest minor dimension $D_{MIN}$.

Alternatively or additionally, for some applications, at a plurality of locations along wire 150, a cross section of wire 150, taken perpendicular to a longitudinal axis of wire 150, has a shape that has at least one straight side 376, such as at least two straight sides 376, at least three straight sides 376, or four straight sides 376 (as shown). For some applications, the at least one straight side 376 has a length of at least 3 mm. (It is noted that the longitudinal axis of wire 150 typically includes one or more curved portions, such as shown in FIG. 9F.)

Reference is still made to FIG. 9F. For some applications, when the tissue anchor 370 is unconstrained by deployment tool 30: (a) a greatest longitudinal dimension of an open shape 291 (e.g., open loop 154), measured in parallel to a central longitudinal axis of anchor shaft 122, is between 0.25 and 5 mm, e.g., between 1 and 5 mm, and (b) a greatest lateral dimension of open shape 291 (e.g., open loop 154), measured perpendicular to the central longitudinal axis, is between 4 and 20 mm.

Figure 10A:
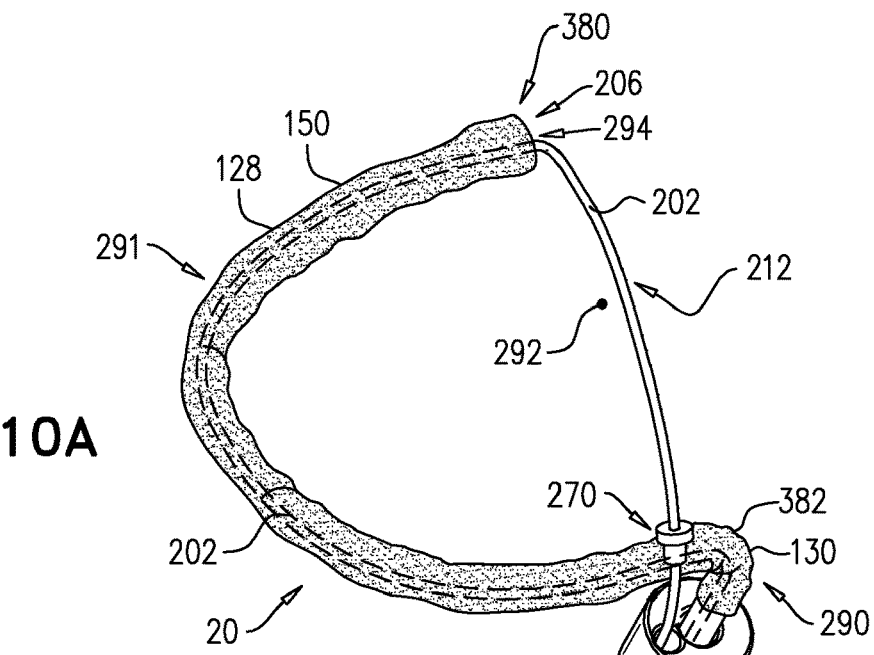

Reference is now made to FIGS. 10A-H, which are schematic illustrations of respective configurations of tissue anchor 20, in accordance with respective applications of the present invention. Tissue anchor 20 may have any of the characteristics described herein, mutatis mutandis. In these configurations of tissue anchor 20, tissue-coupling element 128 (e.g., wire 150 thereof, as shown in FIGS. 10A-G, or wire 150 and tip 308 thereof together, as shown in FIG. 10H) is shaped as open shape 291, such as open loop 154, when tissue anchor 20 is unconstrained by deployment tool 30. Flexible elongate tension member 202 extends from a distal site 380 on open shape 291 (in other words, site 206 is distal site 380), distal site 380 located within 7 mm (e.g., within 3 mm) of distal end 294 of open shape 291, such as at distal end 294, as shown in FIGS. 10A, 10B, 10C, and 10D). Alternatively or additionally, distal site 380 is located within a distance of distal end 294 of open shape 291, which distance equals 5% of a total length of wire 150, and/or equals 10% of greatest lateral dimension D3 of tissue-coupling element 128, measured perpendicular to central longitudinal axis 134 (labeled inter alia in FIG. 8A).

Figure 3B:
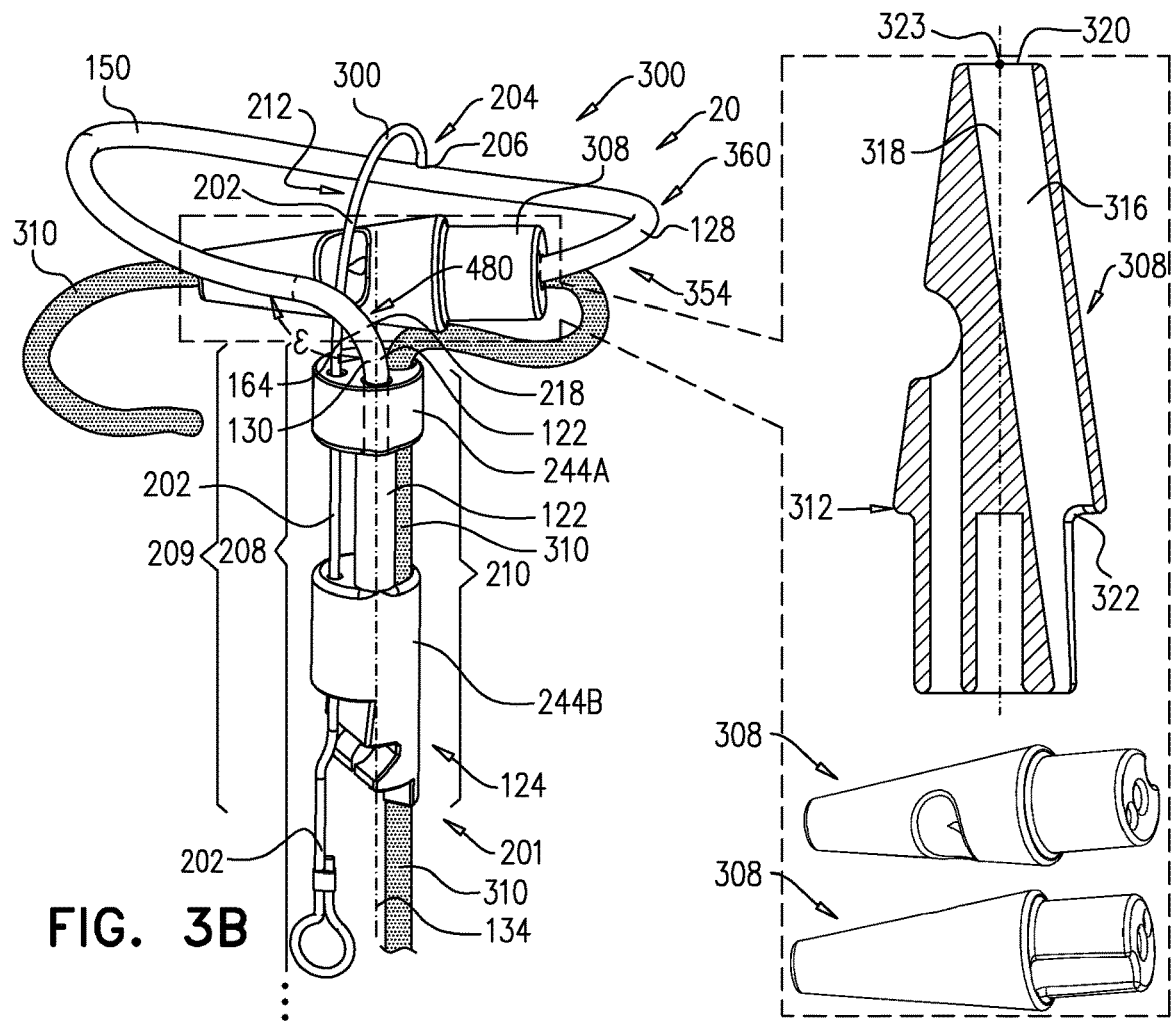

As described hereinabove, proximal portion 208 of flexible elongate tension member 202 has longitudinal segment 209 that runs alongside at least portion 210 of anchor shaft 122 when tissue anchor 20 is unconstrained by deployment tool 30 (these elements are labeled in FIGS. 1C and 3B, described hereinabove). As described hereinabove, tissue anchor 20 is configured to allow relative axial motion between the at least a portion 210 of anchor shaft 122 and longitudinal segment 209 of proximal portion 208 of flexible elongate tension member 202 when tissue anchor 20 is unconstrained by deployment tool 30.

For some applications, application to flexible elongate tension member 202 of a distally-directed force of at least 1 N while tissue anchor 20 is unconstrained draws the distal end of open shape 291 toward distal end 130 of anchor shaft 122.

FIG. 10A is a schematic illustration of a tissue anchor 290, in accordance with an application of the present invention. Tissue anchor 290 is one implementation of tissue anchor 20, described above. Except as described below, tissue anchor 290 is generally similar to tissue anchor 340, described hereinabove with reference to FIG. 8, and tissue anchor 400, described hereinbelow with reference to FIGS. 13A-E. Wire 150 of tissue anchor 290 is not shaped as open loop 154 when tissue anchor 290 is unconstrained by deployment tool 30. Instead, wire 150 is shaped as open shape 291, such as a portion of a circle or a portion of an ellipse. Typically, if, when tissue anchor 290 is unconstrained by deployment tool 30, tissue-coupling element 128 were to be projected onto plane 136 that is perpendicular to central longitudinal axis 134 of anchor shaft 122, open shape 291 would surround at least 170 degrees, no more than 355 degrees, and/or between 170 and 355 degrees of a point 292 in plane 136, such as at least 180 degrees (e.g., at least 190 degrees), no more than 345 degrees, and/or between 180 degrees (e.g., 190 degrees) and 345 degrees. For some applications, such as in which open shape 291 surrounds between 170 and 190 degrees of point 292, site 206 is at distal end 294 of wire 150. For some of these applications, wire 150 is shaped so as to define a channel (i.e., wire 150 is tubular). A portion of flexible elongate tension member 202 passes through the channel and exits the channel of wire 150 at distal end 294 of wire 150. For any of the applications described above, point 292 optionally may fall on a projection onto plane 136 of a line segment that terminates at (a) site 206 on wire 150 and (b) a proximal end 382 of tissue-coupling element 128 when tissue anchor 290 is unconstrained by deployment tool 30. For any of the applications described above, when tissue anchor 290 is unconstrained by deployment tool 30, (a) a line segment that terminates at (i) site 206 (i.e., distal site 380) on open shape 291 and (ii) proximal end 382 of tissue-coupling element 128 may have a total length that equals a percentage of (h) a total length of tissue-coupling element 128, measured along tissue-coupling element 128, the percentage at least 25%, (e.g., at least 40%, such as at least 50%), no more than 75% (e.g., no more than 70%, such as no more than 60%), and/or between 25% and 75% (e.g., between 40% and 70%, such as between 50% and 60%). Typically, at least a portion of tissue-coupling element 128 is curved, such as the entire tissue-coupling element 128.

For some applications, such as shown in FIGS. 10A-F, and 10H, wire 150 is shaped on as to define a channel (i.e., wire 150 is tubular). In these applications, flexible elongate tension member 202 typically passes through at least a portion of the channel. For some applications, such as shown in FIGS. 10A-D and 10H, flexible elongate tension member 202 passes through the entire channel, and distal site 380 on open shape 291 is a distal-end opening of open shape 291. For some applications, a distal end portion of flexible elongate tension member 202 is fixed at or beyond proximal end 382 of open shape 291 (e.g., fixed to anchor head 124 beyond proximal end 382 of open shape 291).

Figure 10B:
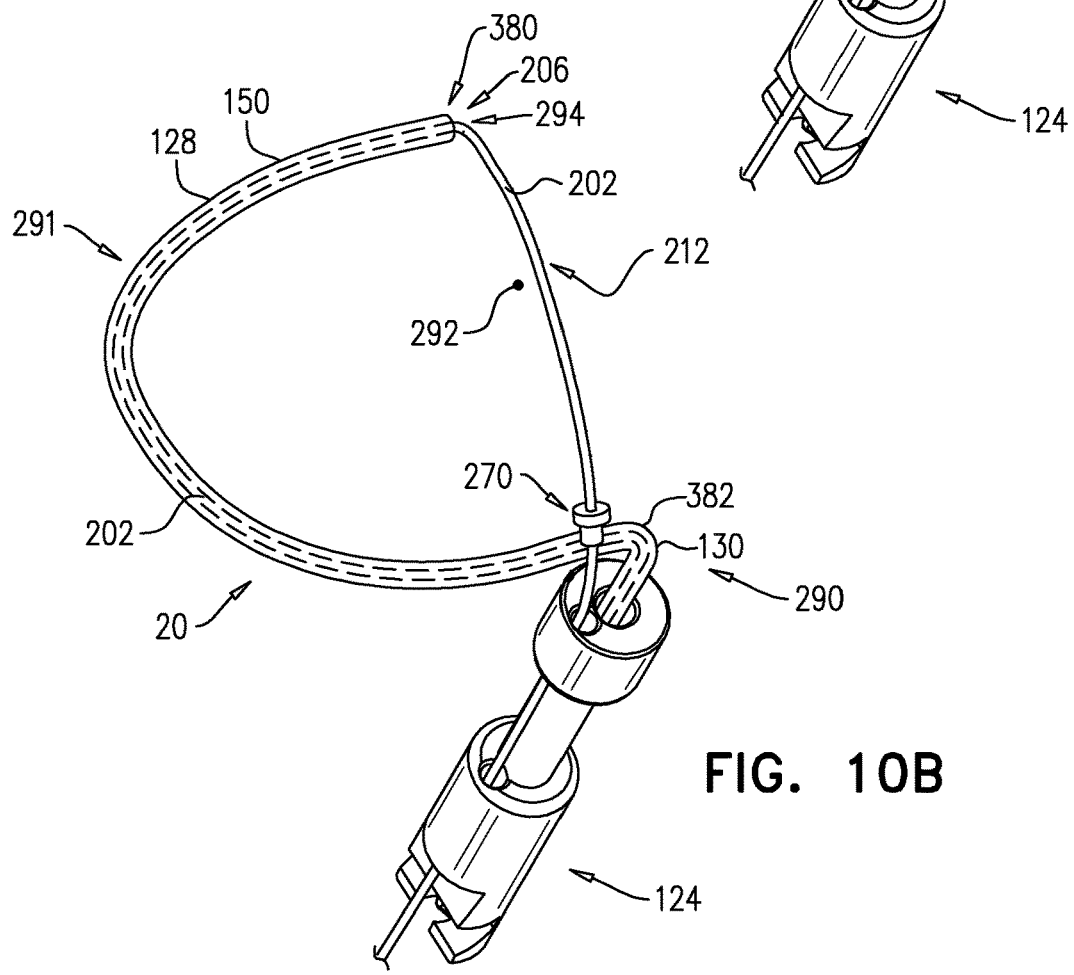

For some applications, such as shown in FIG. 10B, when tissue anchor 20 is unconstrained by deployment tool 30, (a) a line segment that terminates at (i) site 206 on wire 150 and (ii) a proximal end 382 of tissue-coupling element 128 may have a total length that equals a percentage of (b) a total length of tissue-coupling element 128, measured along tissue-coupling element 128, the percentage at least 25%, (e.g., at least 40%, such as at least 50%), no more than 75% (e.g., no more than 70%, such as no more than 60%), and/or between 25% and 75% (e.g., between 40% and 70%, such as between 50% and 60%). Typically, at least a portion of tissue-coupling element 128 is curved, such as the entire tissue-coupling element 128.

Figure 10C:
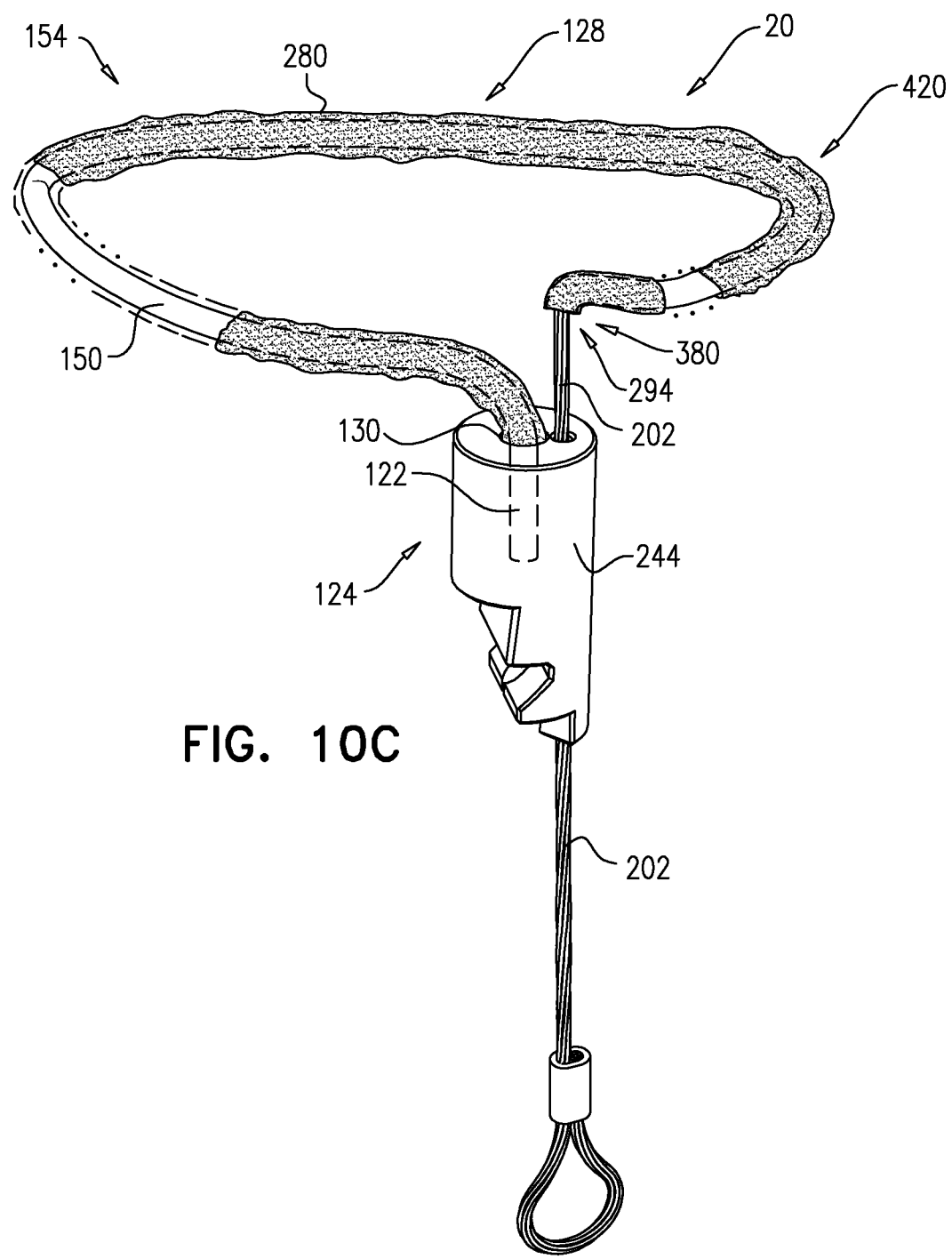
Figure 10D:
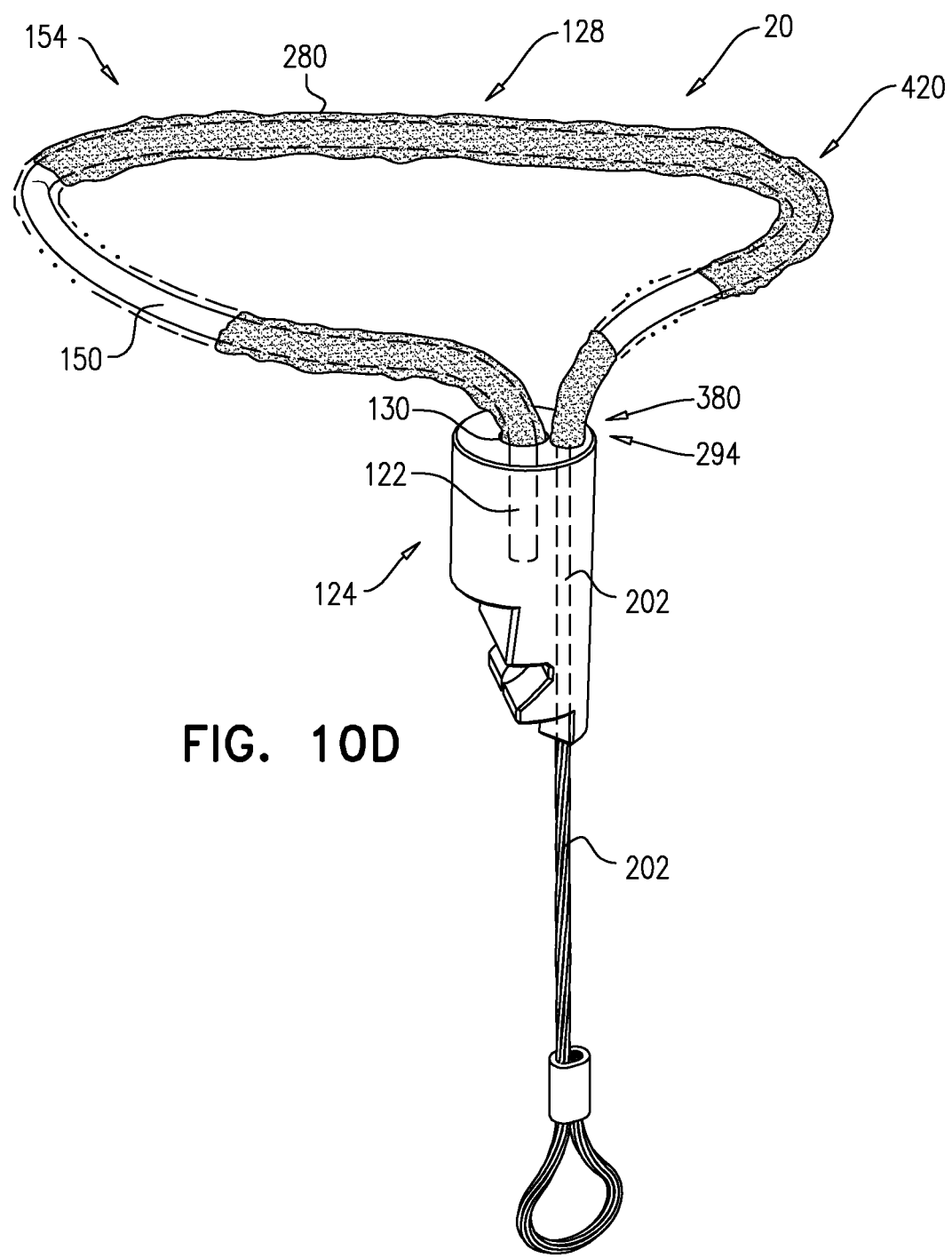

For some of these applications, as shown in FIGS. 10C-D, a tissue anchor 420 is provided, which is one implementation of tissue anchor 20. Upon application of distally-directed tension to flexible elongate tension member 202, distal end 294 of wire 150 is drawn into contact with anchor head 124, such as with collar 244 of the anchor head, which prevents excessive, unnecessary strain on open loop 154. This arrangement is similar to, and may serve as an alternative to, locking stopper 270, described hereinbelow with reference to FIGS. 13D-E.

Figure 10E:
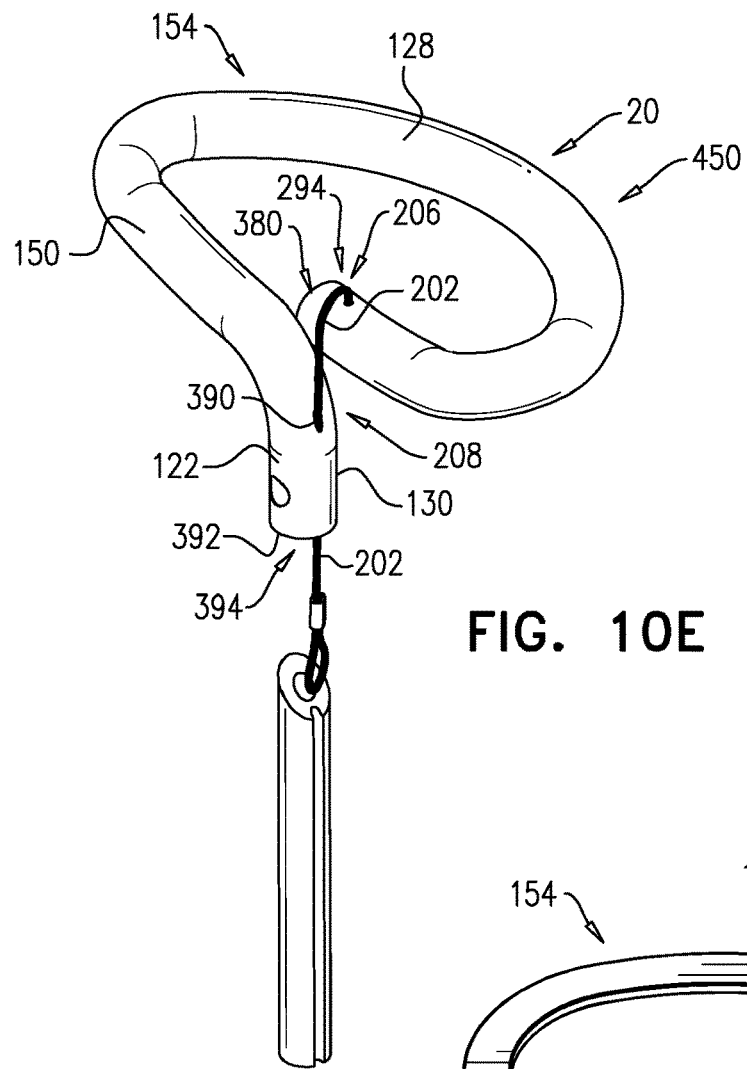

For some of these applications, such as shown in FIG. 10E, the channel has a proximal lateral opening 390 within 7 mm of a proximal end 392 of wire 150, and proximal portion 208 of flexible elongate tension member 202 passes through proximal lateral opening 390. For some applications, proximal portion 208 of flexible elongate tension member 202 passes through proximal lateral opening 390 and through a proximal-end opening 394 of the channel.

For some applications, such as shown in FIG. 10E, the channel has lateral opening 396 at site 206, and distal portion 204 of flexible elongate tension member 202 passes through lateral opening 396.

Figure 10F:
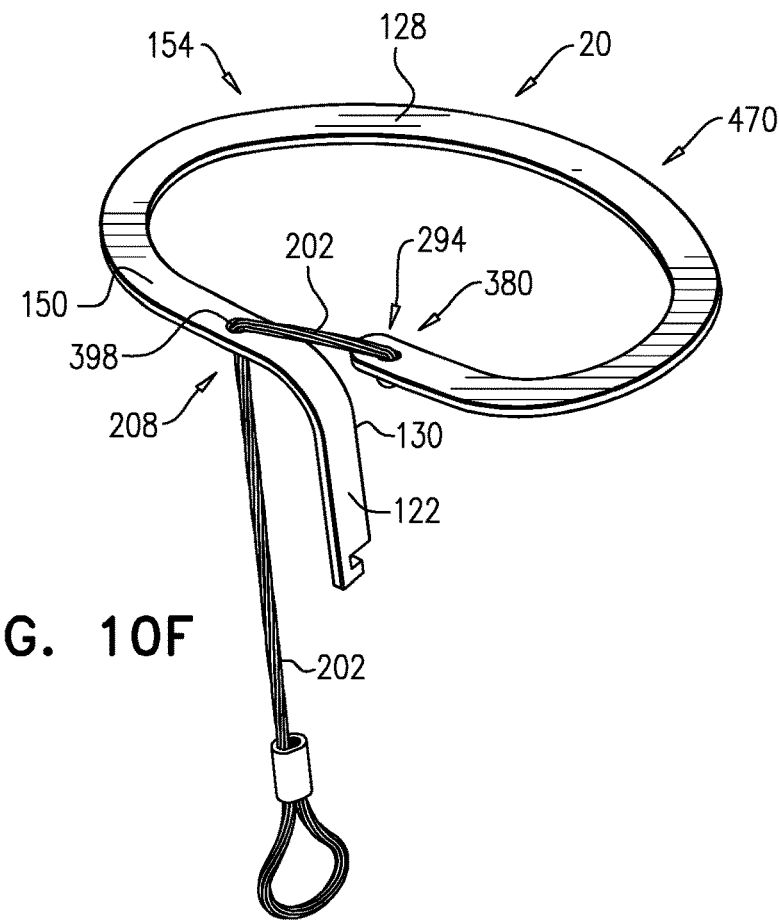

For some applications, such as shown in FIG. 10F, a tissue anchor 470 is provided, which is one implementation of tissue anchor 20. Wire 150 typically has one or more of the shapes and/or dimensions described hereinabove with reference to FIG. 9F.

For some applications, such as shown in FIG. 10F, wire 150 is shaped so as to define a proximal opening 398 within 7 mm (e.g., within 3 mm) of proximal end 392 of wire 150, and proximal portion 208 of flexible elongate tension member 202 passes through proximal opening 398.

For some applications, as shown in FIG. 10G, a tissue anchor 490 is provided, which is one implementation of tissue anchor 20. Open loop 154 generally extends distally from anchor shaft 122. For some applications, wire 150 has one or more of the shapes and/or dimensions described hereinabove with reference to FIG. 9F, except that, unlike the dimensions given for FIG. 9F, typically, when tissue anchor 490 is unconstrained by deployment tool 30: (a) a greatest longitudinal dimension of open shape 291 (e.g., open loop 154), measured in parallel to central longitudinal axis 134 of anchor shaft 122, is between 5 and 15 mm, and (b) a greatest lateral dimension of open shape 291 (e.g., open loop 154), measured perpendicular to central longitudinal axis 134, is between 4 and 20 mm.

Reference is made to FIG. 10H (for clarity of illustration only tip 308 is shown in cross-section). For some applications, the tissue anchors illustrated in FIGS. 10A-D and 10F comprise tip 308. For example, FIG. 10H shows a configuration of tissue anchor 290 of FIG. 10B in which the tissue anchor comprises tip 308. For some applications, distal site 380 is on tip 308. For some applications, in this configuration tip 308 is shaped so as define an extension of the channel (the channel is defined by wire 150). Flexible elongate tension member 202 passes through a portion of tip 308 in this extension of the wire channel, and exits tip 308 (and tissue-coupling element 128) at distal site 380.

Reference is now made to FIG. 11A, which is a schematic illustration of tissue anchor 450, described hereinabove with reference to FIG. 10E, before deployment from deployment tool 30, in accordance with an application of the present invention. In this configuration, deployment tool 30 does not comprise a lumen in which the tissue anchor is constrained during deployment, but instead comprises a rod 494 that is inserted into the channel of tissue anchor 450 and holds the tissue anchor generally straight for delivery. For some applications, rod 494 is shaped no as to define a guidewire lumen 496, or delivery of deployment tool 30 over a guidewire.

Reference is now made to FIG. 11B, which is a schematic illustration of tissue anchor 470, described hereinabove with reference to FIG. 10F, before deployment from deployment tool 30, in accordance with an application of the present invention. The flatness of tissue anchor 470 may leave space in deployment shaft 34 for passage of a guidewire alongside tissue anchor 470.

Reference is now made to FIG. 1, which is a schematic illustration of another configuration of open loop 154, in accordance with an application of the present invention. This configuration may be used in combination tissue anchors 20, 200, 300, 340, 350, 430, 370, 400, 420, 470, and 490. In this configuration, when the tissue anchor is unconstrained by deployment tool 30, open loop 154 is shaped so as to define one or more curved portions 296 (e.g., two or more curved portions 296) and one or more straight portions 298 (e.g., two or more straight portions 298). Straight portions 298 generally maximize the surface contact with the external surface of the heart and thus provide good anchoring. For some applications, open loop 154 is shaped as a common, conventional paper clip (an oblong shape with straight sides, with approximately 1.5 turns).

Reference is now made to FIGS. 13A-D, which are schematic illustrations of a tissue anchor 400, in accordance with an application of the present invention. Tissue anchor 400 is one implementation of tissue anchor 20, described above. Other than as described below, tissue anchor 400 is generally similar to tissue anchor 200, described hereinabove with reference to FIGS. 1A-D, and may implement any of the features thereof, mutatis mutandis. Alternatively or additionally, tissue anchor 400 may implement any of the features of tissue anchor 300, described hereinabove with reference to FIGS. 2A-3D and/or any of the other configurations of tissue anchor 20 described herein, including tissue anchors 200, 340, 350, 430, 370, 420, 470, and 490.

Figure 3C:
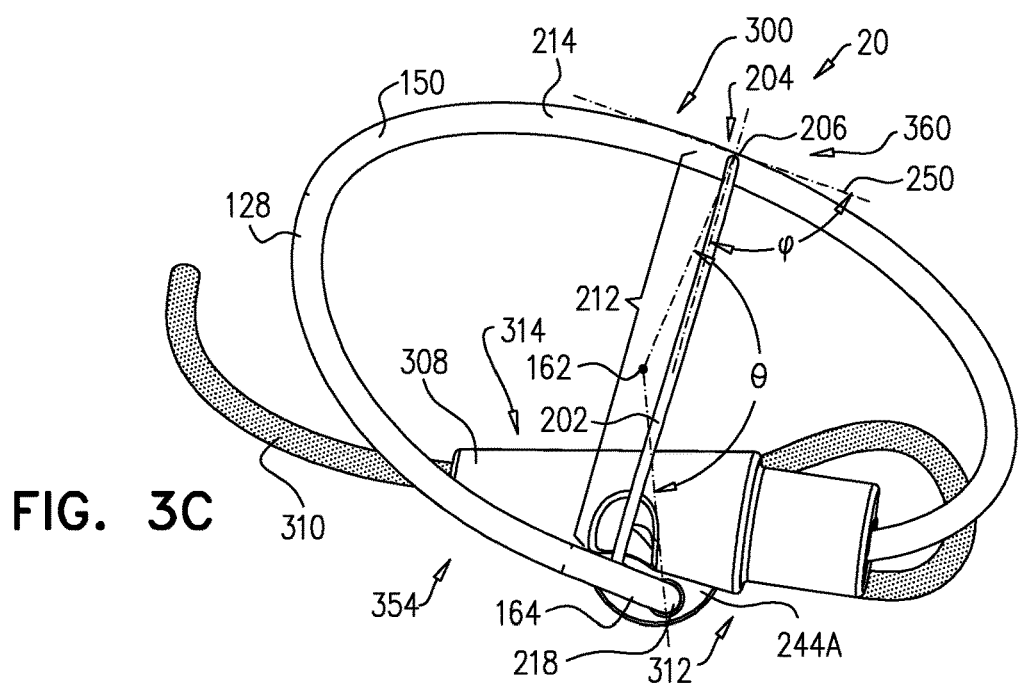

When tissue anchor 400 is unconstrained by deployment tool 30, such as shown in FIGS. 13A-D, wire 150 is shaped as open loop 154 (e.g., a three-dimensional open loop) around center point 162 (labeled in FIGS. 1D and 3C), and, optionally, as spiral 160 (e.g., a three-dimensional spiral) around center point 162 (labeled in FIGS. 1D and 3C). For some applications, such as shown in FIGS. 13A-D, wire 150 extends from distal end 130 of anchor shaft 122 at radially-outer end 164 of open loop 154 (and, optionally, spiral 160) (labeled in FIG. 13A), when tissue anchor 400 is unconstrained by deployment tool 30. For some applications, open loop 154 (and, optionally, spiral 160) has the dimensions described hereinabove with reference to FIGS. 5A-B and/or 5C-D. For some applications, tissue-coupling element 128 has one or more of the characteristics described hereinabove with reference to FIGS. 5C-D. For some applications, the proximally-facing surface defined by tissue-coupling element 128 is generally flat, when tissue anchor 400 is unconstrained by deployment tool 30 (configuration not shown). Optionally, upon coming into full contact with the external surface of the heart, the proximally-facing surface defined by the tissue-coupling element may assume a concave shape conforming to the convex shape of the external surface of the heart.

In the configuration shown in FIGS. 13A-D, tissue anchor 400 further comprises flexible elongate tension member 202, which includes:
distal portion 204 that is fixed to site 206 on open loop 154 (such as by welding, soldering, crimping, and/or knotting, and/or as described hereinabove with reference to FIGS. 9A-F),
proximal portion 208, which has longitudinal segment 209 that runs alongside at least portion 210 of anchor shaft 122 (labeled in FIG. 13B, in which the at least a portion 210 of anchor shaft 122 is the entire length of anchor shaft 122), and crossing portion 212, which (a) is disposed between distal and proximal portions 204 and 208 along flexible elongate tension member 202, and (ii) crosses at least a portion of open loop 154 when tissue anchor 400 is unconstrained by deployment tool 30.

Although flexible elongate tension member 202 is fixed to wire 150 of tissue-coupling element 128, flexible elongate tension member 202 is typically distinct from wire 150. In other words, flexible elongate tension member 202 and wire 150 are not two longitudinal portions of a single continuous wire, i.e., are not longitudinally contiguous with each other.

Tension is applied to tissue-coupling element 128 of tissue anchor 400 via flexible elongate tension member 202. The applied tension is resisted by the outward force of open loop 154. The applied tension at least partially compresses and stiffens open loop 154. This arrangement of tension distribution may overcome any natural tendency of open loop 154 to straighten (i.e., unwind) if tension were to be applied along central longitudinal axis 134 via anchor shaft 122, and thus may allow the application of a greater load to open loop 154.

Typically, before tension is applied to flexible elongate tension member 202, when tissue anchor 400 is unconstrained by deployment tool 30, flexible elongate tension member 202 is not taut across the at least a portion of open loop 154. For example, flexible elongate tension member 202 may arc distally, such as can best be seen in FIG. 13A.

Figure 13A:
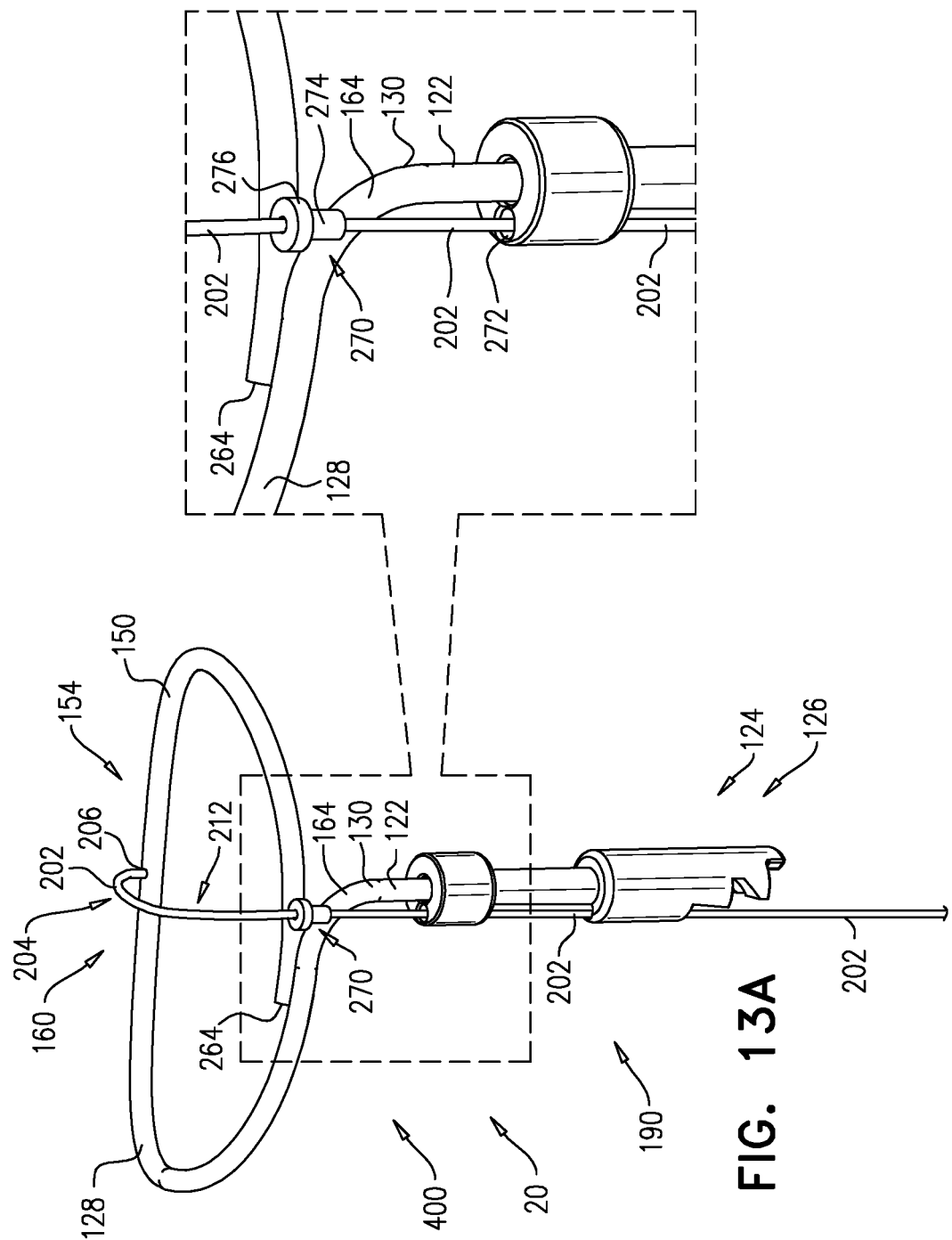
FIGS. 13A-D are schematic illustrations of another tissue anchor having a locking stopper, in accordance with an application of the present invention.

Typically, tissue anchor 400 is configured to allow relative axial motion between the at least a portion 210 of anchor shaft 122 and longitudinal segment 209 of proximal portion 208 of flexible elongate tension member 202 when tissue anchor 400 is unconstrained by deployment tool 30. Such axial motion allows tension to be applied to flexible elongate tension member 202 without also being applied to anchor shaft 122, and allows open loop 154 to be unwound and flexible elongate tension member 202 to be disposed alongside a portion of flexible elongate tension member 202, as shown in FIG. 13A. Typically, longitudinal segment 209 of proximal portion 208 of flexible elongate tension member 202 is coupled in sliding communication with the at least a portion 210 of anchor shaft 122, when tissue anchor 400 is unconstrained by deployment tool 30. For some applications, tissue anchor 400 comprises one or more annular elements, which are disposed around the at least a portion of anchor shaft 122, and couple flexible elongate tension member 202 in the sliding communication with the at least a portion 210 of anchor shaft 122, when tissue anchor 400 is unconstrained by deployment tool 30. For example, the annular elements may comprise one or more collars, loops, or rings. Anchor shaft 122 (e.g., the collars) is shaped such that flexible elongate tension member 202 nuns generally parallel to central longitudinal axis 134 of anchor shaft 122.

For some applications, as shown, site 206 is on an outer lost turn of open loop 154, when tissue anchor 400 is unconstrained by deployment tool 30. For some other applications, site 206 is on a second-to-outermost turn of open loop 154, when tissue anchor 400 is unconstrained by deployment tool 30 (configuration not shown).

Typically, a radius of flexible elongate tension member 202 is less than a radius of wire 150, such as less than 50% of the radius of wire 150. Flexible elongate tension member 202 and/or wire 150 may have any of the characteristics described hereinabove with reference to FIGS. 3C, 5A-D and/or 5C-D, including dimensions and relative arrangement with respect to each other.

For some applications, one or more tethers 132 are provided, which are configured to be coupled to tissue anchor 400. Typically, the one or more tethers 132 are fixed to flexible elongate tension member 202, typically to proximal portion 208 of the tension member, such as at or near (e.g., within 1 cm of) a proximal end of proximal portion 208. When tension is applied to the one or more tethers, the tension is transmitted to flexible elongate tension member 202, rather than to anchor shaft 122 via anchor head 124.

For some applications, anchor head 124 is shaped so as to define a passage 272 in which proximal portion 208 of flexible elongate tension member 202 is slidably disposed. Flexible elongate tension member 202 comprises a locking stopper 270, which is axially fixed to proximal portion 208 or crossing portion 212 of flexible elongate tension member 202. Locking stopper 270 and passage 272 are sized and shaped such that the size and shape of passage 272 prevent proximal movement of locking stopper 270 past passage 272. Optionally, locking stopper 270 engages passage 272 (as shown). For some applications, passage 272 is a channel through a portion of anchor head 124 (such as through one or more collars of anchor head 124) (as shown), while for other applications, passage 272 is a groove (e.g., a U-shaped groove) (configuration not shown). For some applications, locking stopper 270 is shaped so as to define abase 274 and a flange 276. The flange is too large to pass through passage 272, while base 274 may or may not be too large to enter the passage. For some applications, locking stopper 270 is manufactured as a separate element that is fixed to flexible elongate tension member 202, such as by crimping, welding, or soldering. For other applications, locking stopper 270 is integral to flexible elongate tension member 202.

Figure 13B:
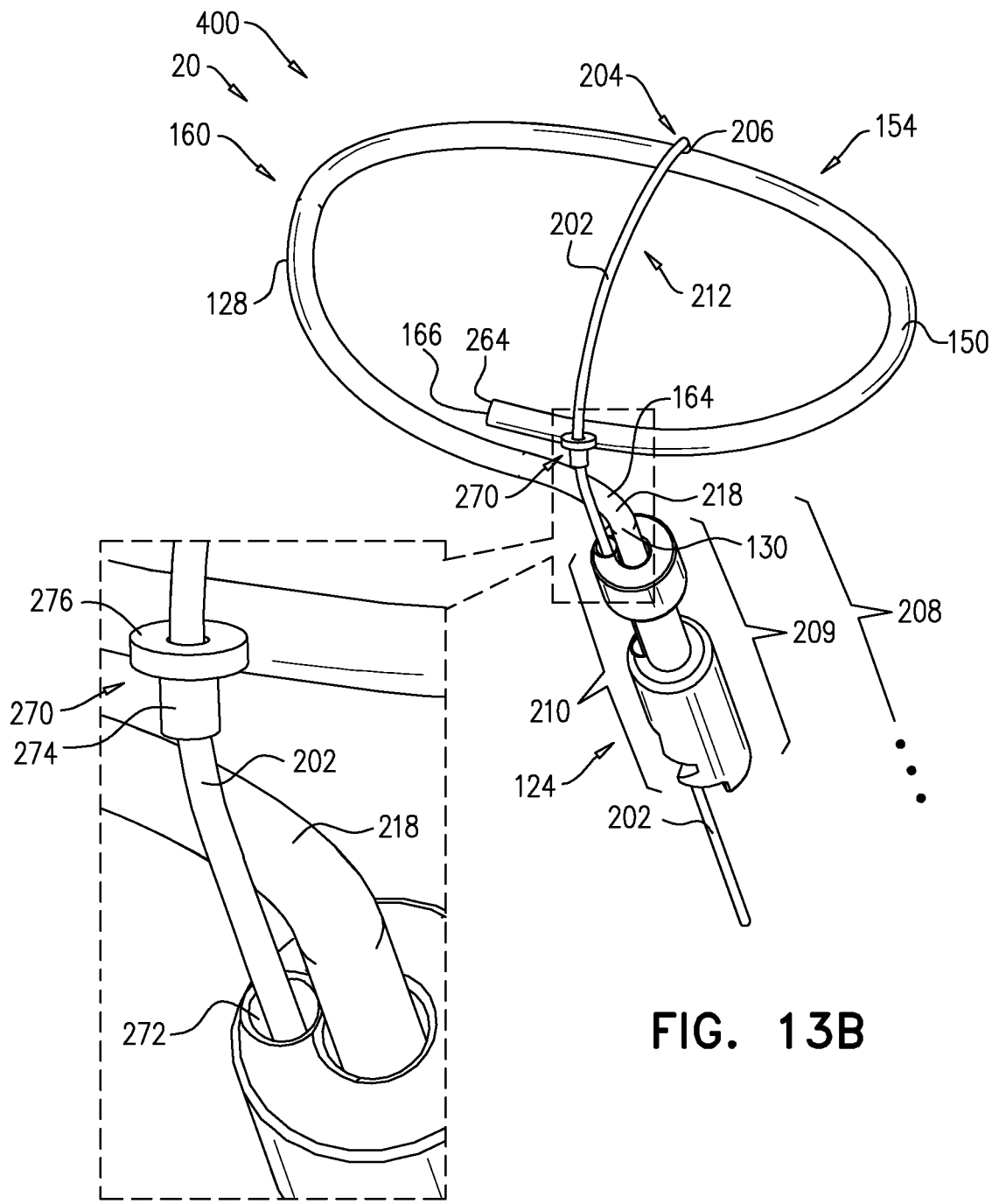

For some applications, passage 272 extends to a distal end of anchor head 124 (as shown), while for other applications, passage 272 is disposed more proximally in anchor head 124, such as near a proximal end of anchor head 124 (configuration not shown). Typically, locking stopper 270 is axially fixed to proximal portion 208 or crossing portion 212 of flexible elongate tension member 202 at a distance of at least 7 mm, no more than 22 mm, and/or between 7 and 22 mm from site 206 on the open loop, measured along flexible elongate tension member 202 (i.e., measured along the curvature of flexible elongate tension member 202 if it is curved, such as shown in FIGS. 13A-B). Alternatively or additionally, for some applications, if tissue-coupling element 128 were straightened in an elongated configuration, for example by being disposed in deployment tool 30 such as shown in FIG. 1A mutatis mutandis, locking stopper 270 would be a distance of at least 7 mm, no more than 12 mm, and/or between 7 and 12 mm (e.g., 10 mm) from passage 272. Alternatively, or additionally, for some applications, when tissue anchor 400 is unconstrained by deployment tool 30 (and flexible elongate tension member 202 is curved, such as shown in FIGS. 13A-B), locking stopper 270 is disposed at a distance of at least 7 mm, no more than 12 mm, and/or between 7 and 12 mm (e.g., 10 mm) from passage 272. For some applications, when sufficient tension is applied to flexible elongate tension member 202 straighten flexible elongate tension member 202 but not compress open loop 154, locking stopper 270 moves between 5 and 8 mm toward passage 272, such that locking stopper 270 is disposed at a distance of at least 2 mm, no more than 5 mm, and/or between 2 and 5 mm (e.g., 10 mm) from passage 272.

Figure 13C:
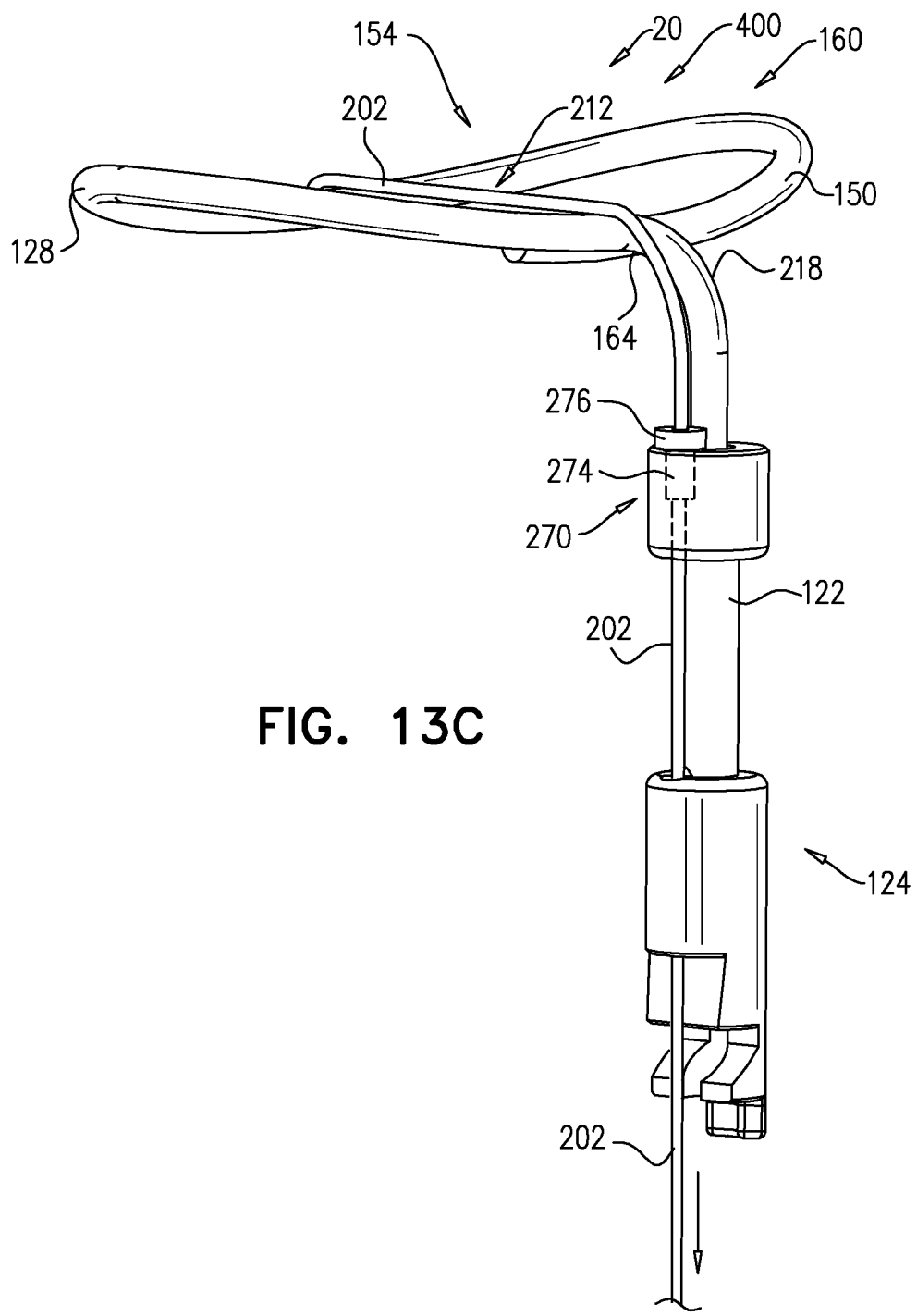
Figure 13D:
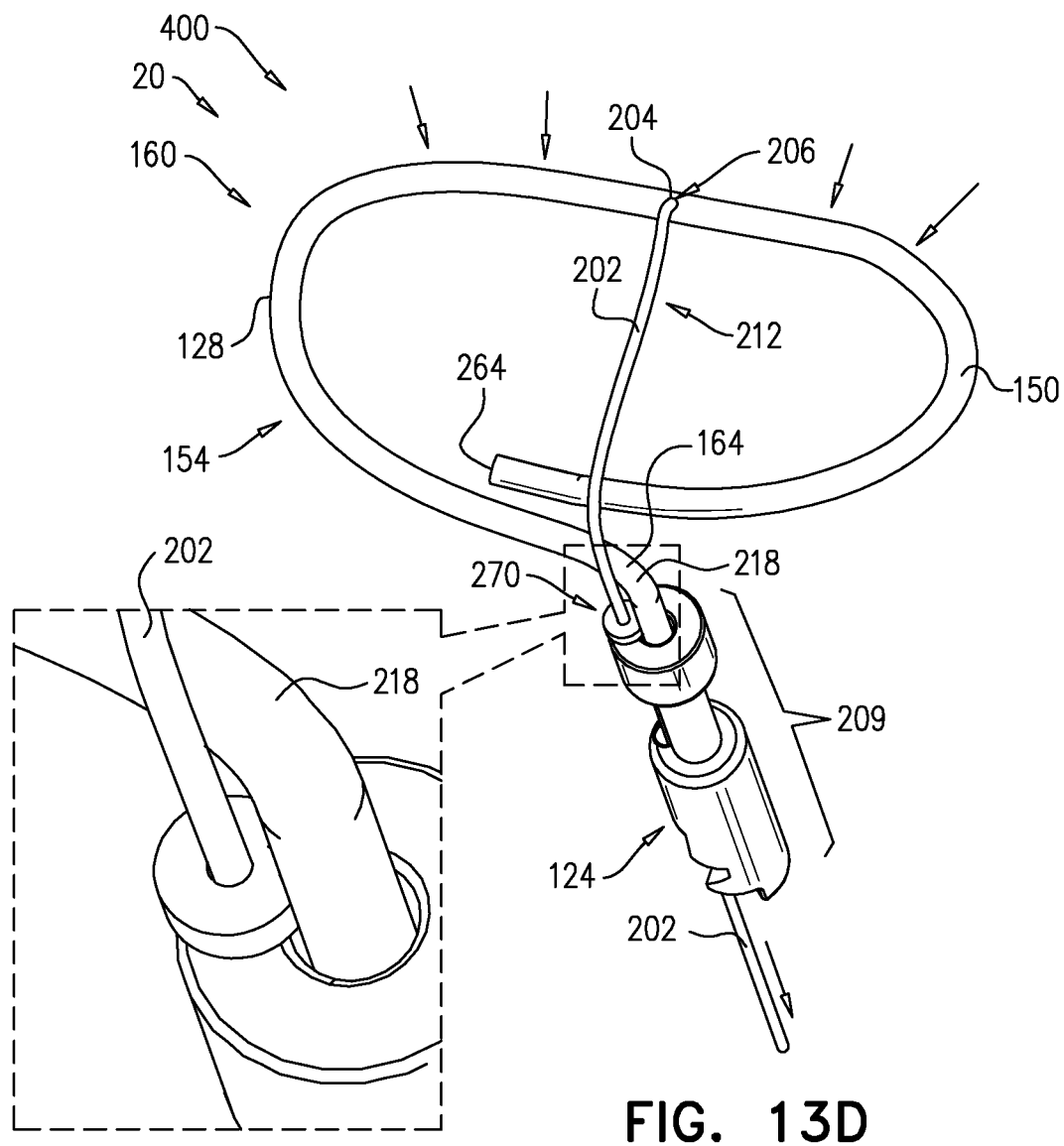

As shown in FIG. 13C-D, tension is applied to tissue-coupling element 128 of tissue anchor 200 via flexible elongate tension member 202. The applied tension is resisted by the outward force of open loop 154. The applied tension at least partially compresses and stiffens open loop 154. This arrangement of tension distribution may overcome any natural tendency of open loop 154 to straighten (i.e., unwind) if tension were to be applied along central longitudinal axis 134 via anchor shaft 122, and thus may allow the application of a greater load to open loop 154. The tension applied to tissue-coupling element 128 thus locks open loop 154 into a desired shape.

Locking stopper 270 limits the total load that can be applied to open loop 154 by flexible elongate tension member 202, thereby reducing excessive, unnecessary strain on open loop 154. For example, the first 1.5 to 5 N of force applied to flexible elongate tension member 202 may sufficiently deform open loop 154 and engage locking stopper 270. Additional load (tension) that is applied by flexible elongate tension member 202 pulls on the entire tissue anchor 400, and does not further increase the load applied across open loop 154 to site 206, and thus does not further compress the open loop. As described hereinbelow with reference to FIGS. 14D and 15A-C, such tension may be applied to pull tissue anchor 400 closer to another tissue anchor, in order to facilitate repair of an atrioventricular valve of the subject, such as tricuspid valve 504.

These techniques thus allow the use of relatively flexible tissue-coupling element, in order to not generate too much outward force inside a delivery tube, which might make axial movement of the tissue-coupling element in the delivery tube difficult or impossible. The tissue-coupling element is tensioned upon delivery, thereby changing its shape and providing a strong tissue-coupling element that cannot unwind easily, and thus remains coupled to the tissue. In addition, minimizing the load on attachment site 206 provides a mechanical advantage that increases the durability of the device under higher loads.

As mentioned above, open loop 154 may have more than one turn and less than 1.5 turns, such as more than one turn, e.g., more than 1.01 turns (363.6 degrees), such as more than 1.02 turns (367.2 degrees), and/or less than 1.25 turns (450 degrees) (one turn equals 360 degrees). Providing open loop 154 with more than one turn, rather than exactly one turn or less than one turn, prevents crossing portion 212 from sliding down off of open loop 154 and onto anchor shaft 122 when tension is applied to crossing portion 212. Such sliding might result in crossing portion 212 cutting into tissue of the heart.

Figure 13E:
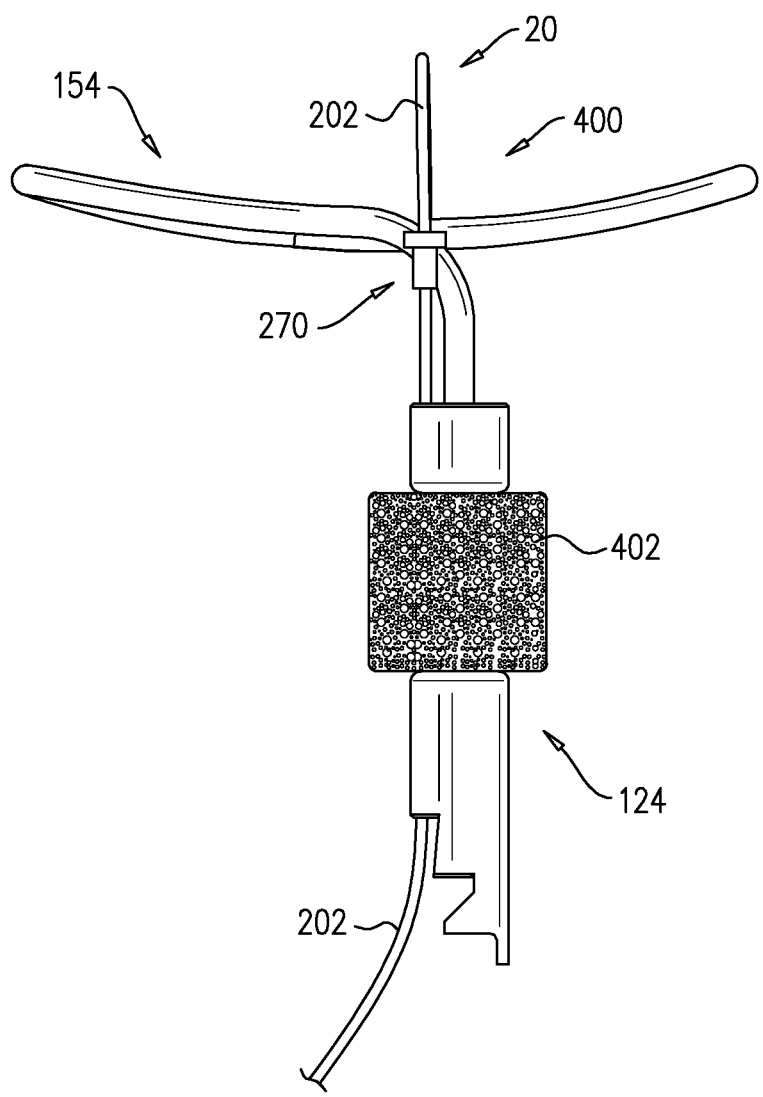
FIG. 13E is a schematic illustration of the tissue anchor of FIGS. 13A-D comprising a sealing element, in accordance with an application of the present invention.

Reference is made to FIG. 13E, which is a schematic illustration of tissue anchor 400 comprising a sealing element 402, in accordance with an application of the present invention. Sealing element 402 is similar in some respects to sealing element 190, described hereinabove with reference to FIGS. 1A-D and 4A-B. Sealing element 402 is configured to form a blood-tight seal between a portion of anchor head 124 inside the heart chamber and wall 194 of the heart. For some applications, sealing element 402 comprises a compressible sponge. For some applications, an outer diameter of sealing element 402, when expanded, equals at least 1.5 times, e.g., at least 2 times, an inner diameter of deployment shaft 34 of deployment tool 30, described hereinabove with reference to FIG. 1A. For some applications, sealing element 402 is disposed on the narrower portion of anchor head 124 between two collars.

Reference is made to FIGS. 1B-C, 3A-B, 4A-B, 5A-D, 7, 8, 9A-F, 1.0A-H, and 13A-E. For some applications, tissue anchor 20 is shaped so as to define a bend 480 at an interface between tissue-coupling element 128 and anchor shaft 122. Typically, bend 480 has an angle α (epsilon) of between 45 and 135 degrees, e.g., between 60 and 120 degrees, such as between 85 and 105 degrees, e.g., 90 degrees, as labeled in FIGS. 1C and 3B.

Reference is now made to FIGS. 14A-D, which are schematic illustrations of a method for deploying tissue anchor system 248, described hereinabove with reference to FIGS. 4A-B, for repairing tricuspid valve 504, in accordance with an application of the present invention. In the particular method shown in these figures, first and second tissue anchors 182A and 182B of tissue anchor system 248 comprise first tissue anchor 400, described hereinabove with reference to FIGS. 13A-E, and stent 186, described hereinabove with reference to FIG. 4B. The method may also be used to deploy other tissue anchors described herein, mutatis mutandis, including tissue anchor 300. Tissue anchor system 248 further comprises deployment tool 30, for deploying first tissue anchor 182A, and, typically, a second anchor delivery tool for deploying second tissue anchor 182B.

Figure 14A:
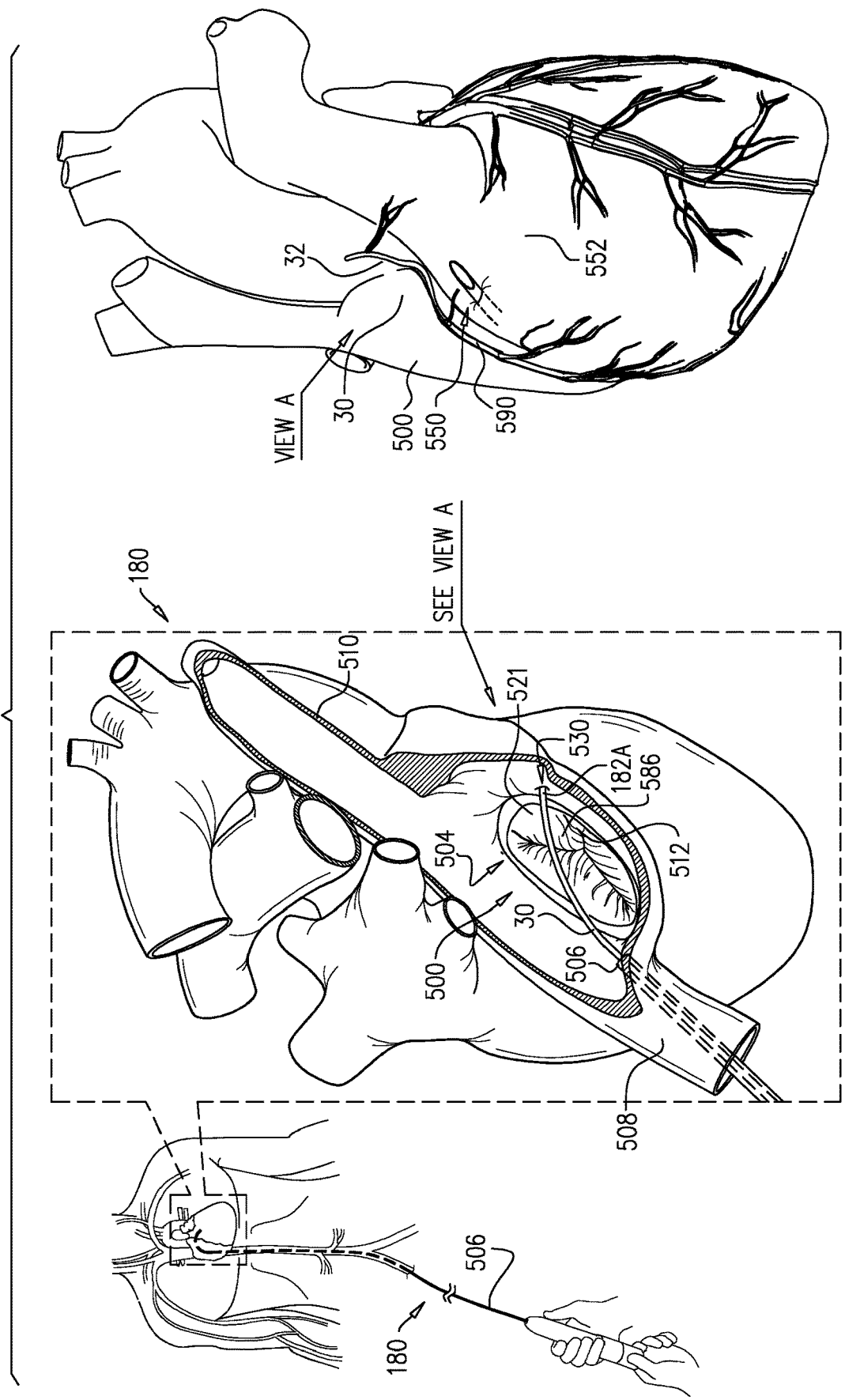

As shown in FIG. 14A, first anchor deployment tool 30 is advanced, during a transcatheter procedure (typically endovascularly, such as percutaneously). Also as shown in FIG. 14A, for applications in which deployment tool 30 is shaped so as to define sharp distal piercing tip 32, such as described hereinabove with reference to FIG. 1A, first anchor deployment tool 30 is advanced through the wall of the heart by advancing sharp distal piercing tip 32 of the tool through first implantation site 530. Successful passage through the wall is typically confirmed using imaging.

For applications in which tissue anchor 20 comprises tip 308, typically one of the configurations of deployment tool 30 described with reference to FIGS. 2A-B or 6A-B is instead used; in these configurations, deployment tool 30 (including deployment shaft 34) is not shaped so as define sharp distal piercing tip 32. Typically, guidewire 310 is first introduced through the wall of the heart using conventional transcatheter guidewire advancement techniques, and deployment tool 30, with tissue anchor 20 disposed therein, is deployed through the wall over the guidewire.

First implantation site 530 is shown as within 1 cm of the site on the annulus that circumferentially corresponds to circumferential middle 521 of anterior leaflet 586; alternative first implantation sites 530 are set forth hereinbelow in Table 1. For some applications, first implantation site 530 is within 10 mm, such as within 5 mm, of RCA 590.

Figure 14B:
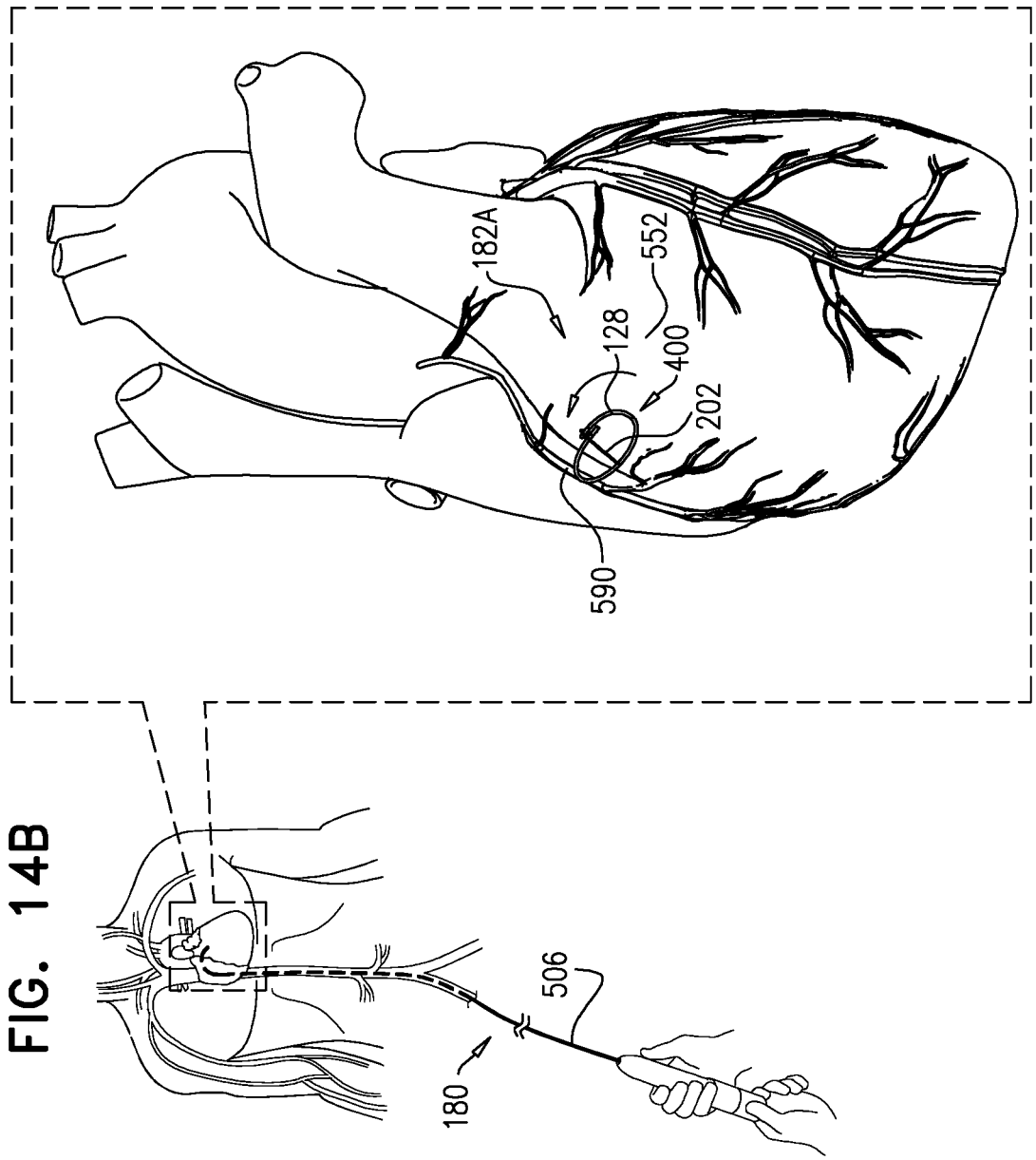

As shown in FIG. 14B, first tissue anchor 182A is partially released from first anchor deployment tool 30 such that tissue-coupling element 128 is unconstrained by first anchor deployment tool 30. The surgeon ascertains, typically using imaging, whether tissue-coupling element 128 overlies a coronary blood vessel, such as RCA 590. In the procedure shown in FIG. 14B, tissue-coupling element 128 does overlie a coronary blood vessel (RCA 590). For applications in which tissue anchor 20 comprises tip 308, once proper deployment of tissue-coupling element 128 is confirmed, guidewire 310 is withdrawn. (Guidewire 310 is shown in FIGS. 3A-C for clarity of illustration; during the implantation procedure, the guidewire is typically withdrawn before the tissue anchor reaches the configuration shown in these figures.)

For some applications, such as shown in FIGS. 14A-D, first anchor deployment tool 30, and first tissue anchor 182A, exit the heart at external exit site 550 on right atrium 500. Typically, in these applications, first tissue anchor 182A passes through an atrial portion of the annulus, or an edge of the annulus and the origin of the trabeculae carneae. For other applications, such as described hereinbelow with reference to FIG. 16, first anchor deployment tool 30, and first tissue anchor 182A, exit the heart at external exit site 550 on right ventricle 552. Typically, in these applications, first tissue anchor 182A passes under RCA 590 in the annulus and exits on the ventricular wall.

If tissue-coupling element 128 overlies a coronary blood vessel (e.g., RCA 590), the surgeon rotates first tissue anchor 182A (clockwise and/or counterclockwise, about central longitudinal axis 134) until tissue-coupling element 128 no longer overlies the coronary blood vessel, as shown in FIG. 14C. The rotation is typically performed by rotating anchor shaft 122. The surgeon brings tissue-coupling element 128 into contact with an external surface 534 of the heart, by proximally retracting first tissue anchor 182A.

Providing the tissue anchor (e.g., tissue anchor 400) with an elliptical shape (or paper clip shape) reduces the risk of contact with a sensitive anatomic structure, such as a blood vessel, e.g., the RCA.

After first tissue anchor 182A has been implanted at first implantation site 530, driver 201 is decoupled from the anchor head and deployment tool 30 is removed from the subject's body, typically leaving catheter 506 in situ.

Figure 14D:
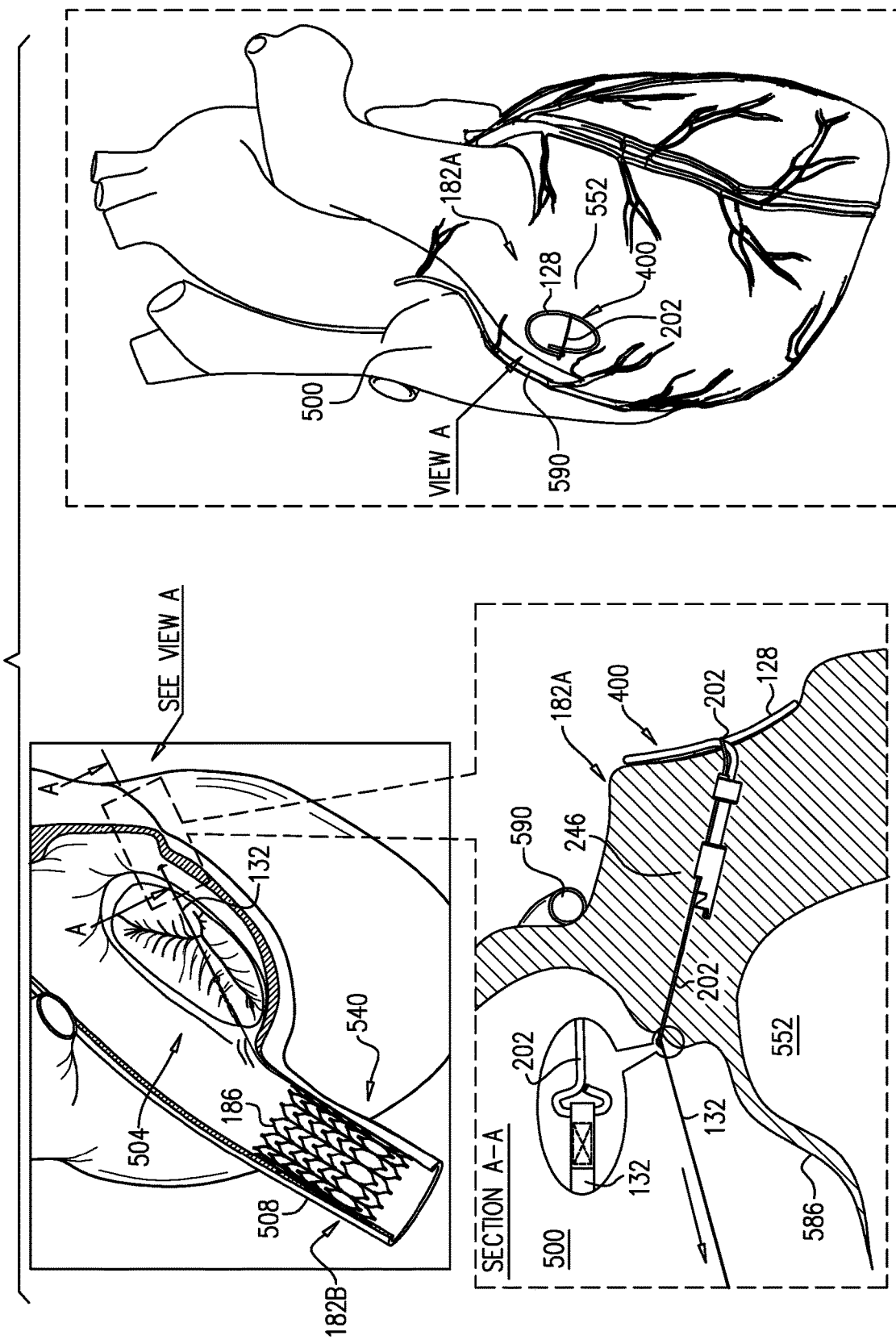

As shown in FIG. 14D, second tissue anchor 182B is implanted in the subject at second implantation site 540. For example, as shown, second tissue anchor 182B may comprise stent 186, and second implantation site 540 may be inferior vena cava 508; an alternative second implantation site 540 is set forth hereinbelow in Table 1. Tension is applied to the one or more tethers 132 that couple the first tissue anchor 182A (e.g., flexible elongate tension member 202 thereof) to second tissue anchor 182B. Typically, the tension is applied without applying tension to anchor shaft 122. Application of such tension facilitates repair of an atrioventricular valve of the subject, such as tricuspid valve 504.

For some applications, second tissue anchor 182B is implanted in the subject, and first tissue anchor 182A is coupled to second tissue anchor 182B by the one or more tethers 132 using the techniques described for connecting first and second tissue-engaging elements 60a and 60b in US Patent Application Publication 2014/0114390 with reference to FIGS. 34A-E thereof; the '390 publication is incorporated herein by reference. For some applications, one of the one or more tethers 132 is fixed to one of (a) first tissue anchor 182A and (b) second tissue anchor 182B. For some applications, first and second tissue anchors 182A and 182B are implanted using techniques described in US Patent Application Publication 2012/0035712 with reference to FIGS. 7A-D and/or FIGS. 11A-B thereof; the '715 publication is incorporated herein by reference.

The following Table 1 sets forth exemplary combinations of (a) anatomical markers for first implantation site 530, (b) second implantation site 540, and (c) external exit sites 550. These sites are listed by way of example and not limitation; the surgeon typically selects the exact sites based on the subject's individual needs and anatomy. Any appropriate location on the heart wall may be used. First implantation site 530 is located within 1 cm of the site on the annulus that circumferentially corresponds to the anatomical marker (i.e., is at the same angular location or "o'clock" as the respective anatomical marker). The direction of the 1 cm from the site on the annulus may be either circumferentially (i.e., clockwise or counterclockwise) around the annulus, up the wall of the right atrium above the annulus, or a combination of circumferentially around the annulus and up the wall of the atrium.

Typically, the surgeon uses the anatomical markers to find the exact location first implantation site 530, which is within 1 cm of the anatomical markers, as described above. For example, the commissures are easily detectable using imaging, and thus represent good anatomical markers. However, the commissures are not appropriate for implantation (because they are too delicate), so, in this example, the tissue anchors are implanted near the annulus, such as up the wall of the atrium, within 1 cm from the commissure.

TABLE 1

| First implantation site 530 anatomical marker | Second implantation site 540 | External exit site 550 |
| --- | --- | --- |
| Circumferential middle 521 of anterior leaflet 586 | Inferior vena cava 508 | Right atrium 500 (site 550A in FIG. 16) |
| An anteroposterior commissure 512 | Inferior vena cava 508 | Right atrium 500 (site 550B in FIG. 16) |
| Circumferential middle 521 of anterior leaflet 586 | Inferior vena cava 508 | Right ventricle 552 (site 550C in FIG. 16) |
| Anteroposterior commissure 512 | Inferior vena cava 508 | Right ventricle 552 (site 550D in FIG. 16) |
| A circumferential middle of a posterior leaflet | Superior vena cava 510 | Right ventricle 552 (site 550C in FIG. 16) |
| Anteroposterior commissure 512 | Superior vena cava 510 | Right ventricle 552 (site 550D in FIG. 16) |
| Circumferential middle 521 of anterior leaflet 586 | A coronary sinus | Right atrium 500 (site 550A in FIG. 16) |

Figure 15A:
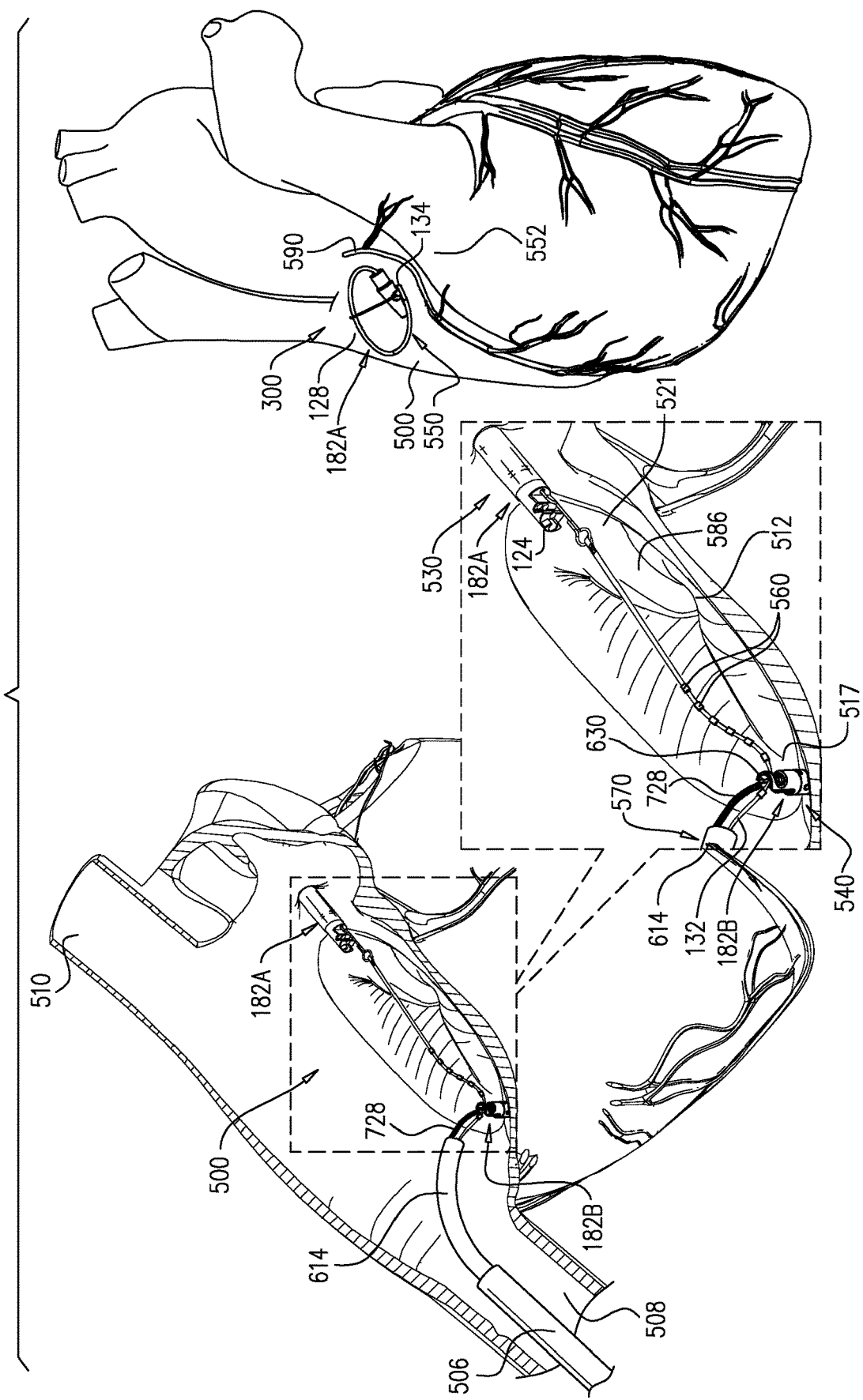
FIGS. 15A-C are schematic illustrations of a method for deploying the tissue anchor system of FIG. 4A for repairing the tricuspid valve, in accordance with an application of the present invention.
Figure 15B:
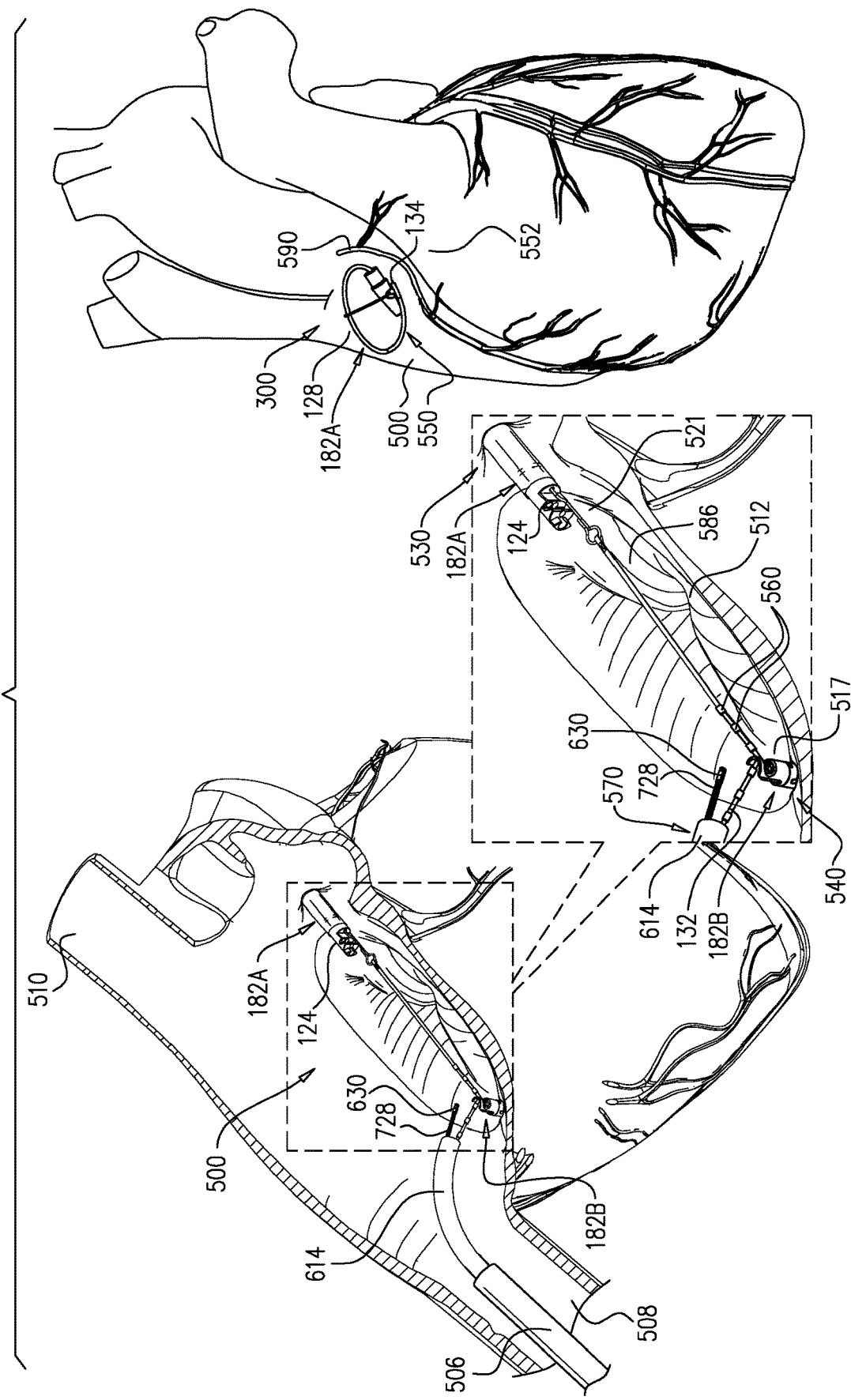
Figure 15C:
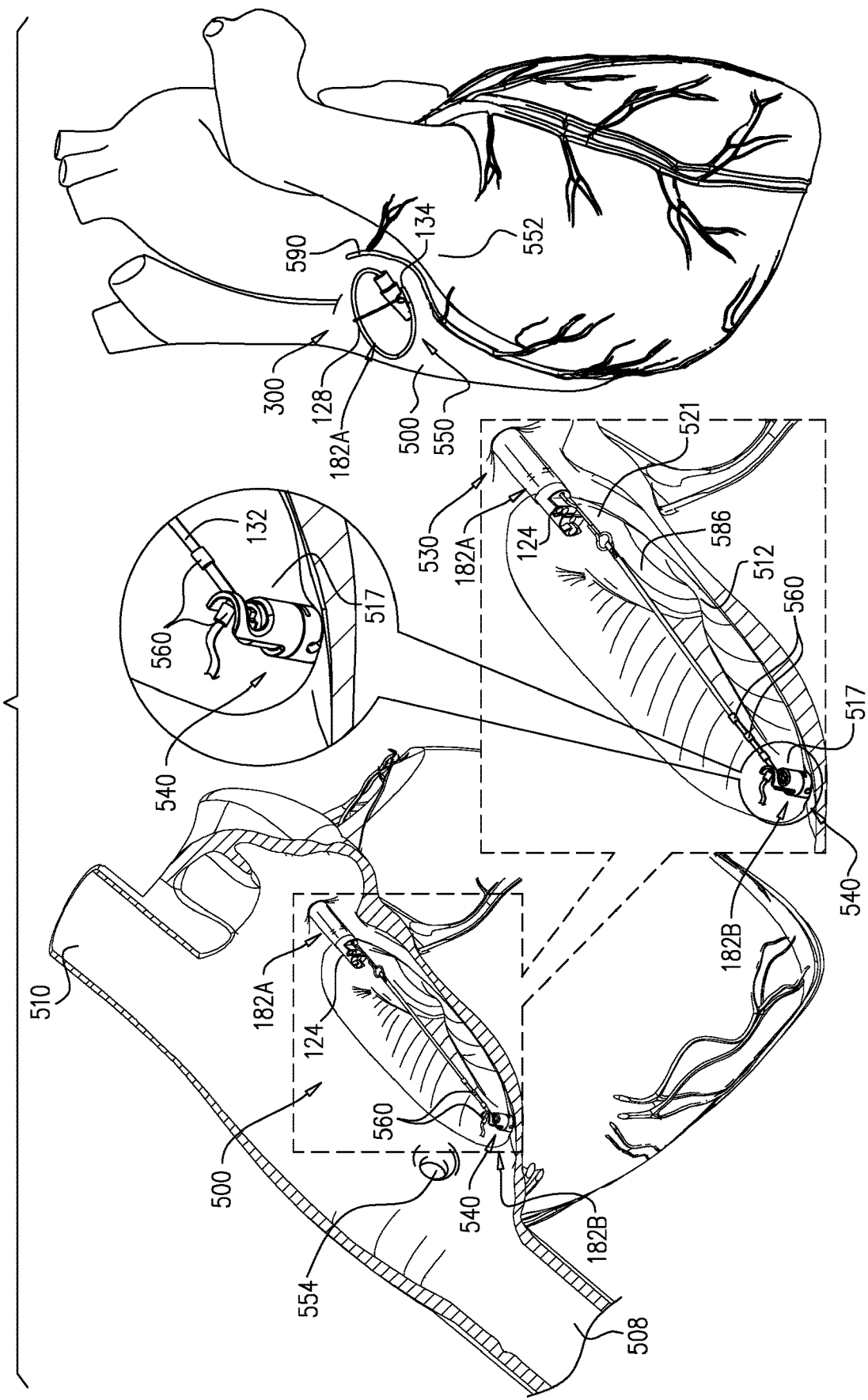

Reference is now made to FIGS. 15A-C, which are schematic illustrations of another method for deploying tissue anchor system 248 for repairing tricuspid valve 504, in accordance with an application of the present invention. In the particular method shown in these figures, first tissue anchor 182A of tissue anchor system 248 comprises first tissue anchor 300, and second tissue anchor 182B of tissue anchor system 180 comprises helical tissue-coupling element 184, described hereinabove with reference to FIG. 4A. The method may also be used to deploy other tissue anchors described herein, including tissue anchor 200 or 400 of tissue anchor system 248 as the first tissue anchor, mutatis mutandis. Tissue anchor system 180 or tissue anchor system 248 further comprises deployment tool 30, for deploying first tissue anchor 182A, and, typically, a second anchor delivery tool 570 for deploying second tissue anchor 182B. For some applications, second anchor delivery tool 570 comprises a torque-delivery tool, such as described in PCT Publication WO 2015/193728, which is incorporated herein by reference. Tissue anchor system 248 allows first and second tissue anchors 182A and 182B to be delivered separately and connected afterwards in situ. This simplifies the procedure for the operator, and allows an approach from two or more different blood vessels such as transfemoral, transjugular, transradial or transapical approaches, which may provide simpler access to the anchoring point.

First tissue anchor 182A is implanted as described hereinabove with reference to FIGS. 13A-D, as appropriate. As mentioned above, first implantation site 530 is shown as circumferential middle 521 of anterior leaflet 586; alternative first implantation sites 530 are set forth hereinbelow in Table 2. As mentioned with reference to FIG. 13C, after first tissue anchor 182A has been implanted at first implantation site 530, deployment tool 30 is removed from the subject's body, typically leaving catheter 506 in situ.

As shown in FIG. 15A, second tissue anchor 182B is implanted in the subject at second implantation site 540. For example, second tissue anchor 1829 may comprise helical tissue-coupling element 184, described hereinabove with reference to FIG. 4A, and second implantation site 540 may be within 1 cm of a site on the annulus that circumferentially corresponds to a septoposterior commissure 517; alternative second implantation sites 540 are set forth hereinbelow in Table 2. For some applications, the one or more tethers 132 comprise a single tether 132. For some applications, tether 132 defines a plurality of securement protrusions 560 spaced at intervals along tether 132, which protrusions serve as the friction-enhancing features. For some applications, as shown, protrusions 560 comprise respective cylinders on tether 132.

For some applications, outside the subject's body, the surgeon threads a free end of tether 132 through a lateral opening 582 of an outer tether-securing element 580 of second tissue anchor 182B, and then through a lumen of a delivery tube 614. Tether 132 thus connects first and second tissue anchors 182A and 182B.

For some applications, as shown in FIG. 15A, second tissue anchor 182B is implanted at second implantation site 540 using a torque-delivery cable 728 of the torque-delivery tool, as described in above-mentioned PCT Publication WO 2015/193728. Second tissue anchor 182B and torque-delivery cable 728 are introduced over tether 132 and through delivery tube 614, which itself is advanced through catheter 506. A tether-locking mechanism of second tissue anchor 182B is introduced in an unlocked state in which sliding of tether 132 through a lateral opening of second tissue anchor 1829 is not inhibited. Second tissue anchor 182B is implanted at second implantation site 540 by rotating torque-delivery cable 728 including a torque-delivery head).

The size of the tricuspid valve orifice is reduced by tensioning tether 132, so as to reduce regurgitation. Such tensioning may be performed by proximally pulling on the free end of tether 132, such that a portion of tether 132 is pulled through lateral opening 582 of second tissue anchor 182B. This tension can be applied remotely, i.e., via catheter 506. Application of such tension facilitates repair of an atrioventricular valve of the subject, such as tricuspid valve 504.

As shown in FIG. 15B, once the tension has been applied, torque-delivery cable 728 (including the torque-delivery head) is decoupled from second tissue anchor 182B, such as by removing a locking wire. As a result, a spring expands and presses tether 132 against an outer tether-securing element 780, both of which are described in above-mentioned PCT Publication WO 2015/193728. This pressing transitions the tether-locking mechanism to a locked state, in which state the sliding of tether 132 through the second tissue anchor 182B is inhibited. Such locking maintains the distance and tension between second tissue anchor 182B and first tissue anchor 182B.

As shown in FIG. 15C, after tether 132 has been tensioned, an excess portion of tether 132 remains free in the right atrium. It is generally undesirable to leave this excess portion free to move around in the atrium. For some applications, the excess portion of tether 132 is cut and removed from the atrium, using a cutting tool, such as thoracoscopic scissors, as known in the art. Further alternatively, for some applications, the excess portion is secured in a desired disposition in the vasculature of the right atrium, such as in inferior vena cava 508, superior vena cava 510, or a coronary sinus.

The following Table 2 sets forth exemplary combinations of (a) anatomical markers for first implantation site 530, (b) anatomical markers for second implantation site 540, and (c) external exit sites 550. These sites are listed by way of example and not limitation; the surgeon typically selects the exact sites based on the subject's individual needs and anatomy. Each of first and second implantation sites 530 and 540 is located within 1 cm of the site on the annulus that circumferentially corresponds to the respective anatomical marker (i.e., is at the same angular location or "o'clock" as the respective anatomical marker). The direction of the 1 cm from the site on the annulus may be either circumferentially (i.e., clockwise or counterclockwise) around the annulus, up the wall of the right atrium above the annulus, or a combination of circumferentially around the annulus and up the wall of the atrium. For example, as shown in FIG. 15C, septoposterior commissure 517 is near, but not on, the annulus, and second tissue anchor 182B is shown implanted at second implantation site 540, which is at the site on the annulus that circumferentially corresponds to this commissure. Second implantation site 540 could also be up to 1 cm clockwise or counterclockwise around the annulus from this site on the annulus, up to 1 cm up the wall of the atrium, or a combination of these two directions.

Typically, the surgeon uses the anatomical markers to find the exact locations of first and second implantation sites 530 and 540, which are within 1 cm of the anatomical markers, as described above. For example, the commissures are easily detectable using imaging, and thus represent good anatomical markers. However, the commissures are not appropriate for implantation (because they are too delicate), so, in this example, second tissue anchor 182B is implanted on the annulus or up the wall of the atrium, within 1 cm from the commissure.

TABLE 2

| First implantation site 530 anatomical marker | Second implantation site 540 anatomical marker | External exit site 550 |
| --- | --- | --- |
| Circumferential middle 521 of anterior leaflet 586 | Septoposterior commissure 517 | Right atrium 500 |
| Anteroposterior commissure 512 | Septoposterior commissure 517 | Right atrium 500 |
| Circumferential middle 521 of anterior leaflet 586 | Septoposterior commissure 517 | Right ventricle 552 |
| Anteroposterior commissure 512 | Septoposterior commissure 517 | Right ventricle 552 |
| Anteroposterior commissure 512 | a coronary sinus ostium 554 (labeled in FIG. 15C) | Right ventricle 552 |

Figure 16:
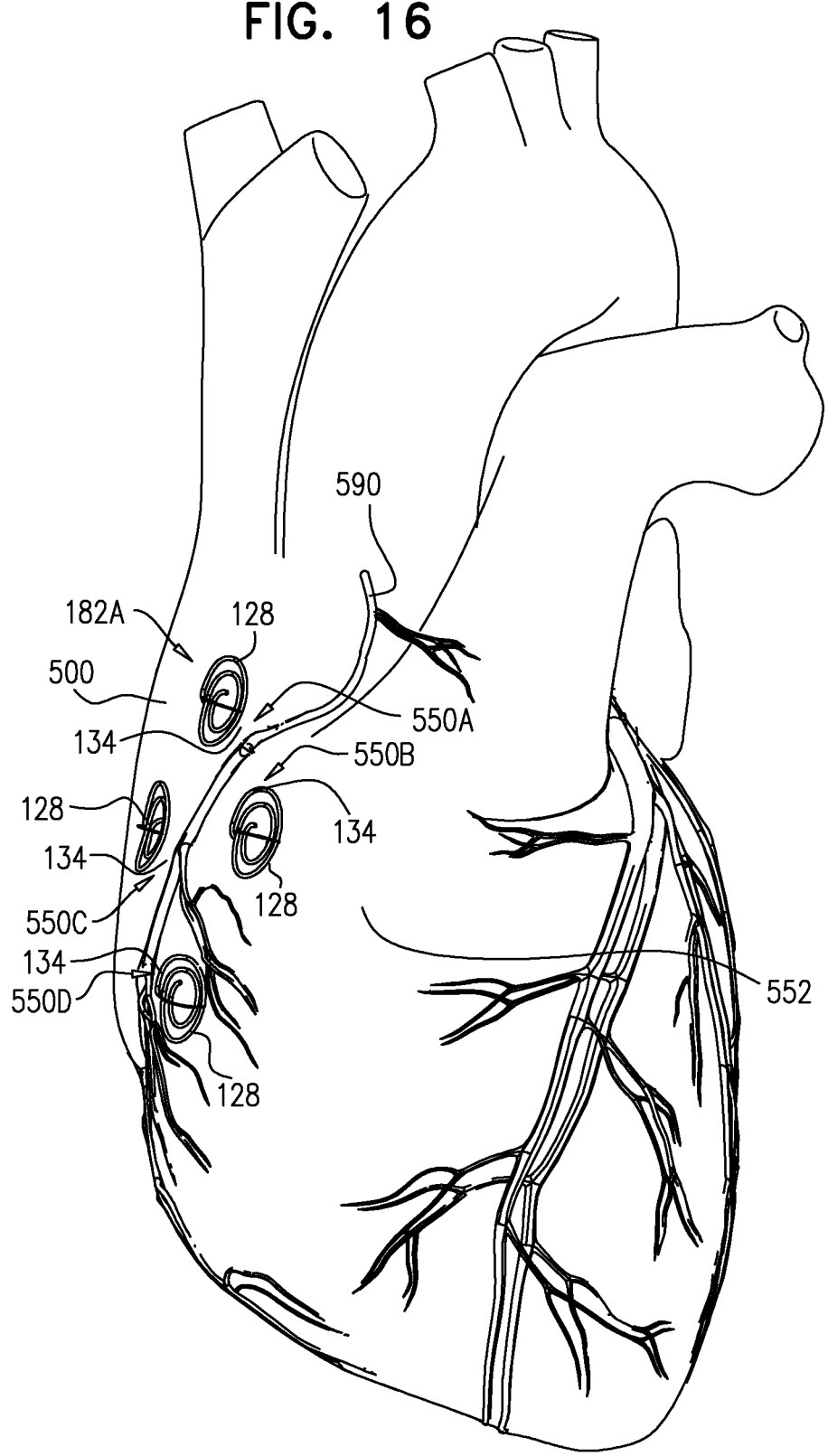
FIG. 16 is a schematic illustration of several external exit sites, in accordance with respective applications of the present invention.

Reference is now made to FIG. 16, which is a schematic illustration of several external exit sites 550, in accordance with respective applications of the present invention. External exit sites 550 are typically within 10 mm, such as 5 mm, of RCA 590 or branches from the RCA such as the posterior descending artery (PDA) or veins of the right ventricle. External exit sites 550A and 550C are on right atrium 500, and external exit sites 550B and 550D are on right ventricle 552.

For some applications, both first and second tissue anchors 182A and 182B comprise respective tissue anchors 20 (tissue anchors 200, 300, 340, 350, 430, 370, 400, 420, 470, or 490, or a combination of two different ones of these tissue anchors). For some applications, first tissue anchor 182A is implanted at an implantation site located with 1 cm of the site on the annulus that circumferentially corresponds to an anatomical marker between circumferential middle 521 of anterior leaflet 586 and anteroposterior commissure 512, inclusive. Alternatively or additionally, for some applications, second tissue anchor 182B is implanted at an implantation site located with 1 cm of the site on the annulus that circumferentially corresponds to an anatomical marker between a circumferential middle of a posterior leaflet and septoposterior commissure 517, inclusive.

Further alternatively or additionally, for some applications, second tissue anchor 182B is implanted at an implantation site located above the triangle of Koch, through the septal muscle into the left atrium above the level of the mitral valve. The off-centeredness of tissue anchor 20 allows the tissue-coupling element to be rotated during implantation so as to avoid contact with the mitral valve if the anchor enters the left atrium lower than expected. For some of these applications, first tissue anchor 182A comprises a stent, such as described hereinabove, which may be connected to second tissue anchor 182B by one or more tethers, at least one of which passes through a pulley, such as described in PCT Publication WO 2015/063580, which is incorporated herein by reference. Alternatively, the tissue anchors are implanted and coupled to one another under tension using the techniques described hereinabove with reference to FIG. 159, mutatis mutandis.

Reference is made to FIGS. 1A-16. For some applications, apparatus is provided for delivery in a constrained state within deployment tool 30, the apparatus comprising tissue anchor 20, which comprises (a) anchor shaft 122, and (b) tissue-coupling element 128, which comprises wire 150. When tissue anchor 20 is unconstrained by deployment tool 30:

anchor shaft 122 has central longitudinal axis 134,
  for applications in which tissue-coupling element 128 does not comprise tip 308, wire 150 of tissue-coupling element 128 is shaped as open loop 154 having more than one turn (optionally, around a center point 162), and (b) for applications in which tissue-coupling element 128 comprises tip 308, tissue-coupling element 128 is shaped as open loop 354 having more than one turn (optionally, around center point 162), and
  wire 150 extends from distal end 130 of anchor shaft 122 at a radially-outer end 164 of open loop 154 or 354, as the case may be.

These applications are optionally practiced in combination with any of inventive concepts 2-68, described hereinabove in the Summary of the Application section, mutatis mutandis.

For some applications, a method is provided that comprises (a) providing tissue anchor 20 having the characteristics described immediately above; (b) introducing, during a transcatheter procedure, tissue anchor 20 into a cardiac chamber of a heart of a subject, while tissue-coupling element 128 is constrained by deployment tool 30; (c) delivering tissue-coupling element 128 through a wall of the heart; and (d) at least partially releasing tissue anchor 20 from deployment tool 30.

The method is optionally practiced in combination with any of inventive concepts 205-277, described hereinabove in the Summary of the Application section, mutatis mutandis.

Although the techniques described herein have been described as being used to remodel the tricuspid valve, these techniques may also be used to remodel the mitral valve, mutatis mutandis. In addition, the tissue anchors described herein may be implanted on the surface of any wall of the heart or other organ where tension is to be applied, and rotationally repositioned to avoid obstructions of anatomic structures such as blood vessels or conduction systems, or pre-existing implants.

As used in the present application, including in the claims, when a range of values is specified using the word "between," the range includes the endpoint values.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,475,525 to Maisano et al.;
  U.S. Pat. No. 8,961,596 to Maisano et al.;
  U.S. Pat. No. 8,961,594 to Maisano et al.;
  International Application PCT/112011/000064, filed Jan. 20, 2011, which published as PCT Publication WO 2011/089601, and U.S. application Ser. No. 13/574,088 in the national stage thereof, which published as US Patent Application Publication 2013/0046380;
  U.S. application Ser. No. 13/553,081, filed Jul. 19, 2012, which published as US Patent Application Publication 2013/0018459;
  International Application PCT/IL2012/000282, filed Jul. 19, 2012, which published as PCT Publication WO 2013/011502;
  US Provisional Application 61/750,427, filed Jan. 9, 2013;
  US Provisional Application 61/783,224, filed Mar. 14, 2013;
  International Application PCT/IL2013/050470, filed May 30, 2013, which published as PCT Publication WO 2013/179295;
  US Provisional Application 61/897,491, filed Oct. 30, 2013;
  US Provisional Application 61/897,509, filed Oct. 30, 2013;
  U.S. application Ser. No. 14/143,355, filed Dec. 30, 2013, which published as US Patent Application Publication 2014/0114390;
  International Application PCT/IL2014/050027, filed Jan. 9, 2014, which published as PCT Publication WO 2014/108903;
  International Application PCT/112014/050233, filed Mar. 9, 2014, which published as PCT Publication WO 2014/141239;
  US Provisional Application 62/014,397, filed Jun. 19, 2014;
  International Application PCT/IB2014/002351, filed Oct. 28, 2014, which published as PCT Publication WO 2015/063580;
  U.S. application Ser. No. 14/525,668, filed Oct. 28, 2014, which published as US Patent Application Publication 2015/0119936;
  US Provisional Application 62/086,269, filed Dec. 2, 2014;
  US Provisional Application 62/131,636, filed Mar. 11, 2015;
  US Provisional Application 62/167,660, filed May 28, 2015; and
  International Application PCT/IB2015/001196, filed Jun. 14, 2015, which published as PCT Publication WO 2015/193728.

Patents and patent application publications incorporated by reference in the present patent application are to be considered an integral part of the application except that to the extent any terms are defined in these incorporated patents and patent application publications in a manner that conflicts with the definitions made explicitly or implicitly in the present specification, only the definitions in the present specification should be considered. In particular, the definition of "spiral" provided in US Provisional Application 62/086,269, filed Dec. 2, 2014, and US Provisional Application 62/167,660, filed May 28, 2015 should not be considered.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an implantable tissue anchor for delivery in a constrained state within a deployment tool, the implantable tissue anchor comprising:
    an anchor shaft;
    a tissue-coupling element, which (a) extends from a distal end of the anchor shaft, and (b) comprises (i) a wire, which is shaped as an open shape when the tissue anchor is unconstrained by the deployment tool; and (ii) a tip, which is fixed to a distal end of the wire, and has, at a widest longitudinal site along the tip, a greatest tip outer cross-sectional area that equals at least 150% of an average wire cross-sectional area of the wire;
    a flexible elongate tension member, which includes (a) a distal portion that is fixed to a site on the open shape, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses from the site on the open shape to the distal end of the anchor shaft when the tissue anchor is unconstrained by the deployment tool; and
    an anchor head fixed to a proximal portion of the anchor shaft, wherein the anchor head is shaped so as to define a passage in which the proximal portion of the flexible elongate tension member is slidably disposed,
    wherein the tissue anchor is configured to allow relative axial motion between the at least a portion of the anchor shaft and the longitudinal segment of the proximal portion of the flexible elongate tension member when the tissue anchor is unconstrained by the deployment tool, and
    wherein the tissue-coupling element is configured to be coupled to a wall of a heart such that a proximal end of the anchor head is disposed in a cardiac chamber or in the wall of the heart.

2. The apparatus according to claim 1, wherein a radius of the flexible elongate tension member is less than a radius of the wire.

3. The apparatus according to claim 2, wherein the radius of the flexible elongate tension member is less than 50% of the radius of the wire.

4. The apparatus according to claim 1, wherein the anchor shaft and the tissue-coupling element are integral to one another.

5. The apparatus according to claim 1,
    wherein the flexible elongate tension member comprises a locking stopper, which is axially fixed to the proximal or the crossing portion of the flexible elongate tension member, and
    wherein the locking stopper and the passage are sized and shaped such that the size and shape of the passage prevent proximal movement of the locking stopper past the passage.

6. The apparatus according to claim 1,
    wherein the tissue anchor is a first tissue anchor, and
    wherein the apparatus further comprises:
        a second tissue anchor, which is separate and distinct from the first tissue anchor; and
        one or more tethers, which are distinct from the flexible elongate tension member and are configured to couple (a) the proximal portion of the flexible elongate tension member to (b) the second tissue anchor.

7. The apparatus according to claim 6, wherein the one or more tethers are (a) fixed to the second tissue anchor and (b) not fixed to the anchor shaft of the first tissue anchor.

8. The apparatus according to claim 1,
    wherein the tissue anchor is a first tissue anchor, and
    wherein the apparatus further comprises a second tissue anchor, which is separate and distinct from the first tissue anchor, and
    wherein the flexible elongate tension member is coupled to the second tissue anchor.

9. The apparatus according to claim 1, wherein the wire is shaped so as to define a channel, which has a lateral opening at the site, and wherein the distal portion of the flexible elongate tension member passes through the lateral opening.

10. The apparatus according to claim 9, wherein the distal portion of the flexible elongate tension member passes through the lateral opening and extends distally through at least a portion of the channel.

11. The apparatus according to claim 10, wherein the distal portion of the flexible elongate tension member extends distally through the at least a portion of the channel to at least within 7 mm of a distal end of the wire.

12. The apparatus according to claim 1, wherein the tissue anchor is shaped so as to define a bend at an interface between the tissue-coupling element and the anchor shaft.

13. The apparatus according to claim 12, wherein the bend has an angle of between 60 and 120 degrees.

14. The apparatus according to claim 1, wherein the open shape is shaped as an open loop when the tissue anchor is unconstrained by the deployment tool.

15. The apparatus according to claim 14, wherein the crossing portion crosses at least a portion of the open loop when the tissue anchor is unconstrained by the deployment tool.

16. The apparatus according to claim 14, wherein the open loop has more than one turn when the tissue anchor is unconstrained by the deployment tool.

17. The apparatus according to claim 16, wherein the open loop is shaped as a spiral when the tissue anchor is unconstrained by the deployment tool.

18. The apparatus according to claim 17, wherein the spiral is shaped as an elliptical spiral when the tissue anchor is unconstrained by the deployment tool.

19. The apparatus according to claim 16, wherein the site is on an outermost turn of the open loop when the tissue anchor is unconstrained by the deployment tool.

20. The apparatus according to claim 16, wherein the wire extends from the distal end of the anchor shaft at a radially-outer end of the open loop when the tissue anchor is unconstrained by the deployment tool.

21. The apparatus according to claim 14, wherein, when the tissue anchor is unconstrained by the deployment tool:

the open loop has a greatest lateral dimension, measured perpendicular to the central longitudinal axis of the anchor shaft, and the at least a portion of the open loop crossed by the crossing portion has a length that equals at least 50% of the greatest lateral dimension.

22. The apparatus according to claim 1, wherein the longitudinal segment of the proximal portion of the flexible elongate tension member is coupled in sliding communication with the at least a portion of the anchor shaft when the tissue anchor is unconstrained by the deployment tool.

23. The apparatus according to claim 1, wherein the open shape is shaped as a portion of a circle or a portion of an ellipse when the tissue anchor is unconstrained by the deployment tool.

24. The apparatus according to claim 1, wherein when the tissue anchor is unconstrained by the deployment tool, if the tissue-coupling element were to be projected onto a plane that is perpendicular to the central longitudinal axis of the anchor shaft, the open shape would surround between 170 and 355 degrees of a point in the plane, which point falls on a projection onto the plane of a line segment that terminates at (a) the site on the wire and (b) a proximal end of the wire.

25. The apparatus according to claim 1, wherein the site on the open shape is located within 3 mm of a distal end of the open shape.

26. The apparatus according to claim 25, wherein the site on the open shape is at the distal end of the open shape.

27. The apparatus according to claim 1, wherein the wire is shaped so as to define a channel, and wherein the flexible elongate tension member passes through at least a portion of the channel.

28. The apparatus according to claim 27, wherein the flexible elongate tension member passes through the entire channel, and the site on the open shape is a distal-end opening of the open shape.

29. The apparatus according to claim 27, wherein the channel has a lateral opening at the site, and wherein the distal portion of the flexible elongate tension member passes through the lateral opening.

30. The apparatus according to claim 1, wherein the wire comprises a shape-memory alloy that causes the wire to automatically transition to the open shape when released from being constrained by the deployment tool to being unconstrained by the deployment tool.

31. The apparatus according to claim 1, wherein the tissue anchor further comprises an implantable sealing element, which is disposed around the anchor shaft, and is configured to provide a blood-tight seal with cardiac tissue and to promote hemostasis.

32. The apparatus according to claim 1, wherein the greatest tip outer cross-sectional area equals at least 200% of the average wire cross-sectional area.

33. The apparatus according to claim 32, wherein the greatest tip outer cross-sectional area equals at least 300% of the average wire cross-sectional area.

34. The apparatus according to claim 1, wherein the tip is shaped so as to define an atraumatic distal end.

35. A tissue anchor system comprising an implantable tissue anchor for delivery in a constrained state within a deployment tool, the implantable tissue anchor comprising:
an anchor shaft;
a tissue-coupling element, which (a) extends from a distal end of the anchor shaft, and (b) comprises (i) a wire, which is shaped as an open shape when the tissue anchor is unconstrained by the deployment tool; and (ii) a tip, which is fixed to a distal end of the wire, and has, at a widest longitudinal site along the tip, a greatest tip outer cross-sectional area that equals at least 150% of an average wire cross-sectional area of the wire; and
a flexible elongate tension member, which includes (a) a distal portion that is fixed to a site on the open shape, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses from the site on the open shape to the distal end of the anchor shaft when the tissue anchor is unconstrained by the deployment tool,
wherein the tissue anchor is configured to allow relative axial motion between the at least a portion of the anchor shaft and the longitudinal segment of the proximal portion of the flexible elongate tension member when the tissue anchor is unconstrained by the deployment tool, and
wherein the tissue anchor system further comprises one or more tethers, which are distinct from the flexible elongate tension member and are fixed to the proximal portion of the flexible elongate tension member.

36. The tissue anchor system according to claim 35, wherein the tissue anchor further comprises an implantable sealing element, which is disposed around the anchor shaft, and is configured to provide a blood-tight seal with cardiac tissue and to promote hemostasis.

37. The tissue anchor system according to claim 35, wherein the greatest tip outer cross-sectional area equals at least 200% of the average wire cross-sectional area.

38. The tissue anchor system according to claim 37, wherein the greatest tip outer cross-sectional area equals at least 300% of the average wire cross-sectional area.

39. The tissue anchor system according to claim 35, wherein the tip is shaped so as to define an atraumatic distal end.

40. A method comprising:
providing an implantable tissue anchor that comprises (a) an anchor shaft, (b) a tissue-coupling element, which (i) extends from a distal end of the anchor shaft, and (ii) comprises (1) a wire and (2) a tip, which is fixed to a distal end of the wire, and has, at a widest longitudinal site along the tip, a greatest tip outer cross-sectional area that equals at least 150% of an average wire cross-sectional area of the wire, (c) a flexible elongate tension member, and (d) an anchor head fixed to a proximal portion of the anchor shaft;
introducing, during a transcatheter procedure, the tissue anchor into a cardiac chamber of a heart of a subject, while the tissue-coupling element is constrained by a deployment tool;
delivering the tissue-coupling element through a wall of the heart;
at least partially releasing the tissue anchor from the deployment tool such that (a) the tissue-coupling element is unconstrained by the deployment tool, (b) the wire of the tissue-coupling element is shaped as an open shape, (c) a distal portion of the flexible elongate tension member is fixed to a site on the open shape, (d) a longitudinal segment of a proximal portion of the flexible elongate tension member runs alongside at least a portion of the anchor shaft, wherein the anchor head is shaped so as to define a passage in which the proximal portion of the flexible elongate tension member is slidably disposed, (e) a crossing portion of the flexible elongate tension member, disposed between the distal and the proximal portions along the flexible elongate tension member, crosses from the site on the open shape to the distal end of the anchor shaft, and (f) the tissue anchor allows relative axial motion between the at least a portion of the anchor shaft and the longitudinal segment of the proximal portion of the flexible elongate tension member;

coupling the tissue-coupling element to the wall of the heart such that a proximal end of the anchor head is disposed in the cardiac chamber or in the wall of the heart; and entirely removing the deployment tool from a body of the subject.

41. The method according to claim 40, further comprising, after delivering the tissue-coupling element through the wall of the heart, at least partially compressing the open shape by applying tension to the flexible elongate tension member.

42. The method according to claim 41,
wherein the tissue anchor is a first tissue anchor of a tissue anchor system that further comprises:
a second tissue anchor, which is separate and distinct from the first tissue anchor; and
one or more tethers, which are distinct from the flexible elongate tension member and are configured to couple (a) the proximal portion of the flexible elongate tension member to (b) the second tissue anchor, and
wherein applying the tension comprises applying tension to the one or more tethers.

43. The method according to claim 40, further comprising, after delivering the tissue-coupling element through the wall of the heart:
ascertaining whether the tissue-coupling element overlies a coronary blood vessel; and
if the tissue-coupling element overlies the coronary blood vessel, rotating the tissue anchor until the tissue-coupling element no longer overlies the coronary blood vessel.

44. The method according to claim 40, further comprising, after delivering the tissue-coupling element through the wall of the heart:
rotating the tissue anchor by rotating the anchor shaft; and
bringing the tissue-coupling element into contact with an external surface of the heart by applying tension to the flexible elongate tension member.

45. The method according to claim 44, wherein bringing the tissue-coupling element into contact with the external surface of the heart comprises bringing the tissue-coupling element into contact with the external surface of the heart without applying any tension to the anchor shaft.

46. The method according to claim 40, wherein a radius of the flexible elongate tension member is less than a radius of the wire.

47. The method according to claim 40, wherein the tissue anchor is shaped so as to define a bend at an interface between the tissue-coupling element and the anchor shaft.

48. The method according to claim 40, wherein the open shape is shaped as an open loop when the tissue anchor is unconstrained by the deployment tool.

49. The method according to claim 48,
wherein the flexible elongate tension member comprises a locking stopper, which is axially fixed to the proximal or the crossing portion of the flexible elongate tension member,
wherein the locking stopper and the passage are sized and shaped such that the size and shape of the passage prevent proximal movement of the locking stopper past the passage, and
wherein the method further comprises, after delivering the tissue-coupling element through the wall of the heart:
at least partially compressing the open loop by applying tension to the flexible elongate tension member;
applying additional tension to the flexible elongate tension member until proximal movement of the locking stopper is prevented by the passage; and
after the passage prevents proximal movement of the locking stopper past the passage, applying, to the flexible elongate tension member, additional tension that does not further compress the open loop.

50. The method according to claim 47, wherein the bend has an angle of between 60 and 120 degrees.

51. The method according to claim 48, wherein the crossing portion crosses at least a portion of the open loop when the tissue anchor is unconstrained by the deployment tool.

52. The method according to claim 48, wherein the open loop has more than one turn when the tissue anchor is unconstrained by the deployment tool.

53. The method according to claim 40, wherein the longitudinal segment of the proximal portion of the flexible elongate tension member is coupled in sliding communication with the at least a portion of the anchor shaft when the tissue anchor is unconstrained by the deployment tool.

54. The method according to claim 40, wherein the wire comprises a shape-memory alloy that causes the wire to automatically transition to the open shape when released from being constrained by the deployment tool to being unconstrained by the deployment tool.

55. Apparatus comprising an implantable tissue anchor for delivery in a constrained state within a deployment tool, the implantable tissue anchor comprising:
an anchor shaft;
a tissue-coupling element, which (a) extends from a distal end of the anchor shaft, and (b) comprises (i) a wire, which comprises a shape-memory alloy that causes the wire to automatically transition to an open shape when released from being constrained by the deployment tool to being unconstrained by the deployment tool; and (ii) a tip, which is fixed to a distal end of the wire, and has, at a widest longitudinal site along the tip, a greatest tip outer cross-sectional area that equals at least 150% of an average wire cross-sectional area of the wire;
a flexible elongate tension member, which includes (a) a distal portion that is fixed to a site on the open shape, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses from the site on the open shape to the distal end of the anchor shaft when the tissue anchor is unconstrained by the deployment tool; and
an anchor head fixed to a proximal portion of the anchor shaft, wherein the anchor head is shaped so as to define a passage in which the proximal portion of the flexible elongate tension member is slidably disposed,
wherein the tissue anchor is configured to allow relative axial motion between the at least a portion of the anchor shaft and the longitudinal segment of the proximal portion of the flexible elongate tension member when the tissue anchor is unconstrained by the deployment tool, and wherein the tissue-coupling element is configured to be coupled to a wall of a heart such that a proximal end of the anchor head is disposed in a cardiac chamber or in the wall of the heart.

56. The apparatus according to claim 55, wherein the anchor shaft and the tissue-coupling element are integral to one another.

57. The apparatus according to claim 55, wherein the tissue anchor further comprises an implantable sealing element, which is disposed around the anchor shaft, and is configured to provide a blood-tight seal with cardiac tissue and to promote hemostasis.

58. The apparatus according to claim 55, wherein the greatest tip outer cross-sectional area equals at least 200% of the average wire cross-sectional area.

59. The apparatus according to claim 58, wherein the greatest tip outer cross-sectional area equals at least 300% of the average wire cross-sectional area.

60. The apparatus according to claim 55, wherein the tip is shaped so as to define an atraumatic distal end.

61. A tissue anchor system comprising an implantable tissue anchor for delivery in a constrained state within a deployment tool, the implantable tissue anchor comprising:
an anchor shaft;
a tissue-coupling element, which (a) extends from a distal end of the anchor shaft, and (b) comprises (i) a wire, which comprises a shape-memory alloy that causes the wire to automatically transition to an open shape when released from being constrained by the deployment tool to being unconstrained by the deployment tool; and (ii) a tip, which is fixed to a distal end of the wire, and has, at a widest longitudinal site along the tip, a greatest tip outer cross-sectional area that equals at least 150% of an average wire cross-sectional area of the wire; and
a flexible elongate tension member, which includes (a) a distal portion that is fixed to a site on the open shape, (b) a proximal portion, which has a longitudinal segment that runs alongside at least a portion of the anchor shaft, and (c) a crossing portion, which (i) is disposed between the distal and the proximal portions along the flexible elongate tension member, and (ii) crosses from the site on the open shape to the distal end of the anchor shaft when the tissue anchor is unconstrained by the deployment tool,
wherein the tissue anchor is configured to allow relative axial motion between the at least a portion of the anchor shaft and the longitudinal segment of the proximal portion of the flexible elongate tension member when the tissue anchor is unconstrained by the deployment tool, and
wherein the tissue anchor system further comprises one or more tethers, which are distinct from the flexible elongate tension member and are fixed to the proximal portion of the flexible elongate tension member.

62. The tissue anchor system according to claim 61, wherein the tissue anchor further comprises an implantable sealing element, which is disposed around the anchor shaft, and is configured to provide a blood-tight seal with cardiac tissue and to promote hemostasis.

63. The tissue anchor system according to claim 61, wherein the greatest tip outer cross-sectional area equals at least 200% of the average wire cross-sectional area.

64. The tissue anchor system according to claim 63, wherein the greatest tip outer cross-sectional area equals at least 300% of the average wire cross-sectional area.

65. The tissue anchor system according to claim 61, wherein the tip is shaped so as to define an atraumatic distal end.

66. A method comprising:
providing an implantable tissue anchor that comprises (a) an anchor shaft, (b) a tissue-coupling element, which (i) extends from a distal end of the anchor shaft, and (ii) comprises (1) a wire and (2) a tip, which is fixed to a distal end of the wire, and has, at a widest longitudinal site along the tip, a greatest tip outer cross-sectional area that equals at least 150% of an average wire cross-sectional area of the wire, (c) a flexible elongate tension member, and (d) an anchor head fixed to a proximal portion of the anchor shaft;
introducing, during a transcatheter procedure, the tissue anchor into a cardiac chamber of a heart of a subject, while the tissue-coupling element is constrained by a deployment tool;
delivering the tissue-coupling element through a wall of the heart;
at least partially releasing the tissue anchor from the deployment tool such that (a) the tissue-coupling element is unconstrained by the deployment tool, (b) a shape-memory alloy of the wire of the tissue-coupling element causes the wire to automatically transition to an open shape, (c) a distal portion of the flexible elongate tension member is fixed to a site on the open shape, (d) a longitudinal segment of a proximal portion of the flexible elongate tension member runs alongside at least a portion of the anchor shaft, wherein the anchor head is shaped so as to define a passage in which the proximal portion of the flexible elongate tension member is slidably disposed, (e) a crossing portion of the flexible elongate tension member, disposed between the distal and the proximal portions along the flexible elongate tension member, crosses from the site on the open shape to the distal end of the anchor shaft, and (f) the tissue anchor allows relative axial motion between the at least a portion of the anchor shaft and the longitudinal segment of the proximal portion of the flexible elongate tension member;
coupling the tissue-coupling element to the wall of the heart such that a proximal end of the anchor head is disposed in the cardiac chamber or in the wall of the heart; and
entirely removing the deployment tool from a body of the subject.

67. The method according to claim 66, further comprising, after delivering the tissue-coupling element through the wall of the heart, at least partially compressing the open shape by applying tension to the flexible elongate tension member.

68. The method according to claim 67,
wherein the tissue anchor is a first tissue anchor of a tissue anchor system that further comprises:
a second tissue anchor, which is separate and distinct from the first tissue anchor; and
one or more tethers, which are distinct from the flexible elongate tension member and are configured to couple (a) the proximal portion of the flexible elongate tension member to (b) the second tissue anchor, and
wherein applying the tension comprises applying tension to the one or more tethers.

69. The method according to claim 66, further comprising, after delivering the tissue-coupling element through the wall of the heart:
   ascertaining whether the tissue-coupling element overlies a coronary blood vessel; and
   if the tissue-coupling element overlies the coronary blood vessel, rotating the tissue anchor until the tissue-coupling element no longer overlies the coronary blood vessel.

70. The method according to claim 66, further comprising, after delivering the tissue-coupling element through the wall of the heart:
   rotating the tissue anchor by rotating the anchor shaft; and
   bringing the tissue-coupling element into contact with an external surface of the heart by applying tension to the flexible elongate tension member.

71. The method according to claim 70, wherein bringing the tissue-coupling element into contact with the external surface of the heart comprises bringing the tissue-coupling element into contact with the external surface of the heart without applying any tension to the anchor shaft.

72. The method according to claim 66, wherein a radius of the flexible elongate tension member is less than a radius of the wire.

73. The method according to claim 66, wherein the tissue anchor is shaped so as to define a bend at an interface between the tissue-coupling element and the anchor shaft.

74. The method according to claim 73, wherein the bend has an angle of between 60 and 120 degrees.

75. The method according to claim 66, wherein the open shape is shaped as an open loop when the tissue anchor is unconstrained by the deployment tool.

76. The method according to claim 75, wherein the crossing portion crosses at least a portion of the open loop when the tissue anchor is unconstrained by the deployment tool.

77. The method according to claim 75, wherein the open loop has more than one turn when the tissue anchor is unconstrained by the deployment tool.

78. The method according to claim 75,
   wherein the flexible elongate tension member comprises a locking stopper, which is axially fixed to the proximal or the crossing portion of the flexible elongate tension member,
   wherein the locking stopper and the passage are sized and shaped such that the size and shape of the passage prevent proximal movement of the locking stopper past the passage, and
   wherein the method further comprises, after delivering the tissue-coupling element through the wall of the heart:
      at least partially compressing the open loop by applying tension to the flexible elongate tension member; applying additional tension to the flexible elongate tension member until proximal movement of the locking stopper is prevented by the passage; and
      after the passage prevents proximal movement of the locking stopper past the passage, applying, to the flexible elongate tension member, additional tension that does not further compress the open loop.

79. The method according to claim 66, wherein the longitudinal segment of the proximal portion of the flexible elongate tension member is coupled in sliding communication with the at least a portion of the anchor shaft when the tissue anchor is unconstrained by the deployment tool.

80. The method according to claim 66, wherein the wire comprises a shape-memory alloy that causes the wire to automatically transition to the open shape when released from being constrained by the deployment tool to being unconstrained by the deployment tool.

* * * * *